US011976292B2

(12) United States Patent
Pauza et al.

(10) Patent No.: US 11,976,292 B2
(45) Date of Patent: May 7, 2024

(54) NON-INTEGRATING VIRAL DELIVERY SYSTEM AND METHODS RELATED THERETO

(71) Applicant: AMERICAN GENE TECHNOLOGIES INTERNATIONAL INC., Rockville, MD (US)

(72) Inventors: Charles David Pauza, Rockville, MD (US); Tyler Lahusen, Rockville, MD (US)

(73) Assignee: American Gene Technologies International Inc., Rockville, MD (US)

( * ) Notice: Subject to any disclaimer, the term of this patent is extended or adjusted under 35 U.S.C. 154(b) by 653 days.

(21) Appl. No.: 16/308,373

(22) PCT Filed: Dec. 12, 2016

(86) PCT No.: PCT/US2016/066185
§ 371 (c)(1),
(2) Date: Dec. 7, 2018

(87) PCT Pub. No.: WO2017/213697
PCT Pub. Date: Dec. 14, 2017

(65) Prior Publication Data
US 2019/0264226 A1    Aug. 29, 2019

Related U.S. Application Data

(60) Provisional application No. 62/431,760, filed on Dec. 8, 2016, provisional application No. 62/347,552, filed on Jun. 8, 2016.

(51) Int. Cl.
C12N 15/86        (2006.01)
A61K 35/76        (2015.01)
A61K 38/18        (2006.01)
A61K 48/00        (2006.01)
A61P 31/18        (2006.01)
C07K 14/435       (2006.01)
C07K 14/475       (2006.01)
C07K 14/49        (2006.01)
C07K 14/51        (2006.01)
C07K 16/10        (2006.01)
C07K 16/22        (2006.01)
C07K 16/28        (2006.01)
C07K 16/32        (2006.01)
C12N 15/113       (2010.01)
C12N 15/63        (2006.01)
A61K 9/00         (2006.01)
A61K 39/00        (2006.01)

(52) U.S. Cl.
CPC .............. *C12N 15/86* (2013.01); *A61K 35/76* (2013.01); *A61K 38/1866* (2013.01); *A61K 48/00* (2013.01); *A61K 48/005* (2013.01); *A61P 31/18* (2018.01); *C07K 14/43504* (2013.01); *C07K 14/475* (2013.01); *C07K 14/49* (2013.01); *C07K 14/51* (2013.01); *C07K 16/10* (2013.01); *C07K 16/1045* (2013.01); *C07K 16/22* (2013.01); *C07K 16/2863* (2013.01); *C07K 16/32* (2013.01); *C12N 15/113* (2013.01); *A61K 9/0014* (2013.01); *A61K 9/0019* (2013.01); *A61K 9/0053* (2013.01); *A61K 2039/505* (2013.01); *A61K 2039/5256* (2013.01); *C07K 2317/14* (2013.01); *C12N 2310/141* (2013.01); *C12N 2710/20022* (2013.01); *C12N 2740/15043* (2013.01); *C12N 2740/16043* (2013.01); *C12N 2830/60* (2013.01)

(58) Field of Classification Search
CPC ................. C12N 15/86; C12N 15/113; C12N 2310/141; C12N 2740/15043
See application file for complete search history.

(56) References Cited

U.S. PATENT DOCUMENTS

| 5,668,255 | A | 9/1997 | Murphy |
| 5,674,703 | A | 10/1997 | Woo et al. |
| 6,156,514 | A | 12/2000 | Acevedo et al. |
| 6,399,383 | B1* | 6/2002 | Apt et al. |
| 6,635,472 | B1* | 10/2003 | Lauermann |
| 7,371,542 | B2 | 5/2008 | Ivanova et al. |

(Continued)

FOREIGN PATENT DOCUMENTS

| BR | 2515 | 3/2019 |
| CN | 101516365 | 8/2009 |

(Continued)

OTHER PUBLICATIONS

Bergvall et al. The E1 proteins. Virology 445:35-56, (Year: 2013).*
McBride, A. The papillomavirus E2 proteins. Virology 445:57-79, (Year: 2013).*
Chiang C-M et al. Viral E1 and E2 proteins support replication of homologous and heterologous papillomaviral origins. PNAS 89:5799-5803, (Year: 1992).*
Krajinovic et al. Sequencing data on the long control region of human papillomavirus type 16. J. General Virology 72:2573-2576, (Year: 1991).*

(Continued)

Primary Examiner — Quang Nguyen
(74) Attorney, Agent, or Firm — DLA Piper LLP (US)

(57) ABSTRACT

A non-integrating viral delivery system is disclosed. The system includes a viral carrier, wherein the viral carrier contains a defective integrase gene; a heterologous viral episomal origin of replication; a sequence encoding at least one initiator protein specific for the heterologous viral episomal origin of replication, wherein expression of the sequence encoding the at least one initiator protein specific for the heterologous viral episomal origin of DNA replication is inducible; and at least one gene, gene product, shRNA, siRNA, miRNA, or other RNA of interest.

12 Claims, 21 Drawing Sheets
Specification includes a Sequence Listing.

(56) References Cited

U.S. PATENT DOCUMENTS

| | | |
|---|---|---|
| 8,124,752 B2 | 2/2012 | Bumcrot et al. |
| 8,287,857 B2 | 10/2012 | Dudley et al. |
| 8,546,555 B2 | 10/2013 | Gould-Fogerite et al. |
| 8,993,532 B2 | 3/2015 | Hannon et al. |
| 9,522,176 B2 | 12/2016 | DeRosa et al. |
| 9,527,904 B2 | 12/2016 | Balazs |
| 9,834,790 B1 | 12/2017 | Pauza et al. |
| 9,834,791 B2 | 12/2017 | Zhang |
| 9,914,938 B2 | 3/2018 | Pauza et al. |
| 10,023,880 B2 | 7/2018 | Pauza et al. |
| 10,036,038 B2 | 7/2018 | Pauza et al. |
| 10,036,040 B2 | 7/2018 | Pauza et al. |
| 10,137,144 B2 | 11/2018 | Pauza et al. |
| 10,208,295 B2 | 2/2019 | DeRosa et al. |
| 10,233,464 B2 | 3/2019 | Pauza et al. |
| 2002/0168345 A1 | 11/2002 | Dong et al. |
| 2003/0013196 A1 | 1/2003 | Engleman et al. |
| 2003/0096787 A1 | 5/2003 | Perridcaudet et al. |
| 2003/0119770 A1 | 6/2003 | Lai |
| 2003/0138444 A1 | 7/2003 | Zavitz et al. |
| 2004/0142416 A1 | 7/2004 | Laipis et al. |
| 2004/0161412 A1 | 8/2004 | Penn et al. |
| 2004/0192629 A1 | 9/2004 | Xu et al. |
| 2004/0214158 A1 | 10/2004 | Sethi et al. |
| 2004/0248296 A1 | 12/2004 | Beresford et al. |
| 2005/0019927 A1 | 1/2005 | Markus et al. |
| 2005/0138677 A1 | 6/2005 | Pfister et al. |
| 2006/0057553 A1 | 3/2006 | Aguilar-Cordova |
| 2006/0183230 A1 | 8/2006 | Silla et al. |
| 2006/0246520 A1 | 11/2006 | Champagne et al. |
| 2007/0026521 A1 | 2/2007 | Colosi |
| 2007/0141679 A1 | 6/2007 | Sodroski |
| 2007/0203333 A1 | 8/2007 | McSwiggen et al. |
| 2008/0003225 A1 | 1/2008 | Vie et al. |
| 2008/0003682 A1 | 1/2008 | Lois-Caballe et al. |
| 2008/0039413 A1 | 2/2008 | Morris et al. |
| 2008/0131940 A1 | 6/2008 | Chiu |
| 2008/0153737 A1 | 6/2008 | Lieberman et al. |
| 2008/0199961 A1 | 8/2008 | Rasko et al. |
| 2008/0227736 A1 | 9/2008 | Chen et al. |
| 2008/0293142 A1 | 11/2008 | Liu et al. |
| 2009/0017543 A1 | 1/2009 | Wilkes et al. |
| 2009/0148936 A1 | 6/2009 | Stout et al. |
| 2009/0304688 A1 | 12/2009 | Fournie et al. |
| 2010/0017911 A1 | 1/2010 | Dawson et al. |
| 2010/0069372 A1 | 3/2010 | Kazantsev |
| 2010/0119511 A1 | 5/2010 | Wang et al. |
| 2010/0120155 A1 | 5/2010 | Brennan et al. |
| 2010/0286166 A1 | 11/2010 | Pey Rodriguez et al. |
| 2010/0316676 A1 | 12/2010 | Sanders |
| 2011/0008803 A1 | 1/2011 | Stockwell et al. |
| 2011/0177155 A1 | 7/2011 | Peer et al. |
| 2011/0207226 A1 | 8/2011 | Ni et al. |
| 2012/0053223 A1 | 1/2012 | Benkirane et al. |
| 2012/0027725 A1 | 2/2012 | Galvin |
| 2012/0114607 A1 | 5/2012 | Lai et al. |
| 2012/0034197 A1 | 8/2012 | Young et al. |
| 2012/0201794 A1 | 9/2012 | Chen et al. |
| 2013/0078276 A1 | 3/2013 | Robinson et al. |
| 2013/0090371 A1 | 4/2013 | Lu et al. |
| 2013/0142766 A1 | 6/2013 | Dodo et al. |
| 2013/0211380 A1 | 8/2013 | Aquino et al. |
| 2014/0155468 A1 | 6/2014 | Gregory et al. |
| 2014/0162894 A1 | 6/2014 | Hatchwell et al. |
| 2014/0178340 A1 | 6/2014 | Robbins et al. |
| 2014/0234958 A1 | 8/2014 | Kashara et al. |
| 2014/0248277 A1 | 9/2014 | Hoffman et al. |
| 2014/0336245 A1 | 11/2014 | Mingozzi et al. |
| 2015/0010578 A1 | 1/2015 | Balazs et al. |
| 2015/0018539 A1 | 1/2015 | Fellmann |
| 2015/0126580 A1 | 5/2015 | DePinho et al. |
| 2015/0132255 A1 | 5/2015 | Sorensen et al. |
| 2015/0176006 A1* | 6/2015 | Krause et al. |
| 2016/0060707 A1 | 3/2016 | Goldenberg et al. |
| 2016/0243169 A1 | 8/2016 | Chen et al. |
| 2016/0289681 A1 | 10/2016 | Rossi |
| 2017/0015976 A1 | 1/2017 | Nelson |
| 2017/0028036 A1 | 2/2017 | Mingozzi et al. |
| 2017/0037369 A1 | 2/2017 | Ramsborg et al. |
| 2017/0335344 A1 | 11/2017 | Pauza et al. |
| 2018/0010147 A1 | 1/2018 | Pauza |
| 2018/0142257 A1 | 5/2018 | Pauza |
| 2018/0142258 A1 | 5/2018 | Pauza |
| 2018/0161455 A1 | 6/2018 | Pauza |
| 2018/0177866 A1 | 6/2018 | Pauza |
| 2018/0195046 A1 | 7/2018 | Deng |
| 2018/0195050 A1 | 7/2018 | Szalay |
| 2018/0256624 A1 | 9/2018 | Pauza |
| 2018/0305716 A1 | 10/2018 | Pauza |
| 2018/0355032 A1 | 12/2018 | Roberts |
| 2019/0046633 A1 | 2/2019 | Pauza et al. |
| 2019/0062786 A1 | 2/2019 | Pauza et al. |
| 2019/0078096 A1 | 3/2019 | Lahusen et al. |
| 2019/0083523 A1 | 3/2019 | Pauza |
| 2019/0388456 A1 | 12/2019 | Pauza et al. |
| 2020/0063161 A1 | 2/2020 | Pauza |
| 2020/0087682 A1 | 3/2020 | Lahusen et al. |
| 2020/0109417 A1 | 4/2020 | Pauza et al. |
| 2020/0155590 A1 | 5/2020 | Zhennan |
| 2020/0181645 A1 | 6/2020 | Pauza |
| 2020/0318081 A1 | 10/2020 | Lahusen et al. |
| 2021/0047644 A1 | 2/2021 | Lahusen |

FOREIGN PATENT DOCUMENTS

| | | | |
|---|---|---|---|
| CN | 101679466 | 3/2010 | |
| CN | 101805750 | 8/2010 | |
| CN | 103184224 | 7/2013 | |
| CN | 105112370 | 12/2015 | |
| CN | 108883100 | 11/2018 | |
| EP | 1647595 | 4/2006 | |
| EP | 3402483 | 11/2018 | |
| EP | 3413926 | 12/2018 | |
| EP | 3426777 | 1/2019 | |
| EP | 3468617 | 4/2019 | |
| EP | 3468618 | 4/2019 | |
| EP | 3481418 | 5/2019 | |
| EP | 3481435 | 5/2019 | |
| IN | 201947000153 | 2/2019 | |
| JP | 2002506652 | 3/2002 | |
| JP | 2007-527240 | 9/2007 | |
| JP | 2008518591 | 6/2008 | |
| JP | 2008-538174 | 10/2008 | |
| JP | 2012508591 | 4/2012 | |
| JP | 2013-5300152 | 7/2013 | |
| JP | 2015-518838 | 7/2015 | |
| JP | 2016-502404 | 1/2016 | |
| WO | 199947691 | 9/1999 | |
| WO | 2002020554 | 3/2002 | |
| WO | 2003093436 | 11/2003 | |
| WO | 2004053137 | 6/2004 | |
| WO | 2005028634 | 3/2005 | |
| WO | 2005033282 | 4/2005 | |
| WO | 2006039721 | 4/2006 | |
| WO | 2006048215 | 5/2006 | |
| WO | 2007000668 | 1/2007 | |
| WO | 2007015122 | 2/2007 | |
| WO | 2007132292 | 11/2007 | |
| WO | 2007133674 | 11/2007 | |
| WO | WO2008/025025 | 2/2008 | |
| WO | 2008090185 | 7/2008 | |
| WO | 2009100928 | 8/2009 | |
| WO | 2009147445 | 12/2009 | |
| WO | 2010051521 | 5/2010 | |
| WO | 2010117974 | 10/2010 | |
| WO | 2010127166 | 11/2010 | |
| WO | 2011008348 | 1/2011 | |
| WO | 2011071476 | 6/2011 | |
| WO | 2011119942 | 9/2011 | |
| WO | WO 2011/119942 | * 9/2011 | |
| WO | WO-2011119942 A1 | * 9/2011 | ........... C12N 5/0696 |
| WO | 2012048303 | 4/2012 | |
| WO | 2012061075 | 5/2012 | |
| WO | WO2012145624 | 10/2012 | |

(56) References Cited

FOREIGN PATENT DOCUMENTS

| WO | 2013096455 | 6/2013 | |
| --- | --- | --- | --- |
| WO | 2014016817 | 1/2014 | |
| WO | 2014117050 | 7/2014 | |
| WO | 2014187881 | 11/2014 | |
| WO | 2015017755 | 2/2015 | |
| WO | 2015042308 | 3/2015 | |
| WO | 2015061491 | 4/2015 | |
| WO | 2015078999 | 6/2015 | |
| WO | WO 2015/078999 | * | 6/2015 |
| WO | 2015086854 | 8/2015 | |
| WO | WO2015164759 | 10/2015 | |
| WO | 2016046234 | 3/2016 | |
| WO | 2016061232 | 4/2016 | |
| WO | WO2016061232 | 4/2016 | |
| WO | 2016069716 | 5/2016 | |
| WO | 2016200997 | 7/2016 | |
| WO | 2016189159 | 12/2016 | |
| WO | 2017007994 | 1/2017 | |
| WO | 20170068077 | 4/2017 | |
| WO | 2017100551 | 6/2017 | |
| WO | 2017123918 | 7/2017 | |
| WO | 2017139065 | 8/2017 | |
| WO | 2017156311 | 9/2017 | |
| WO | 20170173453 | 10/2017 | |
| WO | 2017213697 | 12/2017 | |
| WO | 2017214327 | 12/2017 | |
| WO | 2018009246 | 1/2018 | |
| WO | 2018009847 | 1/2018 | |
| WO | 2018017882 | 1/2018 | |
| WO | 2018126112 | 7/2018 | |
| WO | 2018129540 | 7/2018 | |
| WO | 20180148443 | 8/2018 | |
| WO | 2018187231 | 10/2018 | |
| WO | 2018232359 | 12/2018 | |
| WO | WO2019070674 | 4/2019 | |
| WO | 2020097049 | 5/2020 | |
| WO | 2020243717 | 12/2020 | |

OTHER PUBLICATIONS

Seedorg et al. Human papillomavirus type 16 DNA sequence. Virology 145:181-185, (Year: 1985).*
Oh et al. "Lentiviral Vector Design Using Alternative RNA Export Elements," Retrovirology, vol. 4:38, pp. 1-10, (2007).
Pallikkuth et al., "Human Immunodeficiency Virus (HIV) gag Anti-Specific T-Helper and Granule-Dependent CD8 T-Cell Activities in Exposed but Uninfected Heterosexual Partners of HIV Type 1-Infected Individuals in North India," Clinical and Vaccine Immunology, vol. 14(9) pp. 1196-1202, (2007).
Vargas, J. Jr. et al., "Conditionally replicating lentiviral-hybrid episomal vectors for suicide gene therapy," Antiviral Res. Dec. 2008 vol. 80 No. 3, pp. 288-294.
Thompson et al., "Alkylamines cause Vγ9Vδ2 T-cell activation and proliferation by inhibiting the mevalonate pathway," Blood, Jan. 15, 2006, vol. 107, pp. 651-654.
Gober et al., "Human T Cell Receptor γδ Cells Recognize Endogenous Mevalonate Metabolites in Tumor Cells," J. of Experimental Med., Jan. 20, 2003, vol. 197, pp. 163-168.
Goepfert, et al., "Specificity and 6-Month Durability of Immune Responses Induced by DNA and Recombinant Modified Vaccinia Ankara Vaccines Expressing HIV-2 Virus-Like Particles," J. Infectious Diseases, Jul. 1, 2014, vol. 210, pp. 99-110.
Tebas, P. et al, "Antiviral effects of autologous CD4 T cells genetically modified with a conditionally replicating lentiviral vector expressing long antisense to HIV," Blood, 2013, vol. 121, No. 9, pp. 1524-1533.
Tebas, p. et al., "Gene Editing of CCR5 in Autologous CD4 T Cells of Persons Infected with HIV," The New England Journal of Medicine, vol. 370 (10), pp. 901-910, Mar. 6, 2014.
Li et al., "Reduced Expression of the Mevalonate Pathway Enzyme Farnesyl Pyrophosphate Synthase Unveils Recognition of Tumor Cells by Vγ2Vδ2 T Cells," J. of Immunology, 2009, vol. 182, pp. 8118-8124.

Wang et al., "Indirect Stimulation of Human Vγ2Vδ2 T Cells through Alterations in Isoprenoid Metabolism," J. of Immunology, vol. 187 pp. 5099-5113, (Nov. 15, 2011).
Stunkel et al., "The Chromatin Structure of the Long Control Region of Human Papillomavirus Type 16 Repress Viral Oncoprotein Expression," Journal of Virology, vol. 73, No. 3, pp. 1918-1930 (Mar. 1999).
Lu et al., "Anti-sense-Mediated Inhibition of Human Immunodeficiency Virus (HIV) Replication by Use of an HIV Type 1-Based Vector Results in Severely Attenuated Mutants Incapable of Developing Resistance," Journal of Virology, vol. 79, No. 13, pp. 7079-7088 (Jul. 2004).
Dieli et al., "Targeting Human γδ T Cells with Zoledronate and Interleukin-2 for Immunotherapy of Hormone-Refractory Prostate Cancer," Europe PMC Funders Group, Cancer Research, vol. 67(15), pp. 7450-1451, (Aug. 1, 2007).
Moser et al., "γδ T cells: novel initiators of adaptive immunity," Immunological Reviews, vol. 215, pp. 89-102 (Feb. 2, 2007).
Capietto, A. H. et al., "Stimulated γδ T Cells Increase the in Vivo Efficacy of Trastuzumab in HER-2+ Breast Cancer," J Immunology, vol. 187(2), pp. 1031-1038, (2011).
Chen, Z. and M. S. Freedman, "CD16+ γδ T Cells Mediate Antibody Dependent Cellular Cytotoxicity: Potential Mechanism in the Pathogenesis of Multiple Sclerosis," Clin Immunology, vol. 128(2), pp. 219-227, (2008).
Couzi, L. et al., "Antibody-Dependent Anti-Cytomegalovirus Activity of Human γδ T Cells Expressing CD16 (FcγRIIIa)," Blood, vol. 119(6), pp. 1418-1427, (2012).
Fisher, J. P. et al., "Effective Combination Treatment of GD2-Expressing Neuroblastoma and Ewing's Sarcoma Using Anti-GD2 ch14.18/CHO Antibody with Vγ9Vδ2+ γδT Cells," OncoImmunology, vol. 5(1), pp. e1025194, (2016).
Gertner-Dardenne, J. et al., "Bromohydrin pyrophosphate enhances antibody-dependent cell-mediated cytotoxicity induced by therapeutic antibodies," Blood 113(20): 4875-4884, (2009).
Poonia, B. and C. D. Pauza, "Gamma delta T cells from HIV+ donors can be expanded in vitro by zoledronate/interleukin-2 to become cytotoxic effectors for antibody-dependent cellular cytotoxicity," Cytotherapy 14(2): 173-181, (2012).
Schiller, C. B. et al., "CD19-Specific Triplebody SPM-1 Engages NK and γδ T Cells for Rapid and Efficient Lysis of Malignant B-Lymphoid Cells," Oncotarget, vol. 7(50), pp. 83392-83408, (2016).
Tokuyama, H. et al., "Vγ9Vδ2 T Cell Cytotoxicity Against Tumor Cells is Enhanced by Monoclonal Antibody Drugs—Rituximab and Trastuzumab," Int J Cancer, vol. 122(11), pp. 2526-2534, (2008).
Zufferey et al., "Self-Inactivating Lentivirus Vector for Safe and Efficient In Vivo Gene Delivery," Journal of Virology, vol. 72(12), pp. 9873-9880, (1998).
Ostertag et al., "Brain Tumor Eradication and Prolonged Survival from Intratumoral Conversion of 5-Fluorocytosine to 5-fluorouracil Using a Nonlytic Retroviral Replicating Vector," Neoro-Oncology 14(2), pp. 145-159, Feb. 2012.
Twitty et al., "Retroviral Replicating Vectors Deliver Cytosine Deaminase Leading to Targeted 5-Fluorouracil-Mediated Cytotoxicity in Multiple Human Cancer Types," Human Gene Therapy Methods, 27(1), pp. 17-31, Feb. 1, 2016.
Charron et al., "Dominant-Negative Interference in the Pahenu2 Mouse Model of PKU: Effectiveness of Vectors Expressing Either Modified Forms of Phenylalanine Hydroxylase (PAH) or Ribozymes Plus a Hardened PAH mRNA," Molecular Therapy, vol. 11, pp. S163-S164, (2005).
Fusetti, et al., "Structure of Tetrameric Human Phenylalanine Hydroxylase and Its Implications for Phenylketonuria," J. Bio. Chem., vol. 273, No. 27, pp. 16962-16967 (1998).
Hafid et al., "Phenylketonuria: A Review of Current and Future Treatments," Translational Pediatrics, vol. 4(4), pp. 304-317, (2015).
Blau et al., "Phenylketonuria," The Lancet, vol. 376(9750), pp. 1417-1427, (2010).
Chandler et al., "Vector Design Influences Hepatic Genotoxicity After Adeno-Associated Virus Gene Therapy," Journal of Clinical Investigation, vol. 125(2), pp. 870-880, (2015).

(56) References Cited

OTHER PUBLICATIONS

Christophersen et al., "A Technique of Transumbilical Portal Vein Catheterization in Adults," The Archives of Surgery, vol. 95(6), pp. 960-963, (1967). (Abstract Only).
Bartholome, "Genetics and Biochemistry of the Phenylketonuria-Present State," Human Genetics, vol. 51(3), pp. 241-245, (1979).
Donsante et al., "AAV Vector Integration Sites in Mouse Hepatocellular Carcinoma," Science, vol. 317(5837, p. 477, (2007).
Eisensmith et al., "Multiple Origins for Phenylketonuria in Europe," American Journal of Human Genetics, vol. 51(6), pp. 1355-1365, (1992).
Fisher et al., "The Inhibition of Phenylalanine and Tyrosine Hydroxylases by High Oxygen Levels," Journal of Neurochemistry, vol. 19(5), pp. 1359-1365, (1972). (Abstract Only).
Grisch-Chan et al., "Low-Dose Gene Therapy for Murine PKU Using Episomal Naked DNA Vectors Expressing PAH from Its Endogenous Liver Promoter," Molecular Therapy Nucleic Acids, vol. 7, pp. 339-349, (2017).
Guldberg et al., "Aberrant Phenylalanine Metabolism in Phenylketonuria Heterozygotes," Journal of Inherited Metabolic Disease, vol. 21(4), pp. 365-372, (1998).
Kaufman et al., "A Model of Human Phenylalanine Metabolism in Normal Subjects and in Phenylketonuric Patients," Proceedings of the National Academy of Sciences USA, vol. 96(6), pp. 3160-3164, (1999).
Kaufman et al., "Phenylalanine Hydroxylase Activity in Liver Biopsies from Hyperphenylalaninemia Heterozygotes: Deviation from Proportionality with Gene Dosage," Pediatric Research, vol. 9(8), pp. 632-634, (1975).
Longo et al., "Single-Dose, Subcutaneous Recombinant Phenylalanine Ammonia Lyase Conjugated with Polyethylene Glycol in Adult Patients with Phenylketonuria: An Open-Label, Multicentre, Phase 1 Dose-Escalation Trial," The Lancet, vol. 384(9937), pp. 37-44, (2014).
Mochizuki et al., "Long-Term Correction of Hyperphenylalaninemia by AAV-Mediated Gene Transfer Leads to Behavioral Recovery in Phenylketonuria Mice," Gene Therapy, vol. 11(13), pp. 1081-1086, (2004).
Nault et al., "Adeno-Associated Virus Type 2 as an Oncogenic Virus in Human Hepatocellular Carcinoma," Molecular & Cellular Oncology, vol. 3(2), p. e1095271, (2016).
Oh et al., "Reversal of Gene Expression Profile in the Phenylketonuria Mouse Model After Adeno-Associated Virus Vector-Mediated Gene Therapy," Molecular Genetics and Metabolism, vol. 86(Supp. 1), pp. S124-S132, (2005).
Oh et al., "Long-Term Enzymatic and Phenotypic Correction in the Phenylketonuria Mouse Model by Adeno-Associated Virus Vector-Mediated Gene Transfer," Pediatric Research, vol. 56(2), pp. 278-284, (2004).
Pan et al., "Biodistribution and Toxicity Studies of VSVG-Pseudotyped Lentiviral Vector After Intravenous Administration in Mice with the Observation of in Vivo Transduction of Bone Marrow," Molecular Therapy, vol. 6(1), pp. 19-29, (2002).
Shedlovsky et al., "Mouse Models of Human Phenylketonuria," Genetics, vol. 134(4), pp. 1205-1210, (1993).
Yagi et al., "Complete Restoration of Phenylalanine Oxidation in Phenylketonuria Mouse by a Self-Complementary Adeno-Associated Virus Vector," Journal of Gene Medicine, vol. 13(2), pp. 114-122, (2011).
Yano et al., "Evaluation of Tetrahydrobiopterin Therapy with Large Neutral Amino Acid Supplementation in Phenylketonuria: Effects on Potential Peripheral Biomarkers, Melatonin and Dopamine, for Brain Monoamine Neurotransmitters," PLoS One, vol. 11(8), p. e0160892, (2016).
Mason et al., "Inactivated Simian Immunodeficiency Virus-Pulsed Autologous Fresh Blood Cells as an Immunotherapy Strategy," Journal of Virology, vol. 83(3), pp. 1501-1510, (2009).
Blick et al., "Cyclophosphamide Enhances SB-728-T Engraftment to Levels Associated with HIV-RNA Control," CROI Conference on Retroviruses and Opportunistic Infections, Boston, Massachusetts, p. 141, (2014), (Abstract Only).
De Rose et al., "Safety, Immunogenicity and Efficacy of Peptide-Pulsed Cellular Immunotherapy in Macaques," Journal of Medical Primatology, vol. 27(2), pp. 69-78, (2008).
Smith et al., "Developments in HIV-1 Immunotherapy and therapeutic Vaccination," F1000Prime Reports, vol. 6, p. 42, (2014).
Charron, "Gene Therapy for Phenylketonuria: Dominant-Negative Interference in a Recessive Disease," Dissertation, University of Florida 2005, http://etd.fcla.edu/UF/UFE0011392/charron_c.pdf>, (retrieved Jul. 26, 2018) (2005).
Ding et al., "Administration-Route and Gender-Independent Longterm Therapeutic Correction of Phenylketonuria (PKU) in a Mouse Model by Recombinant Adeno-Associated Virus 8 Pseudotyped Vector-Mediated Gene Transfer," Gene Therapy, vol. 13, pp. 583-587, (Dec. 1, 2005).
Nowacki et al., "The PAH Mutation Analysis Consortium Database: Update 1996," Nucleic Acid Research, vol. 25(1), pp. 139-142, (Jan. 1, 1997).
Condiotti et al., "Prolonged Liver-Specific Transgene Expression by a Non-Primate Lentiviral Vector," Biochemical and Biophysical Research Communications, vol. 320(3), pp. 998-1006, (Jul. 30, 2004).
Wang et al., "Butyrophilin 3A1 Plays an Essential Role in Prenyl Pyrophosphate Stimulation of Human Vg2Vd2 T Cells," Journal of Immunology, vol. 191(3), pp. 1029-1042, (Jul. 5, 2013).
Jiang et al., "A Novel EST-Derived RNAi Screen Reveals a Critical Role for Farnesyl Diphosphate Synthase in Beta2-Adrenergic Receptor Internalization and Down-Regulation," FASEB Journal, vol. 26(5), pp. 1-13, (Jan. 25, 2012).
Miettinen et al., "Mevalonate Pathway Regulates Cell Size Homeostasis and Proteostasis Through Autophagy," Cell Reports, vol. 13(11), pp. 2610-2620, (Dec. 2015).
Tolmachov, "Designing Lentiviral Gene Vectors," Viral Gene Therapy, Chapter 13, pp. 263-284, (2011).
Tracey, "Human DNA Sequence from Clone RP1-288M22 on Chromosome 6q 12-13," Complete Sequence, National Center for Biotechnology. GenBank Entry. Retrieved from the internet: <https://www.ncbi.nlm.nih.gov/nucleotide/AL035467.23?report=genbank&log$=nucltop&blast_rank=1&RID=UUD4GX2D014>; pp. 1-34, (Jan. 24, 2013).
Gorziglia et al., "Elimination of Both E1 and E2A from Adenovirus Vectors Further Improves Prospects for In Vivo Human gene Therapy," Journal of Virology, vol. 70(6), pp. 4173-4178, (1996).
Vargas et al., "Novel Integrase-Defective Lentiviral Episomal Vectors for Gene Transfer," Human Gene Therapy, vol. 15(4), pp. 361-372, (Apr. 2004).
Wendelburg et al., "An Enhanced EBNA1 Variant with reduced IR3 Domain for Long-Term Episomal Maintenance and Transgene Expression of ORIP-Based Plasmids in Human Cells," Gene Therapy, vol. 5, pp. 1389-1399, (Oct. 1998).
Westerhout et al., "A Conditionally Replicating HIV-Based Vector that Stably Expresses an Antiviral shRNA Against HIV-1 Replication," Molecular Therapy: The Journal of the American Society of Gene Therapy, vol. 14(2), pp. 268-275, (May 2006).
Lam et al., "T-Cell Therapies for HIV," Immunotherapy, Future Medicine, vol. 5(4), pp. 407-414, (Apr. 2013).
Munoz et al., "Ex Vivo Expansion and Lentiviral Transduction of Macaca Nemestrina CD4 + T Cells," Journal of Medical Primatology, vol. 38(6), pp. 438-443, (Dec. 2009).
Porichis et al., "HIV-Specific CD4 T Cells and Immune Control of Viral Replication," Current Opinion in HIV and Aids, vol. 6(3), pp. 174-180, (May 2011).
Kavanagh et al., "Expansion of HIV-Specific CD4+ and CD8+ T Cells by Dendritic Cells Transfected with mRNA Encoding Cytoplasm- or Lysosome-Targeted Nef," Blood, American Society of Hematology, vol. 107(5), pp. 1963-1969, (Mar. 2006).
Akinsheye et al., "Fetal Hemoglobin in Sickle Cell Anemia," Blood, vol. 118(1), pp. 19-27, (2011).

(56) References Cited

OTHER PUBLICATIONS

Lin et al., "Up-Regulation of Bcl-2 is Required for the Progression of Prostate Cancer Cells from an Androgen-Dependent to an Androgen-Independent Growth Stage," Cell Research, vol. 17, pp. 531-536, (2007).
Lee et al., "Lentiviral delivery of short hairpin RNAs protects CD4 cells from multiple clades and primary isolates of HIV." Blood, 2005, vol. 106(3):818-826. (Year: 2005).
Choi et al., "Multiplexing Seven miRNA-Based shRNAs to Suppress HIV Replication." Molecular Therapy, 2015, vol. 23(2):310-320. Supplementary materials.
Spartevello et al., Development of Lentiviral Vectors Simultaneously Expressing Multiple siRNAs Against CCR5, vif and tat/rev Genes for an HIV-1 Gene Therapy Approach, Molecular Therapy—Nucleic Acids, 2016, vol. 5:1-12.
Blites, C., M. Abrahao, P. Bozza, E. M. Netto, A. Lyra and F. Bahia (2018). "Infection by HTLV-1 Is Associated with High Levels of Proinflammatory Cytokines in HIV-HCV-Coinfected Patients." J Acquir Immune Defic Syndr 77(2): 230-234.
Douek, D. C., J. M. Brenchley, M. R. Betts, D. R. Ambrozak, B. J. Hill, et al. (2002). "HIV preferentially infects HIV-specific CD4+ T cells." Nature 417(6884): 95-98.
Eguchi, K., N. Matsuoka, H. Ida, M. Nakashima, M. Sakai, et al. (1992). "Primary Sjogren's syndrome with antibodies to HTLV-I: clinical and laboratory features." Ann Rheum Dis 51(6): 769-776.
Futsch, N., R. Mahieux and H. Dutartre (2017). "HTLV-1, the Other Pathogenic Yet Neglected Human Retrovirus: From Transmission to Therapeutic Treatment." Viruses, 10, 1; doi:10.3390/v10010001.
Gessain, A., F. Barin, J. C. Vernant, O. Gout, L. Maurs, A. Calender and G. de The (1985). "Antibodies to human T-lymphotropic virus type-I in patients with tropical spastic paraparesis." Lancet 2(8452): 407-410.
Gessain, A. and O. Cassar (2012). "Epidemiological Aspects and World Distribution of HTLV-1 Infection." Front Microbiol 3: 388.
Goncalves, D. U., F. A. Proietti, J. G. Ribas, M. G. Araujo, S. R. Pinheiro, A. C. Guedes and A. B. Carneiro-Proietti (2010). "Epidemiology, treatment, and prevention of human T-cell leukemia virus type 1-associated diseases." Clin Microbiol Rev 23(3): 577-589.
Kagdi, H., M. A. Demontis, J. C. Ramos and G. P. Taylor (2018). "Switching and loss of cellular cytokine producing capacity characterize in vivo viral infection and malignant transformation in human T-lymphotropic virus type 1 infection." PLoS Pathog 14(2): e1006861.
Kagdi, H. H., M. A. Demontis, P. A. Fields, J. C. Ramos, C. R. Bangham and G. P. Taylor (2017). "Risk stratification of adult T-cell leukemia/lymphoma using immunophenotyping." Cancer Med 6(1): 298-309.
Macnamara, A., A. Rowan, S. Hilburn, U. Kadolsky, H. Fujiwara, et al. (2010). "HLA class I binding of HBZ determines outcome in HTLV-1 infection." PLoS Pathog 6(9): e1001117.
Manel, N., F. J. Kim, S. Kinet, N. Taylor, M. Sitbon and J. L. Battini (2003). "The ubiquitous glucose transporter GLUT-1 is a receptor for HTLV." Cell 115(4): 449-459.
Martinez, M. P., J. Al-Saleem and P. L. Green (2019). "Comparative virology of HTLV-1 and HTLV-2." Retrovirology 16(1): 21.
Mochizuki, M., T. Watanabe, K. Yamaguchi, K. Takatsuki, K. Yoshimura, et al. (1992). "HTLV-I uveitis: a distinct clinical entity caused by HTLV-I." Jpn J Cancer Res 83(3): 236-239.
Mosley, A. J., B. Asquith and C. R. Bangham (2005). "Cell-mediated immune response to human T-lymphotropic virus type I." Viral Immunol 18(2): 293-305.
Nagai, M. and M. Osame (2003). "Human T-cell lymphotropic virus type I and neurological diseases." J Neurovirol 9(2): 228-235.
Yamano, Y. and T. Sato (2012). "Clinical pathophysiology of human T-lymphotropic virus-type 1-associated myelopathy/tropical spastic paraparesis." Front Microbiol 3: 389.
Nishioka, K., I. Maruyama, K. Sato, I. Kitajima, Y. Nakajima and M. Osame (1989). "Chronic inflammatory arthropathy associated with HTLV-I." Lancet 1(8635): 441.

Osame, M., K. Usuku, S. Izumo, N. Ijichi, H. Amitani, et al. (1986). "HTLV-I associated myelopathy, a new clinical entity." Lancet 1(8488): 1031-1032.
Poiesz, B. J., F. W. Ruscetti, A. F. Gazdar, P. A. Bunn, J. D. Minna and R. C. Gallo (1980). "Detection and isolation of type C retrovirus particles from fresh and cultured lymphocytes of a patient with cutaneous T-cell lymphoma." Proc Natl Acad Sci U S A 77(12): 7415-7419.
Poiesz, B. J., F. W. Ruscetti, J. W. Mier, A. M. Woods and R. C. Gallo (1980). "T-cell lines established from human T-lymphocytic neoplasias by direct response to T-cell growth factor." Proc Natl Acad Sci U S A 77(11): 6815-6819.
Roc, L., C. de Mendoza, M. Fernandez-Alonso, G. Reina, V. Soriano and H. N. Spanish (2019). "Rapid subacute myelopathy following kidney transplantation from HTLV-1 donors: role of immunosuppresors and failure of antiretrovirals." Ther Adv Infect Dis 6: 2049936119868028.
Soker, S., S. Takashima, H. Q. Miao, G. Neufeld and M. Klagsbrun (1998). "Neuropilin-1 is expressed by endothelial and tumor cells as an isoform-specific receptor for vascular endothelial growth factor." Cell 92(6): 735-745.
Uchiyama, T., J. Yodoi, K. Sagawa, K. Takatsuki and H. Uchino (1977). "Adult T-cell leukemia: clinical and hematologic features of 16 cases." Blood 50(3): 481-492.
Dickler, H. B., et al. (1973). "Lymphocyte binding of aggregated IgG and surface Ig staining in chronic lymphocytic leukaemia." Clin Exp Immunol 14(1): 97-106.
Hassan et al., "Isolation of umbilical cord mesenchymal stem cells using human blood derivative accompanied with explant method," Stem Cell Investigation, pp. 1-8, (2019).
Huang et al., "An Efficient protocol to generate placental chorionic plate-derived mesenchymal stem cells with superior proliferative and immunomodulatory properties," Stem Cell Research & Therapy, pp. 1-15, (2019).
Quan Jun-Jie et al., "Parp3 interacts with FoxM1 to confer glioblastoma cell radio resistance", Tumor Biology, Karger, Basel, CH, vol. 36, No. 11, Jun. 4, 2015 (Jun. 4, 2015), pp. 8617-8624, XP036217799, ISSN: 1010-4283, DOI: 10.1007/S13277-015-3554-4 [retrieved on Jun. 4, 2015] *whole document*.
Jakobsson J. and Lundberg C.: "Lentiviral 1, 2, 4-10 vectors for use in the central nervous system", Molecular Therapy: The Journal of the American Society of Gene Therapy, Cell Press, US, vol. 13, No. 3, Mar. 1, 2006 (Mar. 1, 2006), pp. 484-493, XP005326761, ISSN: 1525-0016, DOI: 10.1016/ J.Ymthe.2005.11.012 *the whole document*.
Yun Jong Lee et al., "Poly (ADP-ribose) in 1-15 the pathogenesis of Parkinson's disease", BMB Reports, vol. 47, No. 8, Aug. 31, 2014 (Aug. 31, 2014), pp. 424-432, XP55671927, KR, ISSN: 1976-6696, DOI: 10.5483/BMBRep.2014.47.8.119 *the whole document*.
Lang Yoo et al., "Parp-1 regulates the expression of caspase-11", Biochemical and Biophysical Research Communications, vol. 408, No. 3, Apr. 22, 2011 (Apr. 22, 2011), pp. 489-493, XP028209824, ISSN: 0006-291X, DOI: 10.1016/ J. BBRC.2011.04.070 [retrieved on Apr. 22, 2011] *whole document*.
Tae-In Kam et al., "Poly (ADP-ribose) derived pathologic [alpha]—synuclein neurodegeneration in Parkinson's disease", Science, vol. 362, No. 6414, Nov. 1, 2018 (Nov. 1, 2018), p. eaat8407, XP55672116, US, ISSN: 00368075, DOI: 10.1126/science. aat8407 *whole document*.
Olsen A.L. and Feany M.B., "PARP Inhibitors and Parkinson's Disease", Jan. 1, 2019 (Jan. 1, 2019), XP55672111, retrieved from the Internet: URL: https://mfprac.com/web2019/07literature/literature/Neurology/ParkinsonPARPI_Olsen.pdf [retrieved on Feb. 27, 2020] *the whole document*.
Richard Lu et al., "Siman Virus 40-Based Replication of Catalytically Inactive Human Immunodeficiency Virus Type 1 Integrase Mutants in Nonpermissive T Cells and Monocyte-Derived Macrophages", Journal of Virology, Jan. 2004, p. 658-668. DOI: 10.1128/JVI.78.2658-668.2004.
FM Sverdrup et al., "Development of human papillomavirus plasmids capable of episomal replication in human cell lines", Gene Therapy, Mar. 26, 1999, p. 1317-1321, Retrieved from the Internet: URL: http://www.stockton-pressco.uk/gt.

(56) References Cited

OTHER PUBLICATIONS

Kathleen Van Craenenbroeck et al., "Episomal vectors for gene expression in mammalian cells", Eur J. Biochem, vol. 267, p. 5665-5678, Jul. 14, 2000.
Hee Yeon Kim., "Farnesyl diphosphate synthase is important for the maintenance of glioblastoma stemness," Experimental & Molecular Medicine, (2018).
Hong Wang., "Indirect Stimulation of Human V2V2 Cells Through Alterations in Isoprenoid Metabolism," The Journal of Immunology, (2011).
Z. Li, "Inhibition of farnesyl pyrophosphate synthase prevents angiotensin II-induced cardiac fibrosis in vitro," Clinical & Experimental Immunology, (2014).
Xiaofeng Jiang, "A novel EST-derived RNAi screen reveals a critical role for farnesyl diphosphate in B2-adrenerigic receptor internalization and down-regulation," The FASEB Journal, vol. 26, pp. 1-13(1995).
Jian Yang, "Lentiviral-Mediated Silencing of Farnesyl Pyrophosphate Synthase through RNA Interference in Mice," Biomed Research International, vol. 2015, Article ID 914026, 6 pages, (2015).
Yang Ye, "Knockdown of farnesyl pyrophosphate synthase prevents angiotensin II-medicated cardiac hypertrophy," The International Journal of Biochemistry & Cell Biology, vol. 42, pp. 2056-2064, (2010).
Jianqiang Li, "Reduced Expression of Mevalonate Pathway Enzyme Farnesyl Pyrophosphate Synthase Unveils Recognition of Tumor Cells by V9V2 Cells," The Journal of Immunology, pp. 8118-8124, (2019).
Daryl S. Schiller, "Parameters Influencing Measurement of the Gag Antigen-Specific T-Proliferative Response to HIV Type 1 Infection," AIDS Research and Human Retroviruses, vol. 16, No. 3, pp. 259-271, (2000).
Bergvall et al. "The E1 proteins", Virology 445; p. 35-56, (Year:2013).
McBride, A., "The Papillomavirus E2 proteins", Virology 445: p. 57-79, (Year: 2013).
Chiang C-m et al., "Viral E1 and E2 proteins support replication of homologous and heterologous papillomaviral origins." PNAS 89: p. 5799-5803, (Year: 1992).
Jaalouk, et al. "A Self-inactivating retrovector incorporating the IL-2 promoter for activation-induced transgene expression engineered t-cells," Virology Journal: p. 1-12, (Year: 2006).
Cronin et al., "Altering the Tropism of Lentiviral Vectors through Pseudotyping", Curr Gene Ther, Aug. 2005, vol. 5(4), pp. 687-398.
Cannon et al., "Pseudotype-Dependent Lentiviral Transduction of Astrocytes or Neurons in the Rat Substantia Nigra", Experimental Neurology, vol. 228, (Year: 2011), pp. 41-52, doi:10.1016/J.expneurol.2010.10.016.
Nada et al, "Enhancing adoptive cancer immunotherapy with Vγ2Vδ2 T cells through pulse zoledronate stimulation", Journal for Immunotherapy of Cancer, vol. 5, No. 1, (Feb. 21, 2017), pp. 1-23, (2017) DOI 10.1186/s40425-017-0209-6 *the whole document*.
Benyamine et al., "BTN3A molecules considerably improve Vγ9Vδ2T cells-based immunotherapy in acute myeloid leukemia," Oncolmmunology, vol. 5, No. 10, 10 pages, (Oct. 2, 2016), E1146843 *the whole document*.
Harly et al., "Key implication of CD277/butyrophilin-3 (BTN3A) in cellular stress sensing by a major human γδ T-cell subset," American Society of Hematology , vol. 120, No. 11, (Sep. 13, 2012), pp. 2269-2279, XP055081172, ISSN: 0006-4971, DOI: 10.1182/blood-2012-05-430470 *the whole document*.
Wang et al., "Intravenous Delivery of SiRNA Targeting CD47 Effectively Inhibits Melanoma Tumor Growth and Lung Metastasis", Molecular Therapy, pp. 1919-1929, vol. 21, No. 10, Oct. 2013.
Yang et al., "Construction of PARP-1 gene silencing cell lines by lentiviral-mediated RNA interference," School of Public Health, Guangdong Medical College, Abstract (2009).
Zhaobing Ding et al., "Liver-Directed, AAV-and Lentivirus-Mediated Gene Therapy in the Phenylketonuria Mouse Model Pah-enu2", Molecular Therapy, vol. 11, Supp. 1. (May 2005) XP055751452.
Ledley et al., "Retroviral-mediated gene transfer of human phenylalanine hydroxylase into NIH 3T3 and hepatoma cells", Proceedings of the National Academy of Sciences, vol. 83, No. 2. (Jan. 1, 1986), pp. 409-413, XP002583115.
Ledley et al., "Molecular biology of phenylalanine hydroxylase and phenylketonurina", Trends in Genetics, Elsevier Science Publishers B.V. Amsterdam, NL, vol. 1. (Jan. 1, 1985), pp. 309-313, XP025943064.
EPO; Examination Report dated Oct. 1, 2021 in Application No. 16904834.5.
USPTO; Corrected Notice of Allowance dated Apr. 13, 2021 in the U.S. Appl. No. 16/687,525.
USPTO; Issue Notification dated May 18, 2021 in the U.S. Appl. No. 16/687,525.
EP Office Action in European Application No. 16808223.8, dated Feb. 2, 2021, 5 pages.
EP Office Action in European Application No. 16808223.8, dated Oct. 12, 2021, 4 pages.
JP Office Action in Japanese Application No. 2018-563822, dated Jul. 15, 2021, 10 pages (with English translation).
JP Office Action in Japanese Application No. 2018-563892, dated Jul. 2, 2021, 11 pages (with English translation).
JP Office Action in Japanese Application No. 2021-021627, dated Sep. 29, 2021, 4 pages (with English translation).
LaFountaine et al., "Delivery and therapeutic applications of gene editing technologies ZFNs, TALENs, and CRISPR/Cas9", Intl Journal of Pharmaceutics, Oct. 2015, 494(1):180-194.
O'Connor et al., "Transcription factor binding sites in the long control region of genital HPVs", Human papillomaviruses, Oct. 1995, 20 pages.
U.S. Final Office Action in U.S. Appl. No. 15/580,661, dated Aug. 20, 2021, 20 pages.
U.S. Non-Final Office Action in U.S. Appl. No. 16/308,335, dated Nov. 29, 2021, 17 pages.
Wang et al., "HIV Vaccine Research: The Challenge and the Way Forward," Journal of Immunology Research, vol. 2015, Article ID 503978, 5 pages.
Bourguigon et al., "Processing of blood samples influences PBMC viability and outcome of cell-mediated immune responses in antiretroviral therapy-naïve HIV-1-infected patients," Journal of Immunological Methods, vol. 414, p. 1-10 (2014).
Briz et al., "Validation of Generation 4 Phosphorus-Containing Polycationic Dendrimer for Gene Delivery Against HIV-1," Current Medical Chemistry, vol. 19, p. 5044-5051, (2012).
Anderson et al., "Preintegration HIV-1 Inhibition by a Combination Lentiviral Vector Containing a Chimeric TRIM5a Protein, a CCR5 shRNA, and TAR Decoy," Molecular Therapy, vol. 17, No. 12, p. 2103-2114, Dec. 2009.
JP; Japanese Office Action in the Application No. 2017-567175 dated Jun. 15, 2020.
EPO; Extended European Search Report in the Application No. 18736295.9 dated Aug. 20, 2020.
USPTO; Notice of Allowance dated Jul. 10, 2020 in the U.S. Appl. No. 16/530,908.
USPTO; Final Office Action dated Jul. 27, 2020 in the U.S. Appl. No. 16/076,655.
JP; Japanese Office Action in the Application No. 2018-536892 dated Jun. 26, 2020.
US, Office Action issued in U.S. Appl. No. 16/308,335 on Oct. 6, 2023.
JP, Office Action issued in Japanese Application No. 2022-172256 on Oct. 19, 2023.
Nakahara et al., "Regulation of Human Papillomavirus (HPV) Genome Replication in the Viral Life Cycle and Its Association with the Viral Persistence and Cancer Development," Virus, 64(1), pp. 57-66, 2014.
EP, Office Action issued in European Patent Application No. 16808223.8 on Nov. 9, 2023.
Sailaja et al., "Many Different Papillomaviruses Have Low Transcriptional Activity in Spite of Strong Epithelial Specific Enhancers, " Journal of General Virology, 80, 1715-1724, 1999.

(56) References Cited

OTHER PUBLICATIONS

BR Office Action in Application No. BR112018075399-8 dated Jan. 16, 2024.
KR Office Action in Application No. 10-2023-7041421 dated Jan. 22, 2024.

* cited by examiner

NON-INTEGRATING VIRAL DELIVERY SYSTEM AND METHODS RELATED THERETO

CROSS-REFERENCE TO RELATED APPLICATIONS

This application is a U.S. national phase filing under 35 U.S.C. § 371 of PCT/US2016/066185 filed on Dec. 12, 2016, entitled "NON-INTEGRATING VIRAL DELIVERY SYSTEM AND METHODS RELATED THERETO," which claims priority to U.S. Provisional Patent Application No. 62/347,552 filed on Jun. 8, 2016 entitled "NON-INTEGRATING VIRAL DELIVERY SYSTEM AND METHODS OF USE THEREOF" and U.S. Provisional Patent Application No. 62/431,760 filed on Dec. 8, 2016 entitled "NON-INTEGRATING VIRAL DELIVERY SYSTEM AND METHODS RELATED THERETO," the disclosures of which are incorporated herein by reference.

FIELD OF INVENTION

The present invention relates generally to the field of viral vectors and systems for the delivery of genes and other therapeutic, diagnostic, or research uses. More specifically, embodiments of the present invention relate to non-integrating viral vectors and systems for the delivery of genes and other therapeutic, diagnostic, or research uses.

BACKGROUND TO THE INVENTION

Viral vectors have been used to transduce genes and other therapeutic nucleic acid constructs into target cells owing to their specific virus envelope-host cell receptor interactions and viral mechanisms for gene expression. As a result, viral vectors have been used as vehicles for the transfer of genes into many different cell types including, but not limited to, isolated tissue samples, tissue targets in situ and cultured cell lines. The ability to both introduce and express foreign genes in a cell is useful for the study of gene expression and the elucidation of cell lineages and pathways as well as providing the potential for therapeutic interventions such as gene therapy and various types of immunotherapy.

Several viral systems including lentivirus murine retrovirus, adenovirus, and adeno-associated virus have been proposed as potential therapeutic gene transfer vectors. However, many hurdles have prevented robust utilization of these as approved therapeutics. Research and development hurdles include, but are not limited to, stability and control of expression, genome packaging capacity, and construct-dependent vector stability. In addition, in vivo application of viral vectors can be limited by host immune responses against viral structural proteins and/or transduced gene products, which can result in deleterious anti-vector immunological effects.

Researchers have attempted to find stable expression systems as a way of overcoming some of these hurdles. One approach utilizes recombinant polypeptides or gene regulatory molecules, including small RNA, in such expression systems. These systems employ chromosomal integration of a transduced retrovirus genome, or at least a portion thereof, into the genome of the host cell. An important limitation with these approaches is that the sites of gene integration are generally random, and the number and ratio of genes integrating at any particular site are often unpredictable. Thus, vectors that rely on chromosomal integration result in permanent maintenance of the recombinant gene that may exceed the therapeutic interval, and plasmid or other non-replicating DNA is poorly controlled and may decay before completing a desired therapeutic interval.

Another approach is the use of a transient expression system. Under a transient expression system, the expression of the gene of interest is based on non-integrated plasmids, and hence the expression is typically lost as the cell undergoes subsequent division or the plasmid vectors are destroyed by endogenous nucleases. Accordingly, transient gene expression systems typically do not lead to sufficient expression over time and typically require repeated treatments, which are generally understood to be undesirable features.

SUMMARY OF THE INVENTION

A stable viral delivery system and methods are provided. In various aspects, the delivery system includes a transient expression system. According to one aspect, the delivery system is non-integrating. In another aspect the delivery system is both non-integrating and transient.

In various aspects and embodiments, the system variously includes one or all of a viral carrier, wherein the viral carrier contains a defective integrase gene; a heterologous viral episomal origin of DNA replication; a sequence encoding at least one initiator protein specific for the heterologous viral episomal origin of DNA replication, wherein expression of the sequence encoding the at least one initiator protein specific for the heterologous viral episomal origin of DNA replication is inducible; and at least one gene, gene product, shRNA, siRNA, miRNA, or other RNA of interest. The viral carrier may be a lentivirus. The heterologous viral episomal origin of DNA replication may be from a papillomavirus. The heterologous viral episomal origin of DNA replication may be from a human papillomavirus or a bovine papillomavirus.

The heterologous viral episomal origin of DNA replication may be from a human papillomavirus type 16 (HPV16). The heterologous viral episomal origin of DNA replication may be from a long control region (LCR) of HPV16. The heterologous viral episomal origin of DNA replication may include SEQ ID NO: 1. Optionally, the heterologous viral episomal origin of DNA replication may include a 5' truncation of SEQ ID NO: 1. The heterologous viral episomal origin of DNA replication may include a 5' truncation of at least about 200 nucleotides, or at least about 300 nucleotides, or at least about 400 nucleotides, or at least about 500 nucleotides, or at least about 600 nucleotides, or at least about 700 nucleotides of SEQ ID NO: 1. The heterologous viral episomal origin of DNA replication may include at least about 80% sequence identity, or at least about 85% sequence identity, or at least about 90% sequence identity, or at least about 95% sequence identity, or at least about 98% sequence identity with Frag 1 (SEQ ID NO: 2) (also referred to herein as Fragment 1), or Frag 2 (SEQ ID NO: 3) (also referred to herein as Fragment 2), or Frag 3 (SEQ ID NO: 4) (also referred to herein as Fragment 3), or Frag 4 (SEQ ID NO: 5) (also referred to herein as Fragment 4) of the LCR of HPV16. The heterologous viral episomal origin of DNA replication may include Frag 1 (SEQ ID NO: 2), or Frag 2 (SEQ ID NO: 3), or Frag 3 (SEQ ID NO: 4), or Frag 4 (SEQ ID NO: 5) of the LCR of HPV16.

The at least one initiator protein specific for the heterologous viral episomal origin of DNA replication may include E1 or an operative fragment thereof. The at least one initiator protein specific for the heterologous viral episomal origin of DNA replication may include E2 or an operative fragment thereof. The at least one initiator protein specific for the heterologous viral episomal origin of DNA replication may include EBNA-1 or an operative fragment thereof. Optionally, the system may include at least two initiator proteins specific for the heterologous viral episomal origin of replication. The at least two initiator proteins specific for the heterologous viral episomal origin of DNA replication may include either of E1 or E2, alone or in combination, or operative fragments thereof. The sequence encoding the at least one initiator protein may be present on a single discrete plasmid or a non-integrating viral vector. Optionally, the system may include at least two initiator proteins specific for the heterologous viral episomal origin of DNA replication, wherein the sequence encoding the at least two initiator proteins may be present on a single discrete plasmid or a non-integrating viral vector. Optionally, the system may include at least two initiator proteins specific for the heterologous viral episomal origin of DNA replication, wherein the sequence for a first initiator protein and the sequence for a second initiator protein may be present on discrete plasmids or non-integrating viral vectors.

In respect of the disclosed non-integrating viral delivery system, the at least one gene product may include an antibody, an antibody fragment, or a growth factor. The antibody may include an anti-HER2 antibody or a fragment thereof. The growth factor may include vascular endothelial growth factor (VEGF) or a variant thereof. The miRNA may include a CCR5 miRNA.

In another aspect, a pharmaceutical composition is disclosed. The pharmaceutical compositions include the non-integrating viral delivery system disclosed herein and at least one pharmaceutically acceptable carrier.

In another aspect, a method of expressing at least one gene, gene product, shRNA, siRNA, miRNA, or other RNA of interest in a cell is provided. The method includes contacting a cell with an effective amount of a non-integrating viral delivery system, wherein the system includes a viral carrier, wherein the viral carrier contains one or all of a defective integrase gene; a heterologous viral episomal origin of DNA replication; a sequence encoding at least one initiator protein specific for the heterologous viral episomal origin of DNA replication, wherein expression of the sequence encoding the at least one initiator protein specific for the heterologous viral episomal origin of DNA replication is inducible; and at least one gene, gene product, shRNA, siRNA, miRNA, or other RNA of interest.

In another aspect, a method of expressing at least one gene, gene product, shRNA, siRNA, miRNA, or other RNA of interest in a subject in need thereof is provided. The method includes administering to the subject in need thereof an effective amount of a non-integrating viral delivery system, wherein the system includes a viral carrier, wherein the viral carrier contains one or all of a defective integrase gene; a heterologous viral episomal origin of DNA replication; a sequence encoding at least one initiator protein specific for the heterologous viral episomal origin of DNA replication, wherein expression of the sequence encoding the at least one initiator protein specific for the heterologous viral episomal origin of DNA replication is inducible; and at least one gene, gene product, shRNA, siRNA, miRNA, or other RNA of interest. The sequence encoding the at least one initiator protein may be present on a single discrete plasmid, and the at least one initiator protein may include either of E1 or E2, alone or in combination, or operative fragments thereof. The method may further involve administering to the subject in need thereof a first amount of the single discrete plasmid to initiate a first level of expression of the at least one gene, gene product, shRNA, siRNA, miRNA, or other RNA of interest. The method may further involve administering to the subject in need thereof a second amount of the single discrete plasmid to initiate a second level of expression of the at least one gene, gene product, shRNA, siRNA, miRNA, or other RNA of interest. In situations when the second amount is lower than the first amount, the level of expression of the at least one gene, gene product, shRNA, siRNA, miRNA, or other RNA of interest may be reduced. In situations when the second amount is higher than the first amount, the level of expression of the at least one gene, gene product, shRNA, siRNA, miRNA, or other RNA of interest may be increased.

In another aspect, the non-integrating viral delivery system disclosed herein is optimized to produce a low level of basal expression of the at least one gene, gene product, shRNA, siRNA, miRNA, or other RNA of interest. The heterologous viral episomal origin of DNA replication may include at least about 80% sequence identity, or at least about 85% sequence identity, or at least about 90% sequence identity, or at least about 95% sequence identity, or at least about 98% sequence identity with SEQ ID NO: 1 or Frag 1 (SEQ ID NO: 2) of the LCR of HPV16.

In another aspect, the non-integrating viral delivery system disclosed herein is optimized to produce a low level of basal expression of the at least one gene, gene product, shRNA, siRNA, miRNA, or other RNA of interest, and the heterologous viral episomal origin of DNA replication may include SEQ ID NO: 1 or Frag 1 (SEQ ID NO: 2) of the LCR of HPV16.

In another aspect, the non-integrating viral delivery system disclosed herein is optimized to produce a moderate level of basal expression of the at least one gene, gene product, shRNA, siRNA, miRNA, or other RNA of interest, and the heterologous viral episomal origin of DNA replication may include at least about 80% sequence identity, or at least about 85% sequence identity, or at least about 90% sequence identity, or at least about 95% sequence identity, or at least about 98% sequence identity with Frag 2 (SEQ ID NO: 3), Frag 3 (SEQ ID NO: 4), or Frag 4 (SEQ ID NO: 5) of the LCR of HPV16. The system may be optimized to produce a moderate level of basal expression of the at least one gene, gene product, shRNA, siRNA, miRNA, or other RNA of interest, and the heterologous viral episomal origin of DNA replication may include Frag 2 (SEQ ID NO: 3), Frag 3 (SEQ ID NO: 4), or Frag 4 (SEQ ID NO: 5) of the LCR of HPV16.

In another aspect, a method of selecting an optimized non-integrating viral delivery system is disclosed. The method involves selecting a level of basal expression. Thereafter, when a level X is selected, a corresponding Y is selected, wherein Y corresponds to a heterologous viral episomal origin of DNA replication selected to be incorporated into the non-integrating viral delivery system, whereby when X=low; Y comprises SEQ ID NO: 1 or Frag 1 (SEQ ID NO: 2); and when X=moderate; Y comprises Frag 2 (SEQ ID NO: 3), Frag 3 (SEQ ID NO: 4), or Frag 4 (SEQ ID NO: 5) of the LCR of HPV16.

Further aspects include methods of treating, for example, an infectious disease. Further aspects include methods of preventing an infectious disease. In another aspect, methods of enhancing wound healing are disclosed. In another aspect, methods of treating a bone injury are disclosed. Further aspects include methods of treating a hereditary disease using the systems detailed herein.

The foregoing general description and following detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

FIG. 1(A) depicts a linear version of the vector and FIG. 1(B) depicts a circularized version of the vector.

DETAILED DESCRIPTION

Figure 1:
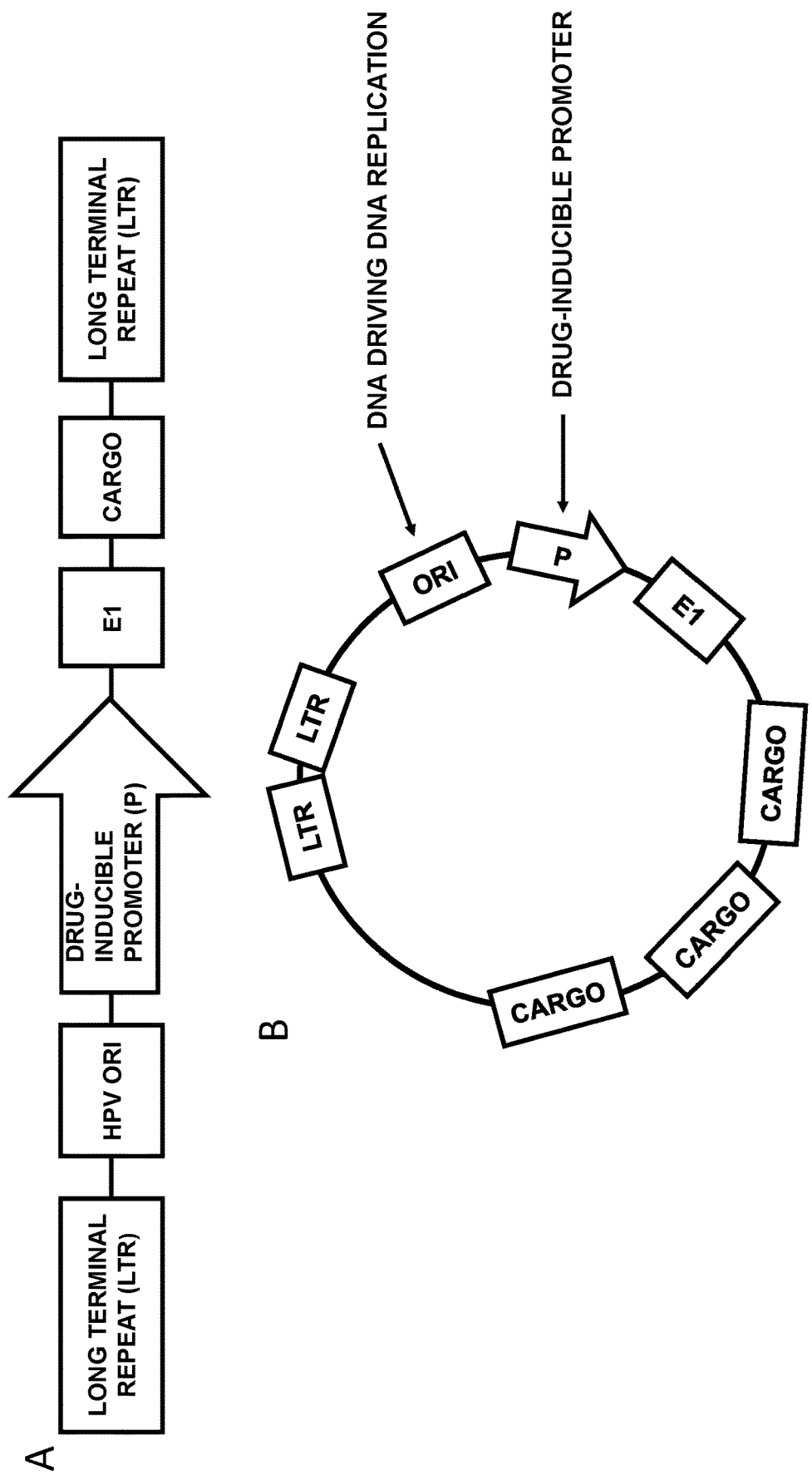
FIG. 1 depicts an exemplary vector-in-vector (VIV) embodiment of the invention.

Disclosed herein is a stable viral delivery system and methods. In various aspects, the delivery system includes a transient expression system. According to one aspect, the delivery system is non-integrating. In another aspect the delivery system is both non-integrating and transient.

In further aspects, non-integrating, episomally replicating viral vectors (e.g., lentiviral vectors) and methods of using the same are provided. Episomally replicating vectors of the present invention can contain viral components from viruses like Papovaviridae (e.g., bovine papillomavirus or BPV) or Herpesviridae (e.g., Epstein Barr Virus or EBV) or Hepadnaviridae (e.g., Hepatitis B Virus or HBV). Episomal replicating vectors derived from these viruses may contain a replication origin and at least one viral trans-acting factor, e.g., an initiator protein, such as E1 for BPV and EBNA-1 for EBV or HBV polymerase or terminus binding protein of Adenovirus. The process of episomal replication typically incorporates both host cell replication machinery and viral trans-acting factors.

By using heterogeneous viral origins of replication, novel vectors can be engineered with an "off" switch for expression of viral proteins required to recognize the origin of replication. Switching off DNA replication will cause therapeutic DNA levels to dramatically drop over time. Without wishing to be bound by any particular theory, it is believed that the non-replicating DNA simply degrades, such as by nuclease activity and as the host cell undergoes natural apoptosis (cell death) events over time. Eventually such non-replicating DNA may be non-detectible and completely or nearly cleared from the patient over time.

The disclosed systems and methods include reducing or preventing toxicity and toxic effects from over-expression or prolonged expression of transduced genes. Eliminating the gene once DNA replication ceases prevents unwanted gene expression or knockdown of host gene expression in the future. Likewise, combining the benefits of episomal replication into a heterogeneous viral system provides for a platform that can safely and efficiently transduce genes of interest into a variety of cell types.

Papillomavirus

Papillomaviruses replicate primarily as episomes in mammalian cells. Action of the viral E1 protein, which functions as a DNA helicase, on the viral origin of DNA replication (ori) drives the production of hundreds to thousands of DNA copies per cells depending on differentiation status of infected epithelial cells. Attempts have been made to develop papillomavirus-based gene delivery systems using what became known as "shuttle plasmids." With a bacterial origin of DNA replication to allow production of DNA in *E. coli* and a papillomavirus ori to allow episomal replication in mammalian cells, a number of studies have been performed to demonstrate safety and durability of gene expression. In most cases, the ori came from bovine papillomavirus.

Papillomaviruses have evolved to infect epidermal and epithelial cells. As infected cells differentiate from basal to luminal surfaces, papillomaviruses increase DNA replication and copy number becomes very high until a tremendous dose of virus is released at the lumenal surface. This makes papillomaviruses highly contagious as is apparent from human papillomavirus. The surge in copy number is due primarily to host factors. However, this feature of papillomavirus can be exploited to target transient gene therapy to epidermal and epithelial surfaces.

Certain features of papillomavirus are used in accordance with various aspects and embodiments of the present invention for driving expression and replication of an episomal vector, as well as targeting expression of the vector to specific cell types.

Epstein Barr Virus (EBV)

Epstein-Barr virus (EBV), also known as human herpesvirus 4, is a member of the herpes virus family. It is one of the most common human viruses, and most people become infected with EBV at some point in their lives.

EBV is a double-stranded DNA virus that contains approximately 85 genes; EBV is known to infect B cells and epithelial cells. EBV is capable of both lytic and latent replication, the latter of which results in a circularized version of the EBV genome translocating to the host cell nucleus where it may be replicated by host cell DNA polymerases.

EBV can undergo latent replication via at least three distinct pathways, but each one involves the expression of Epstein-Barr virus nuclear antigen 1 (EBNA-1), a protein that binds the episomal replication origin and mediates partitioning of the episome during division of the host cell. EBNA-1 plays an integral role in EBV gene regulation, replication, and episomal maintenance.

Certain features of EBV are used in accordance with various aspects and embodiments of the present invention.

Hepatitis B Virus (HBV)

Hepatitis B virus (HBV) is a member of the hepadnavirus family. It is a common human virus associated with progressive liver fibrosis, hepatitis and hepatocellular carcinoma.

HBV is a double stranded DNA virus that replicates through an RNA intermediate and depends on a viral polymerase. Stable maintenance of HBV in liver cells is due to the presence of covalently-closed viral DNA circular forms that are difficult to eradicate.

Thus, certain features of HBV are used in accordance with various aspects and embodiments of the present invention.

Retrovirus

Retrovirus is a virus family characterized by encoding a reverse transcriptase capable of generating DNA copies from RNA templates and integration of proviruses into the host cell chromosome. Lentivirus is a genus of retroviruses that can deliver a significant amount of viral nucleic acid into a host cell. Lentiviruses are characterized as having a unique ability to infect/transduce non-dividing cells, and following transduction, lentiviruses integrate their nucleic acid into the host cell's chromosomes.

Infectious lentiviruses have three main genes coding for the virulence proteins gag, pol, and env, and two regulatory genes including tat and rev. Depending on the specific serotype and virus, there may be additional accessory genes that code for proteins involved in regulation, synthesis, and/or processing viral nucleic acids and other replicative functions including counteracting innate cellular defenses against lentivirus infection.

Lentiviruses contain long terminal repeat (LTR) regions, which may be approximately 600 nt long. LTRs may be segmented into U3, R, and U5 regions. LTRs can mediate integration of retroviral DNA into the host chromosome via the action of integrase.

Alternatively, without functioning integrase, the LTRs may be used to circularize the viral nucleic acid.

Viral proteins involved in early stages of lentivirus replication include reverse transcriptase and integrase. Reverse transcriptase is a virally encoded, RNA-dependent DNA polymerase. The enzyme uses a viral RNA genome as a template for the synthesis of a complementary DNA copy. Reverse transcriptase also has RNaseH activity for the destruction of the RNA-template that is necessary to DNA second strand synthesis to complete production of the double-stranded DNA ready for integration. Integrase binds both the viral cDNA generated by reverse transcriptase and the host DNA. Integrase processes the LTR before inserting the viral genome into the host DNA. Tat acts as a transactivator during transcription to enhance the initiation and elongation of RNA copies made from viral DNA. The rev responsive element acts post-transcriptionally, regulating mRNA splicing and transport to the cytoplasm.

Certain features of retroviruses, including lentiviruses, are used in accordance with various aspects and embodiments of the present invention.

Vector-in-Vector System

A novel vector-in-vector (VIV) system is provided that can precisely regulate the delivery and expression of genes by combining desirable features from various viral species. Many viral vectors, including lentivirus (LV) platforms, may be used. Lentiviral transduction, like most other forms of stable transduction, results in chromosomal integration of the LV payload (e.g., gene of interest). In accordance with various aspects, chromosomal integration is abolished through selective mutations that inactivate the viral integrase gene.

The papillomavirus ori plus E1 protein, or the EBV ori plus EBNA-1 or the Hepadnavirus termini plus viral polymerase are used herein, as part of the genetic cargo of a heterologous virus that would not ordinarily be able to be maintained episomally. Incorporating this heterogeneous viral replication machinery into a lentiviral vector leaves approximately 5 kb of additional cargo space available to accommodate therapeutic genes of interest.

Additionally, other control elements can be incorporated into the disclosed VIV system. As a non-limiting example, the expression of E1 or E2 or EBNA-1 or HBV polymerase can be driven by an inducible promoter. Further, as a non-limiting example, E1 and/or E2 can be expressed using plasmids or non-integrating viral vectors. Numerous types of inducible promoters are known in the art, and for the purposes of this invention, inducible promoters can include but are not limited to promoters that respond to antibiotics (i.e., tetracyclines, aminoglycosides, penicillins, cephalosporins, polymyxins, etc.) or other drugs, copper and other metals, alcohol, steroids, light, oxygen, heat, cold, or other physical or chemical stimulation. For example, a method of using the disclosed viral system includes employing a tetracycline-inducible gene expression that depends upon a constant supply of the drug for expression of the cargo genes. A compound used to induce the inducible promoter may be added once or repeatedly depending on the duration of episomal replication and timing of cargo delivery that is desired. DNA replication and maintenance of the episome depends variously on E1, E2 and/or EBNA-1 induction, which in turn depends upon an inducer of gene expression (i.e., tetracycline).

An exemplary VIV system is shown in FIG. 1. The disclosed VIV comprises at least one gene or nucleotide sequence of interest (e.g. cargo as shown in FIG. 1A). The genes or sequences incorporated into the VIV will depend upon the purpose of the VIV. Referring generally to FIG. 1, a lentivirus is packaged with an integrase-defective system or transduction is performed in the presence of clinical drugs used to block integrase activity (e.g., Dolutegravir or Raltegravir). Failing to integrate, the linear double strand vector DNA will generally circularize (e.g. FIG. 1B) using host enzymatic machinery. Optionally, a drug inducible promoter can be activated to express E1 and/or E2 protein if desired, which will in turn drive DNA replication. Therapeutic cargo will be expressed from the integrated cassette(s). In various embodiments, the compound that induces the inducible promoter (also referred to herein as an "inducer") is withdrawn or terminated. Termination of the inducer will down regulate E1 and/or E2 synthesis. In further embodiments, E1 and/or E2 production is effectively terminated. In either event, this will lead to declining levels of episomal DNA and eventually elimination of the vector construct.

Figure 2:
FIG. 2 depicts an exemplary vector-in-vector (VIV) embodiment (also referred to herein as Vector 1) that contains an E1 initiator protein.

A further exemplary diagram of a VIV system is shown in FIG. 2. An E1 initiator protein is present and the cargo is GFP under an EF1-HTLV promoter. While FIGS. 1 and 2 depict a VIV system containing E1, FIG. 4, as described herein, depicts a VIV system containing both E1 and E2 on a single viral vector. In a further embodiment, in order to express both E1 and E2 from the same mRNA, an internal ribosome entry site (IRES) is added to allow for re-initiation of protein translation. Initiator proteins such as E1 and E2 can also be expressed on separate plasmids or non-integrating lentiviral vectors.

Figure 4:
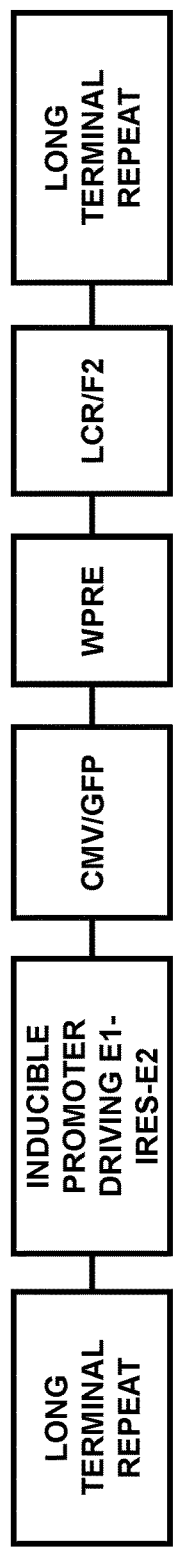
FIG. 4 depicts an exemplary vector-in-vector (VIV) embodiment (also referred to herein as Vector 19) that contains both E1 and E2 initiator proteins.

A further exemplary diagram of a VIV system is shown in FIG. 4. The genetic cargo is represented by a CMV/GFP cassette. The cargo gene sequences may be amplified by polymerase chain reaction (PCR). For example, synthetic oligonucleotide primers can be used, such as primers which are identical to the 5' end of the cargo gene and/or complementary to the 3' end of the cargo gene. The 5' primer can be extended from its 5' end with a recognition site for an endonuclease. The 3' primer can also be extended at its 3' end with the complement for an endonuclease recognition. The resulting amplified cargo gene sequences can be annealed into a suitable vector, such as a lentiviral vector. Non-limiting examples of the genetic cargo include CMV/VEGF, CMV/anti-epidermal growth factor receptor (EGFR), an anti-HER2 antibody, or a miRNA suppressing C-C chemokine receptor type 5 (CCR5).

Suitable expression of the cargo may be determined by an appropriate assay. For example, DNA copy numbers can be measured by quantitative PCR. Protein products translated from non-limiting examples such as Vector 1 or Vector 19 (as described herein) can be measured, for example, by analytical flow cytometry. An ELISA assay may be used to detect the presence of certain cargo, such as a secreted protein, such as VEGF. A Western blot technique may also be used to detect certain cargo such as an antibody, such as anti-EGFR. Further, monitoring a reduction in cell surface expression of a cargo protein, such as a chemokine receptor such as CCR5, can also be employed.

In respect of the cargo, and serving as a non-limiting example, the gene encoding platelet-derived growth factor (PDGF) can be incorporated as a gene along with shRNA, siRNA, miRNA, and/or other gene-silencing RNA of interest into a VIV used to promote wound healing. The disclosed VIV system is not limited to a particular type of gene or sequence that can be expressed.

The disclosed VIV can incorporate numerous therapeutic or prophylactic genes or sequences including, for example, sequences that encode antibodies directed to an antigen associated with an infectious disease or cancer (including antigens on replicating pathogens and antigens that are exogenous toxins and antigens on tumor cells), platelet derived growth factor, vascular endothelial growth factor, brain derived growth factor, nerve growth factor, human growth factor, human chorionic gonadotropin, cystic fibrosis transmembrane conductance regulator (CFTR), dystrophin or dystrophin-associated complex, phenylalanine hydroxylase, lipoprotein lipases, α- and/or β-thalassemias, factor VIII, bone morphogenetic proteins 1-4, cyclooxygenase 2, vascular endothelial growth factor, chemokine receptor CCR5, chemokine receptor CXCR4, chemokine receptor CXCR5, antisense DNA or RNA against autoimmune antigens involved in colitis, inflammatory bowel disease or Crohn's disease, small interfering RNA that are involved in addiction including miRNA regulating neural attenuation to opiates or alcohol, tumor suppressor genes, genes regulating cell survival including pro- or anti-apoptosis genes and pro- or anti-autophagy genes, genes encoding radiation resistance factors, genes encoding light emitting proteins used for tracking tumor cell metastasis or other cell trafficking phenomena, or a variety of other therapeutically useful sequences that may be used to condition the body for maximum effect of radiation, surgical or chemotherapeutics or to protect tissues against radiation, surgical or chemotherapeutics, to modify the host or graft tissues to improve organ transplantation or to suppress hyprerreactivity especially in the airway.

Without limiting any of the foregoing, cargo can include diagnostic proteins such as GRP and mCherry, as well as cDNAs, micoRNAs, shRNAs, and antibodies. Further, cargo can include specific cargo such as VEGF and BMP, as described herein.

In further aspects, it is desirable to maintain the genes in episomal form in a VIV system as a "safety switch." For example, where a particular gene product is toxic, withdrawal of the inducer molecule will reduce or terminate DNA replication. Episome numbers will subsequently decline, and the gene and vector will eventually disappear. Unlike traditional regulated gene expression as the safety switch, the disclosed expression construct is degraded by endogenous nucleases and diluted by cell division until it has effectively disappeared, thereby preventing any short- or long-term breakthrough expression.

In accordance with a further aspect, maintaining a gene, gene product, shRNA, siRNA, miRNA, and/or other gene-silencing RNA of interest in episomal form also allows for regulating the copy number over a broad range and at much higher levels than is achieved by traditional lentivirus transduction.

The disclosed VIV system presents numerous benefits. For instance, episomal DNA is less susceptible to chromosomal modification, which can lead to gene silencing of traditional transduction vectors. Likewise, VIV episomal DNA vectors support active gene delivery at least over short- to medium-range time intervals of about 1 to about 4 months, and possibly longer. In other embodiments of the invention, episomal DNA vectors support active gene delivery over a period of about 1, about 2, about 3, about 4, about 5, about 6, about 7, about 8, about 9, about 10, about 11, or about 12 weeks or longer. In other embodiments, episomal DNA vectors support active gene delivery over a period of about 1 month, 2 months, 3 months, 4 months, 5 months, 6 months, 7 months, 8 months, 9 months, 10 months, 11 months, 12 months, or longer. Any combination of these time periods can also be used in the methods of the invention, e.g., 1 month and 1 week, or 3 months and 2 weeks.

While there are benefits specifically associated with the use of a lentiviral carrier for incorporation of the disclosed VIV system, the disclosed system is not limited to a single type of viral vector. Any DNA virus or virus that uses a DNA intermediate can be used as a carrier for incorporating the VIV system herein, including but not limited to lentivirus, adeno-associated virus (AAV), adenovirus, vaccinia, herpes virus, measles virus, hepadnavirus, parvovirus and murine viruses.

Without limiting any of the foregoing, in an aspect of the invention, a non-integrating viral delivery system is disclosed. The system includes a viral carrier, wherein the viral carrier contains a one or more of a defective integrase gene; a heterologous viral episomal origin of replication; a sequence encoding at least one initiator protein specific for the heterologous viral episomal origin of replication, wherein expression of the sequence encoding the at least one initiator protein specific for the heterologous viral episomal origin of DNA replication is inducible; and at least one gene, gene product, shRNA, siRNA, miRNA, or other RNA of interest. The viral carrier may be a lentivirus. The heterologous viral episomal origin of DNA replication may be from a papillomavirus. The heterologous viral episomal origin of DNA replication may be from a human papillomavirus or a bovine papillomavirus.

Figure 11:
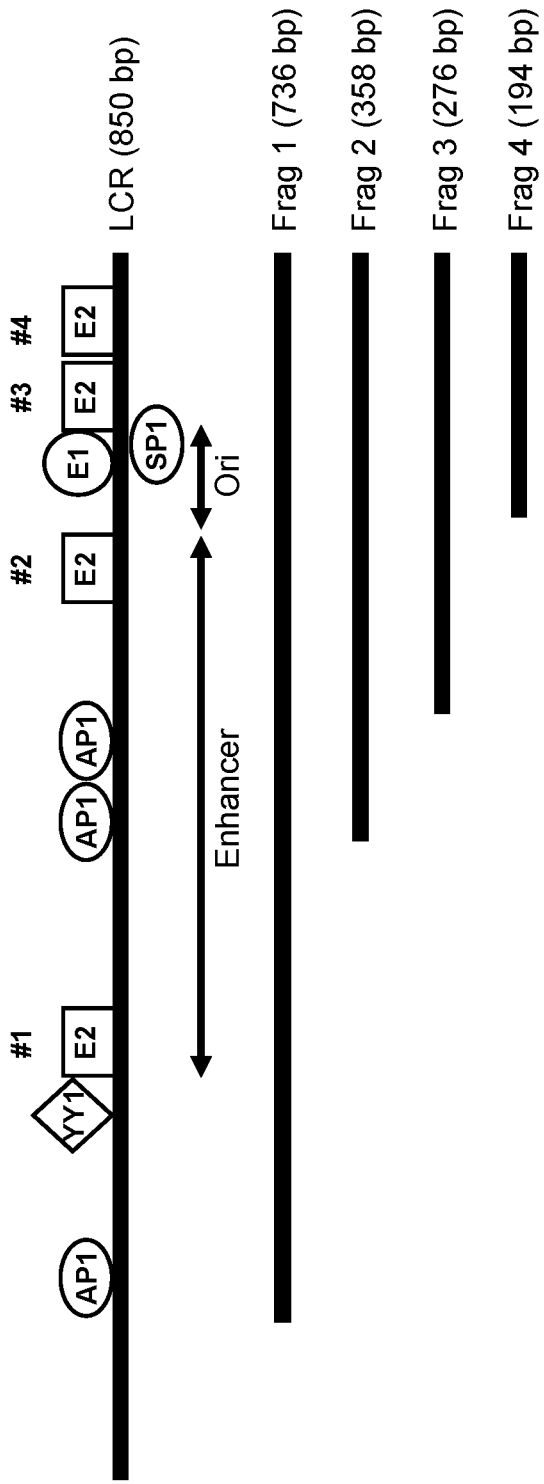
FIG. 11 depicts the genomic relationship between Frag 1, Frag 2, Frag 3, and Frag 4 of the LCR of HPV16.
Figure 12:
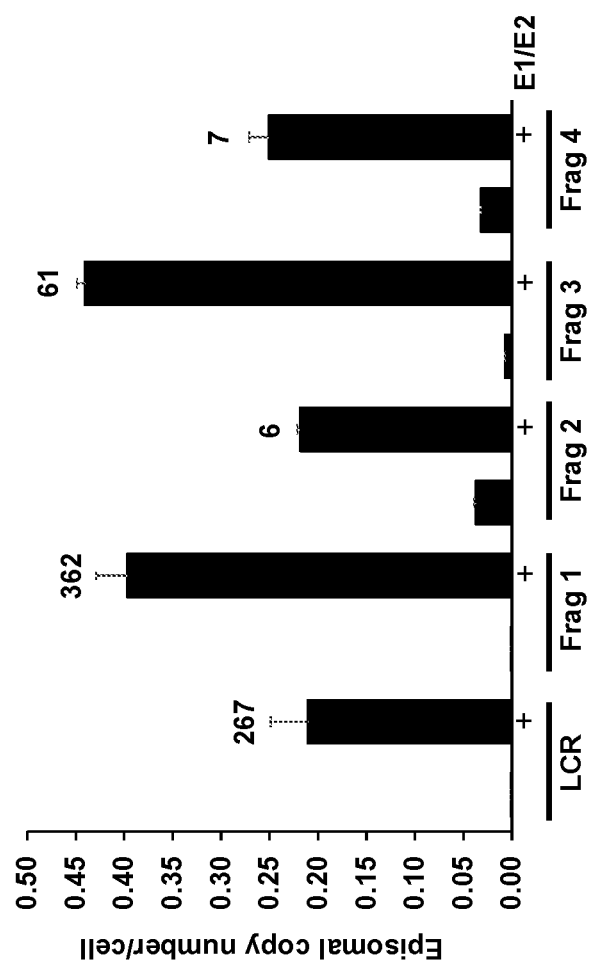
FIG. 12 depicts an analysis of episomal copy number of the HPV16 ori in an integrase-deficient lentiviral vector as described herein.

The heterologous viral episomal origin of DNA replication may be from a human papillomavirus type 16 (HPV16). The heterologous viral episomal origin of DNA replication may be from a long control region (LCR) of HPV16. The heterologous viral episomal origin of DNA replication may include SEQ ID NO: 1. Optionally, the heterologous viral episomal origin of DNA replication may include a 5' truncation of SEQ ID NO: 1. The heterologous viral episomal origin of DNA replication may include a 5' truncation of at least about 200 nucleotides, or at least about 300 nucleotides, or at least about 400 nucleotides, or at least about 500 nucleotides, or at least about 600 nucleotides, or at least about 700 nucleotides of SEQ ID NO: 1. The heterologous viral episomal origin of DNA replication may include at least about 80% sequence identity, or at least about 85% sequence identity, or at least about 90% sequence identity, or at least about 95% sequence identity, or at least about 98% sequence identity with Frag 1 (SEQ ID NO: 2), or Frag 2 (SEQ ID NO: 3), or Frag 3 (SEQ ID NO: 4), or Frag 4 (SEQ ID NO: 5) of the LCR of HPV16. The heterologous viral episomal origin of DNA replication may include Frag 1 (SEQ ID NO: 2), or Frag 2 (SEQ ID NO: 3), or Frag 3 (SEQ ID NO: 4), or Frag 4 (SEQ ID NO: 5) of the LCR of HPV16. Without limiting any of the foregoing or the Examples detailed herein, the genomic organization of the LCR is depicted in FIG. 11. In addition to the fragments detailed herein, additional fragments can be created by deletion 5' and 3' regions of the LCR. Further, mutations, substitutions, additions and/or deletions can be made to the full-length LCR or associated fragments. Further, and without limiting the foregoing or the Examples detailed herein, it is understood and within the scope of the embodiments of this invention that components of the vectors detailed herein can be used interchangeably to develop new and/or modified vectors.

Figure 21:
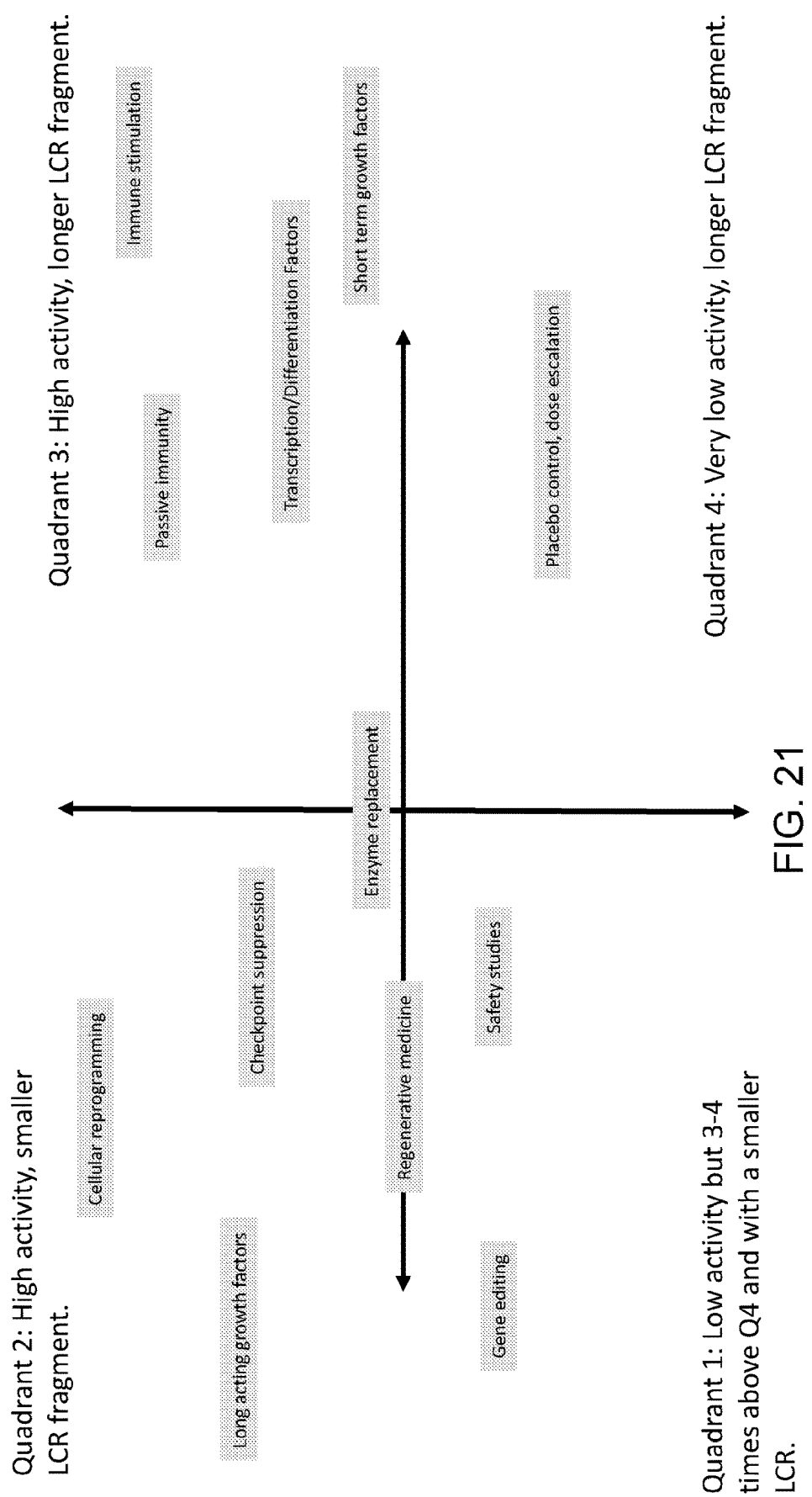
FIG. 21 depicts an embodiment for selection of LCR fragment selection based on findings of relative structure-function activity as further described in Examples detailed herein.

The LCR fragments detailed herein can be selected and used depending on a disease target. As shown in FIG. 21 and in Table 1, depending on the disease target of interest, a LCR fragment correlating to a particular Quadrant (see: FIG. 21) can be selected.

TABLE 1

Summary of Disease Targets and Related Description

| Disease Target or Property | Description |
|---|---|
| Regenerative Medicine | Therapy for chronic degenerative neurological or systemic diseases. |
| Cellular reprogramming | Release of exosomal vesicles or regulatory proteins that control local microenvironments. |
| Long acting growth factors | Protein or peptide factors that are required to sustain tissue function or integrity. |
| Checkpoint suppression | Modulating the immune checkpoint system to increase immunity or decrease tumor or infected cells. |
| Enzyme replacement | Short-term delivery of a required growth factor that might be needed to bridge an existing regimen or test the suitability of replacing protein injection with DNA delivery. |
| Immune stimulation | Protein, peptide, regulatory RNA or other cellular modifications required to activate and/or direct an immune response. This may include expression of cytokines or introduction of chimeric antigen receptors and/or natural antigen receptors to direct cellular recognition. |
| Gene editing | CRISP, zinc finger nuclease, TALEN and other guided DNA modification systems that are used for gene editing and are not suitable for permanent or long-term expression in cells. |
| Safety studies | This broad category encompasses situations where the program objective is to introduce highly durable gene therapy such as integrating lentivirus vector, but an intermediate step is needed to assess safety of a proposed DNA construct and/or to obtain objective clinical responses justifying the introduction of a longer-lasting version of the same DNA construct. |
| Passive immunity | Transient expression of a protective antibody or antigen receptor to protect against anticipated pathogen encounters, bridge existing immunotherapies, combine with chemotherapy or radiation therapy, and to direct immunity to cancer, infectious disease, or long-term pathology that might include neurodegenerative disease or activators of autoimmunity targets. |
| Transcription/ Differentiation Factors | Cellular factors including protein, lipid, DNA and/or RNA may be needed to alter the fate of individual cells including fetal or adult stem cells where long-term expression would be detrimental to fully differentiated function or create a risk for malignant disease. |
| Short term growth factors | Protein, peptide, DNA or RNA molecules intended to stimulate cellular activity for the purposes of inducing cell growth, tissue formation, blood vessel formation, muscle growth, nerve growth, skin growth and other objective clinical responses where long term factor expression is detrimental to cell or tissue function. |
| Placebo control, dose escalation | Creates a placebo control with the same DNA cargo but extremely low expression to monitor the impact of vector delivery on clinical trial outcomes. |

Accordingly, based on the intended disease target, a vector system can be designed using Quadrant 1, Quadrant 2, Quadrant 3, or Quadrant 4 components (see: FIG. 21). Selecting Quadrant 1 components provide for transient basal expression of genetic cargo using the described vector systems. In most cases, the DNA copies numbers will be roughly 20-times below the highest levels that can be achieved with this system. Careful selection of promoters driving expression of the DNA cargo will further increase the flexibility and tissue specificity of this system. Selecting Quadrant 2 provides for high episomal DNA copy numbers with potentially very high gene expression levels again depending on promoter selection. Further, the use of shorter LCR fragments increases the size of DNA inserts that can be incorporated as cargo. Selecting Quadrant 3 also provides for high episomal copy numbers but slightly less than can be obtained in Quadrant 2. The advantage of Quadrant 3 is very low basal levels of episomal DNA making the system highly controllable by the introduction or not, of E1/E2 proteins. Selecting Quadrant 4 ensures very low expression such as might be required for a placebo control or initial dose of a dose escalation clinical trial or dosing test to establish optimal levels for a desired indication.

Accordingly, the selection process can be correlated to the LCR fragments employed herein thus rendering the disclosed systems highly adaptable depending on the disease target and the intended biological response.

The at least one initiator protein specific for the heterologous viral episomal origin of DNA replication may include E1 or an operative fragment thereof. The at least one initiator protein specific for the heterologous viral episomal origin of DNA replication may include E2 or an operative fragment thereof. The at least one initiator protein specific for the heterologous viral episomal origin of DNA replication may include EBNA-1 or an operative fragment thereof. Optionally, the system may include at least two initiator proteins specific for the heterologous viral episomal origin of replication. The at least two initiator proteins specific for the heterologous viral episomal origin of DNA replication may be E1 and E2 or operative fragments thereof. The sequence encoding the at least one initiator protein may be present on a single discrete plasmid. Optionally, the system may include at least two initiator proteins specific for the heterologous viral episomal origin of replication, wherein the sequence encoding the at least two initiator proteins may be present on a single discrete plasmid. Optionally, the system may include at least two initiator proteins specific for the heterologous viral episomal origin of replication, wherein the sequence for a first initiator protein and the sequence for a second initiator protein may be present on discrete plasmids.

In respect of the disclosed non-integrating viral delivery system, the at least one gene product may include an antibody, an antibody fragment, or a growth factor. The antibody may include an anti-HER2 antibody or a fragment thereof. The growth factor may include vascular endothelial growth factor (VEGF) or a variant thereof. The miRNA may include a CCR5 miRNA.

Methods

Aspects of the invention include methods of administering a VIV system to a patient in need thereof, wherein the VIV system encodes at least one, at least two, at least three, at least four, or at least five genes of interest. Given the versatility and therapeutic potential and the disclosed VIV system, a VIV system according to aspects of the invention may encode genes or nucleic acid sequences that include but are not limited to an antibody directed to an antigen associated with an infectious disease or a toxin produced by the infectious pathogen, platelet derived growth factor, vascular endothelial growth factor, brain derived growth factor, nerve growth factor, human growth factor, human chorionic gonadotropin, cystic fibrosis transmembrane conductance regulator (CFTR), dystrophin or dystrophin-associated complex, lipoprotein lipases, α- and/or β-thalassemias, factor VIII, bone morphogenetic proteins 1-4, cyclooxygenase 2, vascular endothelial growth factor, chemokine receptor CCR5, chemokine receptor CXCR4, chemokine receptor CXCR5, antisense DNA or RNA against autoimmune antigens involved in colitis, inflammatory bowel disease or Crohn's disease, small interfering RNA that are involved in addiction including miRNAs regulating neural attenuation to opiates or alcohol, tumor suppressor genes, genes regulating cell survival including pro- or anti-apoptosis genes and pro- or anti-autophagy genes, genes encoding radiation resistance factors, genes encoding light emitting proteins used for tracking tumor cell metastasis or other cell trafficking phenomena, or a variety of other therapeutically useful sequences that may be used to condition the body for maximum effect of radiation, surgical or chemotherapeutics or to protect tissues against radiation, surgical or chemotherapeutics, to modify the host or graft tissues to improve organ transplantation or to suppress hyperreactivity especially in the airway.

Further, and without limiting any of the foregoing, in another aspect, a method of expressing at least one gene, gene product, shRNA, siRNA, miRNA, or other RNA of interest in a cell is provided. The method includes contacting the cell with an effective amount of a non-integrating viral delivery system, wherein the system includes a viral carrier, wherein the viral carrier contains a defective integrase gene; a heterologous viral episomal origin of replication; a sequence encoding at least one initiator protein specific for the heterologous viral episomal origin of replication, wherein expression of the sequence encoding the at least one initiator protein specific for the heterologous viral episomal origin of DNA replication is inducible; and at least one gene, gene product, shRNA, siRNA, miRNA, or other RNA of interest.

In another aspect, a method of expressing at least one gene, gene product, shRNA, siRNA, miRNA, or other RNA of interest in a subject in need thereof is provided. The method includes administering to the subject in need thereof an effective amount of a non-integrating viral delivery system, wherein the system includes a viral carrier, wherein the viral carrier contains a defective integrase gene; a heterologous viral episomal origin of replication; a sequence encoding at least one initiator protein specific for the heterologous viral episomal origin of replication, wherein expression of the sequence encoding the at least one initiator protein specific for the heterologous viral episomal origin of DNA replication is inducible; and at least one gene, gene product, shRNA, siRNA, miRNA, or other RNA of interest. The sequence encoding the at least one initiator protein may be present on a single discrete plasmid, and the at least one initiator protein may be either of E1 or E2, alone or in combination, or fragments thereof. The method optionally includes administering to the subject in need thereof a first amount of the single discrete plasmid to initiate a first level of expression of the at least one gene, gene product, shRNA, siRNA, miRNA, or other RNA of interest. The method optionally includes administering to the subject in need thereof a second amount of the single discrete plasmid to initiate a second level of expression of the at least one gene, gene product, shRNA, siRNA, miRNA, or other RNA of interest. In situations when the second amount is lower than the first amount, the level of expression of the at least one gene, gene product, shRNA, siRNA, miRNA, or other RNA of interest may be reduced. In situations when the second amount is higher than the first amount, the level of expression of the at least one gene, gene product, shRNA, siRNA, miRNA, or other RNA of interest may be increased.

Infectious Disease

Methods of treating or preventing infectious disease are provided. Prophylactic delivery of monoclonal antibodies to high risk individuals is presently practiced, such as individuals at high risk of contracting an infectious disease, due to health status or geographic location. The prophylactic delivery includes delivery protective antibodies against a lethal viral agent, such as to protect individuals moving through an endemic region (e.g., military and aid workers entering an Ebola-infected region). Vaccines are largely untested for diseases such as Ebola or Lassa Fever virus or Dengue fever or Chikungunya virus or *Plasmodium* spp. causing malaria, and chronic expression of prophylactic antibody genes through the use of integrating vectors carries unknown health risks. Thus, there is a significant medical need for effective antibody expression that must be high but transient.

The disclosed VIV system and methods of delivering high copy numbers of a gene, gene product, shRNA, siRNA, miRNA, and/or other gene-silencing RNA of interest for a limited period satisfy this medical need. A non-limiting example of a gene product that can be delivered for treating an infectious disease is an antibody specific for the infectious disease in question.

In one aspect, the invention is directed to methods of treating, preventing, or minimizing conditions, symptoms, or side effects associated with infectious disease. In certain embodiments, the infectious disease can be human immunodeficiency virus (HIV), human T cell leukemia virus, Ebola virus, Lassa fever virus, dengue fever, Zika virus, malaria, tuberculosis, rabies, vaccinia virus or other infectious diseases. In some embodiments, a VIV system can be administered prophylactically or following infection with an infectious disease.

In another aspect, a VIV system can be used to prevent an infectious disease. Subjects suspected of having an increased risk of contracting a particular infection disease can receive administrations of a prophylactically effective amount of a VIV encoding an antibody that specifically targets the infectious disease in question.

In certain embodiments, the infectious disease can be human immunodeficiency virus (HIV), human T cell leukemia virus, Ebola virus, Lassa fever virus, dengue fever, Zika virus, malaria, tuberculosis, rabies, vaccinia virus or other infectious diseases. In certain embodiments, a VIV vector can be administered prophylactically or following infection with an infectious disease.

Wound Healing

In another embodiment, the invention is directed to methods of treating, preventing, or minimizing conditions, symptoms, or side effects associated with wound healing. The disclosed composition can be administered systemically or directly to a wound after an accident, injury, or surgery. In the case of surgery, a VIV system may be administered prophylactically in order to expedite healing. In the case of a wound from an accident, injury, or surgery, a VIV system may be administered sometime after the formation of the wound. For instance, the VIV system may be administered within about 1, about 2, about 3, about 4, about 5, about 10, about 12, about 24, about 36, about 48, about 60, about 72, about 84, about 96, about 108, about 120, or about 168 hours of the formation of a wound.

Another application of the methods and compositions of the invention is transient delivery of VIV constructs capable of expressing platelet growth factor that would accelerate wound healing. A high dose of platelet-derived growth factor (PDGF), related growth factors, fragments thereof, and nucleotide mutants related thereto is required very quickly but transiently. The disclosed system and methods are ideal for this type of application.

Additional short-term applications include expression of brain-derived growth factor for intermittent treatment of alcohol abuse, nerve growth factor for spinal cord regeneration, and topical applications for skin conditions.

Bone Disease or Injury

In one embodiment, the disclosed invention is directed to a method of enhancing bone healing, comprising identifying a subject with a bone injury and administering to the subject a therapeutically effective amount of a viral delivery system according to the invention. The viral delivery system comprises a viral carrier, a heterologous viral episomal origin of replication, a sequence encoding an initiator protein specific for the heterologous viral episomal origin of replication, and at least one gene, gene product, shRNA, siRNA, miRNA, and/or other gene-silencing RNA of interest, wherein the viral carrier has a defective integrase gene, and wherein expression of the sequence encoding the initiator protein specific for the heterologous viral episomal origin of DNA replication is under the control of an inducible promoter. The bone injury can be, for example, resulting from an accident, injury, or surgery and may be bone nonunion, or acute fracture or required spinal fusion. In some embodiments, the gene, gene product, shRNA, siRNA, miRNA, and/or other gene-silencing RNA of interest encodes bone morphogenetic proteins 1-4 or cyclooxygenase-2 or vascular endothelial growth factor, or fragments thereof. Further, in certain embodiments mutants of the foregoing are preferable and are within the scope of the invention for treating a bone injury or related disease.

In one embodiment, the disclosed invention is directed to a method of enhancing bone healing, comprising identifying a subject with a bone disease and administering to the subject a therapeutically effective amount of a viral delivery system according to the invention. The viral delivery system comprises a viral carrier, a heterologous viral episomal origin of replication, a sequence encoding an initiator protein specific for the heterologous viral episomal origin of replication, and at least one gene, gene product, shRNA, siRNA, miRNA, and/or other gene-silencing RNA of interest, wherein the viral carrier has a defective integrase gene, and wherein expression of the sequence encoding the initiator protein specific for the heterologous viral episomal origin of DNA replication is under the control of an inducible promoter. The bone disease can be, for example, resulting from an accident, injury, or surgery and may be bone nonunion, or acute fracture or required spinal fusion. Additionally, the bone disease may be from low bone density, low blood flow to the bone, aging, hereditary conditions, and the like. In some embodiments, the gene, gene product, shRNA, siRNA, miRNA, and/or other gene-silencing RNA of interest encodes bone morphogenetic proteins 1-4 or cyclooxygenase-2 or vascular endothelial growth factor.

Hereditary Genetic Disease

TABLE 2

Summary of Hereditary Genetic Diseases and Implicated Genetic Factors

| Disorder | Mutation | Chromosome |
| --- | --- | --- |
| 22q11.2 deletion syndrome | D | 22q |
| Alpha-1-anti-trypsin disorder | P | 14q32 |
| 14q32 Angelman syndrome | | |
| Canavan disease | | 17p |
| Charcot-Marie-Tooth disease | | |
| Color blindness | P | X |
| Cri du chat | D | 5 |
| Cystic fibrosis | P | 7q |
| Down syndrome | C | 21 |
| Duchenne muscular dystrophy | D | Xp |
| Haemochromatosis | P | 6 |
| Haemophilia | P | X |

TABLE 2-continued

Summary of Hereditary Genetic Diseases and Implicated Genetic Factors

| Disorder | Mutation | Chromosome |
| --- | --- | --- |
| Klinefelter syndrome | C | X |
| Neurofibromatosis |  | 17q/22q/? |
| Phenylketonuria | P | 12q |
| Polycystic kidney disease | P | 16 (PKD1) or 4 (PKD2) |
| Prader-Willi syndrome | DC | 15 |
| Sickle-cell disease | P | 11p |
| Tay-Sachs disease | P | 15 |
| Turner syndrome | C | X |

In another embodiment, the invention is directed to methods of treating, preventing, or minimizing conditions, symptoms, or side effects associated with a hereditary genetic disease. Several examples of such hereditary genetic diseases are disclosed in Table 2 herein, along with the causal type of mutation and chromosome involved using the nomenclature below:

P—Point mutation, or any insertion/deletion entirely inside one gene

D—Deletion of a gene or genes

C—Whole chromosome extra, missing, or both (see Chromosome abnormality)

T—Trinucleotide repeat disorders: gene is extended in length

Current gene therapy includes efforts to edit genomic DNA through gene deletion, replacement, or re-sequencing. Various gene therapy systems known in the art, including Talen, CRISPR-Cas9, zinc finger endonuclease, TALEN, and others, rely on delivery of genetic material by lentivirus transduction. But, unlike the disclosed invention, these systems may have unexpected consequences if left active in cells for extended periods because active chromosome modification systems may alter unexpected sites, leading to new genetic diseases including cancer. Truly practical systems for modification of host DNA require transient, well-regulated expression through methods such as the method disclosed herein.

Thus, in one embodiment, the disclosed invention is directed to a method of treating a hereditary genetic disease, comprising identifying a subject with a hereditary genetic disease and administering to the subject a therapeutically effective amount of a viral delivery system according to the invention. The viral delivery system comprises a one or more of a viral carrier, a heterologous viral episomal origin of replication, a sequence encoding an initiator protein specific for the heterologous viral episomal origin of replication, and at least one gene, gene product, shRNA, siRNA, miRNA, and/or other gene-silencing RNA of interest, wherein the viral carrier has a defective integrase gene, and wherein expression of the sequence encoding the initiator protein specific for the heterologous viral episomal origin of DNA replication is under the control of an inducible promoter. The hereditary genetic disease can be, for example, the diseases listed in Table 2, and in some embodiments, the gene, gene product, shRNA, siRNA, miRNA, and/or other gene-silencing RNA of interest encodes non-mutated versions of the genes listed in Table 2. Without limiting the foregoing, the specific hereditary genetic disease can be CF and treatment can be pursued by expressing a non-mutated form of CFTR as detailed herein.

In another embodiment, a guide RNA target sequence is incorporated into the disclosed VIV system. Guide RNA are sequences used to target gene editing machinery to specific sites within the host genome that are mutated or otherwise require correction. Inclusion of guide RNA within the cargo of a VIV system allows for a modification of a section of a chromosome that requires correction, and the same modification will occur within VIV to accelerate degradation and/or dilution by the host. In certain embodiments of the invention, the disclosed viral delivery system comprises one or more of a viral carrier, a heterologous viral episomal origin of replication, a sequence encoding an initiator protein specific for the heterologous viral episomal origin of replication, at least one gene, shRNA, siRNA, miRNA, and/or other gene-silencing RNA of interest, and at least one guide RNA, wherein the viral carrier has a defective integrase gene, and wherein expression of the sequence encoding the initiator protein specific for the heterologous viral episomal origin of DNA replication is under the control of an inducible promoter.

Ex Vivo Modification of Cells or Tissues

In another aspect, the VIV system may be used to modify cells or tissues that are used for disease therapy. Cells may include, without limitation, primary cells such as lymphocytes, stem cells, epithelial cells, neural cells and others. For example, the VIV system may be used to modify lymphocytes that are redirected to specific disease including cancer, infectious disease or autoimmunity, and where long-term presence of genetically modified cells poses a health risk. For example, a VIV system may also be used to program pluripotent stem cells that require high levels of transcript factors for a defined interval and where the long-term presence of an integrated viral vector is undesirable. Suitable epithelial cells include those used for synthetic skin or other applications. These may require the expression of trophic or growth factors during the initial treatment that would be deleterious to function of the normal tissue after treatment and are best delivered by the VIV systems disclosed herein.

Doses and Dosage Forms

The disclosed VIV systems allow for short, medium, or long-term expression of genes or sequences of interest and episomal maintenance of the disclosed vectors. Accordingly, dosing regimens may vary based upon the condition being treated and the method of administration.

In one embodiment, VIVs may be administered to a subject in need in varying doses. Specifically, a subject may be administered $\geq 10^6$ infectious doses (where 1 dose is needed on average to transduce 1 target cell). More specifically, a subject may be administered $\geq 10^7$, $\geq 10^8$, $\geq 10^9$, or $\geq 10^{10}$ infectious doses. Upper limits of VIV dosing will be determined for each disease indication and will depend on toxicity/safety profiles for each individual product or product lot.

Additionally, VIVs may be administered once or twice a day. Alternatively, VIVs may be administered to a subject in need once a week, once every other week, once every three weeks, once a month, every other month, every three months, every six months, every nine months, once a year, every eighteen months, every two years, every 36 months, or every three years or more.

In various aspects and embodiments, VIVs are administered as a pharmaceutical composition. In embodiments, the pharmaceutical composition comprising VIV can be formulated in a wide variety of nasal, pulmonary, oral, topical, or parenteral dosage forms for clinical application. Each of the dosage forms can contain various disintegrating agents, surfactants, fillers, thickeners, binders, diluents such as wetting agents or other pharmaceutically acceptable excipients. The pharmaceutical composition comprising a VIV can also be formulated for injection.

The VIV composition can be administered using any pharmaceutically acceptable method, such as intranasal, buccal, sublingual, oral, rectal, ocular, parenteral (intravenously, intradermally, intramuscularly, subcutaneously, intracisternally, intraperitoneally), pulmonary, intravaginal, locally administered, topically administered, topically administered after scarification, mucosally administered, via an aerosol, or via a buccal or nasal spray formulation.

Further, the VIV composition can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, and a suspension. Further, the composition may be a controlled release formulation, sustained release formulation, immediate release formulation, or any combination thereof. Further, the composition may be a transdermal delivery system.

In another embodiment, the pharmaceutical composition comprising a VIV can be formulated in a solid dosage form for oral administration, and the solid dosage form can be powders, granules, capsules, tablets or pills. In yet another embodiment, the solid dosage form can include one or more excipients such as calcium carbonate, starch, sucrose, lactose, microcrystalline cellulose or gelatin. In addition, the solid dosage form can include, in addition to the excipients, a lubricant such as talc or magnesium stearate. In some embodiments, the oral dosage form can be immediate release, or a modified release form. Modified release dosage forms include controlled or extended release, enteric release, and the like. The excipients used in the modified release dosage forms are commonly known to a person of ordinary skill in the art.

In a further embodiment, the pharmaceutical composition comprising a VIV can be formulated as a sublingual or buccal dosage form. Such dosage forms comprise sublingual tablets or solution compositions that are administered under the tongue and buccal tablets that are placed between the cheek and gum.

In yet a further embodiment, the pharmaceutical composition comprising a VIV can be formulated as a nasal dosage form. Such dosage forms of the present invention comprise solution, suspension, and gel compositions for nasal delivery.

In one embodiment, the pharmaceutical composition can be formulated in a liquid dosage form for oral administration, such as suspensions, emulsions or syrups. In other embodiments, the liquid dosage form can include, in addition to commonly used simple diluents such as water and liquid paraffin, various excipients such as humectants, sweeteners, aromatics or preservatives. In particular embodiments, the composition comprising VIV or a pharmaceutically acceptable salt thereof can be formulated to be suitable for administration to a pediatric patient.

In one embodiment, the pharmaceutical composition can be formulated in a dosage form for parenteral administration, such as sterile aqueous solutions, suspensions, emulsions, non-aqueous solutions or suppositories. In other embodiments, the non-aqueous solutions or suspensions can include propyleneglycol, polyethyleneglycol, vegetable oils such as olive oil or injectable esters such as ethyl oleate. As a base for suppositories, witepsol, macrogol, tween 61, cacao oil, laurin oil or glycerinated gelatin can be used.

The dosage of the pharmaceutical composition can vary depending on the patient's weight, age, gender, administration time and mode, excretion rate, and the severity of disease.

Definitions

Words that are not specifically defined herein will be understood to have a meaning consistent with that as understood by persons of ordinary skill in the art.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The terms "administration of" or "administering" an active agent means providing an active agent of the invention to the subject in need of treatment in a form that can be introduced into that individual's body in a therapeutically useful form and therapeutically effective amount.

The terms, "expression," "expressed," or "encodes" refer to the process by which polynucleotides are transcribed into mRNA and/or the process by which the transcribed mRNA is subsequently being translated into peptides, polypeptides, or proteins. Expression may include splicing of the mRNA in a eukaryotic cell or other forms of post-transcriptional modification or post-translational modification.

The terms "individual," "host," "subject," and "patient" are used interchangeably herein.

The term "therapeutically effective amount" refers to a sufficient quantity of the active agents of the present invention, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

The term "treatment" or "treating" generally refers to an intervention in an attempt to alter the natural course of the subject being treated, and can be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis.

As used herein, the term "VIV" refers to a vector-in-vector system for expressing at least one gene, gene product, shRNA, siRNA, miRNA, or other RNA of interest. The term "VIV" is used synonymously with viral delivery system, when used herein.

The following examples are given to illustrate aspects of the present invention. It should be understood, however, that the invention is not to be limited to the specific conditions or details described in these examples. All printed publications referenced herein are specifically incorporated by reference.

EXAMPLES

Example 1—VIV for Treating an Infectious Disease

This example demonstrates an exemplary VIV construct for treating an infectious disease.

In this example, FIG. 1A represents an exemplary linear VIV construct for treating Ebola virus, an infectious disease. Herein, at least one of the "cargo" portions depicted in FIG. 1A encodes an antibody that specifically targets Ebola virus. The long terminal repeat (LTR) portions of the exemplary VIV construct can be used to circularize the viral nucleic acid, as shown in FIG. 1B.

Subjects suspected of having or diagnosed as having Ebola virus can receive administrations of a therapeutically effective amount of a VIV encoding an antibody that specifically targets Ebola virus, either alone or in combination with one or more additional agents for the treatment or prevention of Ebola. VIV encoding an antibody that specifically targets Ebola virus and/or additional agents are administered orally, intranasally, intrathecally, intraocularly, intradermally, transmucosally, iontophoretically, topically, systemically, intravenously, subcutaneously, intraperitoneally, or intramuscularly according to methods known in the art or as described herein. Subjects are then evaluated daily for the presence and/or severity of signs and symptoms associated with Ebola virus, including, but not limited to, e.g., fever, fatigue, malaise, weakness, reddened eyes, joint and muscle pain, headache, nausea, vomiting, hemorrhage, and death. Treatments are maintained until such a time as one or more signs or symptoms of Ebola virus infection are ameliorated or eliminated.

It is rationally predicted that subjects suspected of having or diagnosed as having been infected with Ebola virus and receiving therapeutically effective amounts of a VIV encoding an antibody that specifically targets Ebola virus, will display reduced severity or elimination of one or more symptoms associated with Ebola virus infection. It is further rationally predicted that administration of a VIV encoding an antibody that specifically targets Ebola virus in combination with one or more additional agents will have synergistic effects.

These results will show that VIV encoding an antibody that specifically targets Ebola virus is useful in the treatment of Ebola virus.

Example 2—VIV for Preventing an Infectious Disease

This example demonstrates an exemplary VIV construct for preventing an infectious disease.

In this example, FIG. 1A represents an exemplary linear VIV construct for preventing infection with Ebola virus, an infectious disease. Herein, at least one of the "cargo" portions depicted in FIG. 1A encodes an antibody that specifically targets Ebola virus. The long terminal repeat (LTR) portions of the exemplary VIV construct can be used to circularize the viral nucleic acid, as shown in FIG. 1B.

Subjects suspected of having an increased risk of contracting Ebola virus can receive administrations of a prophylactically effective amount of a VIV encoding an antibody that specifically targets Ebola virus, either alone or in combination with one or more additional agents for the treatment or prevention of Ebola prior to entering an area in which risk of contracting Ebola is increased. VIV encoding an antibody that specifically targets Ebola virus and/or additional agents are administered orally, intranasally, intrathecally, intraocularly, intradermally, transmucosally, iontophoretically, topically, systemically, intravenously, subcutaneously, intraperitoneally, or intramuscularly according to methods known in the art or as described herein. Subjects are then evaluated daily for the presence and/or severity of signs and symptoms associated with Ebola virus, including, but not limited to, e.g., fever, fatigue, malaise, weakness, reddened eyes, joint and muscle pain, headache, nausea, vomiting, hemorrhage, and death. Treatments are maintained until such a time as one or more signs or symptoms of Ebola virus infection are prevented.

It is rationally predicted that subjects suspected of having or diagnosed as having been exposed to Ebola virus and receiving prophylactically effective amounts of a VIV encoding an antibody that specifically targets Ebola virus, will have a reduced risk of contracting Ebola. It is further rationally predicted that administration of VIV encoding an antibody that specifically targets Ebola virus in combination with one or more additional agents will have synergistic effects.

These results will show that VIV encoding an antibody that specifically targets Ebola virus is useful in the prevention of Ebola virus.

Example 3—VIV for Enhancing Wound Healing

This example demonstrates an exemplary VIV construct for enhancing wound healing.

In this example, FIG. 1A represents an exemplary linear VIV construct for enhancing wound healing. Herein, at least one of the "cargo" portions depicted in FIG. 1A encodes platelet-derived growth factor (PDGF) (SEQ ID NO: 17). The long terminal repeat (LTR) portions of the exemplary VIV construct can be used to circularize the viral nucleic acid, as shown in FIG. 1B.

Subjects with a wound (e.g., from accident, injury, or surgery) can receive administrations of a therapeutically effective amount of a VIV encoding platelet-derived growth factor (PDGF), alone or in combination with one or more additional agents for treating or sterilizing a wound. VIV PDGF and/or additional agents are administered orally, intranasally, intrathecally, intraocularly, intradermally, transmucosally, iontophoretically, topically, systemically, intravenously, subcutaneously, intraperitoneally, or intramuscularly according to methods known in the art or as described herein. Subjects are then evaluated daily to determine the status of the wound. Treatments are maintained until such a time as the wound is healed and scarring is minimized.

It is rationally predicted that subjects with a wound and receiving therapeutically effective amounts of a VIV PDGF will display enhanced wound healing. It is further rationally predicted that administration of VIV encoding PDGF in combination with one or more additional agents will have synergistic effects.

These results will show that VIV encoding PDGF is useful for enhancing wound healing.

Example 4—VIV for Treating Bone Injury

This example demonstrates an exemplary VIV construct for treating a bone injury.

In this example, FIG. 1A represents an exemplary linear VIV construct for treating a bone injury. Herein, at least one of the "cargo" portions shown in FIG. 1A encodes bone morphogenetic protein (BMP) (SEQ ID NO: 18). The long terminal repeat (LTR) portions of the exemplary VIV construct can be used to circularize the viral nucleic acid, as shown in FIG. 1B.

Subjects suspected of having or diagnosed as having a bone injury can receive administrations of a therapeutically effective amount of a VIV encoding bone morphogenetic protein (BMP), alone or in combination with one or more additional agents for the treatment of the bone injury. VIV encoding BMP and/or additional agents are administered orally, intranasally, intrathecally, intraocularly, intradermally, transmucosally, iontophoretically, topically, systemically, intravenously, subcutaneously, intraperitoneally, or intramuscularly according to methods known in the art or as described herein. Subjects are then evaluated weekly for the presence and/or severity of signs and symptoms associated with the bone injury to determine the rate and strength of healing. Treatments are maintained until such a time as the bone has healed.

It is rationally predicted that subjects suspected of having or diagnosed as having a bone injury and receiving therapeutically effective amounts of a VIV encoding BMP will display reduced severity of injury and enhanced healing. It is further rationally predicted that administration of VIV encoding BMP in combination with one or more additional agents will have synergistic effects.

These results will show that VIV encoding BMP is useful in the treatment of bone injuries or diseases.

Example 5—VIV for Treating a Hereditary Disease

This example demonstrates an exemplary VIV construct for treating cystic fibrosis (CF).

In this example, FIG. 1A represents an exemplary linear VIV construct for treating CF, a hereditary disease. Herein, at least one of the "cargo" portions depicted in FIG. 1A encodes cystic fibrosis transmembrane conductance regulator (CFTR) (NM_000492). The long terminal repeat (LTR) portions of the exemplary VIV construct can be used to circularize the viral nucleic acid, as shown in FIG. 1B.

Subjects suspected of having or diagnosed as having (CF) can receive administrations of a therapeutically effective amount of a VIV encoding cystic fibrosis transmembrane conductance regulator (CFTR), alone or in combination with one or more additional agents for the treatment of CF. VIV encoding CFTR and/or additional agents are administered orally, intranasally, intrathecally, intraocularly, intradermally, transmucosally, iontophoretically, topically, systemically, intravenously, subcutaneously, intraperitoneally, or intramuscularly according to methods known in the art or as described herein. Subjects are then evaluated weekly for the presence and/or severity of signs and symptoms associated with CF, including, but not limited to, e.g., poor growth, persistent cough, thick sputum and mucus, wheezing, breathlessness, decreased ability to exercise, repeated lung infections, inflamed nasal passage, greasy stools, intestinal blockage, and poor weight gain. Treatments are maintained until such a time as one or more signs or symptoms of CF are ameliorated or eliminated.

It is rationally predicted that subjects suspected of having or diagnosed as having CF and receiving therapeutically effective amounts of a VIV encoding CFTR will display reduced severity or elimination of one or more symptoms associated with CF. It is further rationally predicted that administration of VIV encoding CFTR in combination with one or more additional agents will have synergistic effects.

These results will show that VIV encoding CFTR is useful in the treatment of CF.

Example 6—VIV Containing E1 to Express Cargo

A vector according to FIG. 2 was produced containing green fluorescent protein gene (GFP) as the cargo. DNA containing the complete Locus Control Region and E1 protein from human papillomavirus type 16 (NCBI accession number U89348; SEQ ID NO: 19) was chemically synthesized. Individual segments and/or coding sequences were initially synthesized. These were amplified by polymerase chain reaction (PCR) using synthetic oligonucleotide primers identical to the 5' end of green fluorescent protein gene and complementary to the 3' end of green fluorescent protein. The 5' primer (SEQ ID NO: 20) was extended from its 5' end with the recognition site for BamHI or EcoRI endonucleases. The 3' primer (SEQ ID NO: 21) was extended at its 3' end with the complement of BamHI, or EcoRI endonuclease recognition sites. The resulting amplified green fluorescent protein gene sequences were then digested with BamHI and EcoRI restriction endonucleases.

A lentiviral vector was obtained from System Biosciences, Inc. The plasmid was cleaved with BamHI and EcoRI enzymes, and mixed with excess amplified green fluorescent protein gene sequences in a 1:3 ratio of insert to vector.

Enzymatic activity was then stopped by heat inactivation at 70 degrees Celsius for 20 minutes. The above mixture was cooled to room temperature to allow annealing.

The annealing reactions were performed with bacteriophage T4 DNA ligase for 30 minutes at room temperature. 2.5 microliters of the resulting ligation mix were added to 25 microliters of STBL3 competent bacterial cells.

Transfection was then carried out by a brief (1 minute) heat-shock at 42 degrees Celsius.

Bacterial cells were streaked onto agar plates containing ampicillin to obtain bacterial cultures. These cultures were expanded in Luria broth.

To check for insertion of amplified green fluorescent protein gene sequences into the lentivirus vector packaging plasmid, DNA was extracted from the above bacterial cultures and purified by standard methods. Purified DNA was digested with the same endonucleases used to make the construct. Fragment lengths were analyzed by agarose gel electrophoresis, and the amplified green fluorescent protein gene sequences were verified by DNA sequencing using specific primers obtained from Eurofins MWG Operon LLC.

Lentivirus vector stocks were produced as follows. At least two lentiviral packaging plasmids plus the cargo plasmid were co-transfected into HEK cells where viral genes and genomic RNA are expressed, assembled into integrase-deficient lentivirus particles, and released into the culture medium. Cell-free supernatants were produced and collected during the interval of 3-10 days after transfection. Lentivirus particles were purified by standard procedures including a combination of methods that could include centrifugation, transient flow filtration, size exclusion chromatography, size exclusion filtration or ion exchange chromatography. The concentration and biological activity (transducing units per ml) for each stock were determined.

Figure 3:
FIG. 3 depicts transduction results in 293 T cells from three (3) separate experiments using Vector 1.

Mammalian cells, including 293T cells, were used to test for lentivirus-derived episome formation, copy number and expression. The 293T cells were transduced with integrase deficient lentivirus particles at a multiplicity of infection ranging from 1 to 10 in the presence of polybrene. Unabsorbed virus was removed by washing cells 3 hours after application, and cells were cultured for 3 days. Cells were observed in a fluorescence microscope and cells expressing GFP were counted. Untransduced 293 T cells were used as a negative control. Data was reported as GFP-positive cells per 100 viable cells in culture. A minimum of 300 cells were counted per microscope field and 5-10 fields were counted for each replicate experiment. Four independent transduction experiments comprising one negative control and three replicate experiments were performed to determine the frequency of transduced cells. The data is depicted in FIG. 3, and shows expression of GFP across three replicate experiments.

Example 7—VIV Containing E1 and E2 to Express Cargo

Referring to FIG. 4, Vector 19 can be constructed to contain both E1 (SEQ ID NO: 6) and E2 (SEQ ID NO: 7) initiator proteins. Here, the genetic cargo is a CMV/GFP expression cassette under the control of an inducible promoter.

293T cells can be transduced with Vector 19 at a multiplicity of infection ranging from between 1 and 20 transducing units per cell. 3 hours later, cells are washed with medium to remove unadsorbed virions and returned to culture. 12-24 hours after transduction, cells are treated with at least one dosage of a compound that can induce the inducible promoter. Upon addition of a compound that can induce the inducible promoter, E1 and E2 mRNA are transcribed from the episome and combine and assemble on the Locus Control Region Fragment 2 (LCR/F2) (SEQ ID NO: 3) to trigger DNA replication. Lentivirus-derived episomes decay starting approximately 24-36 hours after the cessation of promoter induction. Protein products from the cargo in Vector 19 are measured by analytical flow cytometry.

Example 8—Introducing E1 and E2 for Expressing Cargo

To determine the effect of E1 and E2 in expressing cargo, 293T cells were transduced with a D64V integrase-deficient lentiviral vector (i.e., vector in FIG. 5A) expressing mCherry and the full length HPV16 (SEQ ID NO: 1) long control region (LCR) or 3' fragments, as described for Fragment 1 (SEQ ID NO: 2), Fragment 2 (SEQ ID NO: 3), Fragment 3 (SEQ ID NO: 4), and Fragment 4 (SEQ ID NO: 5) herein.

Figure 5:
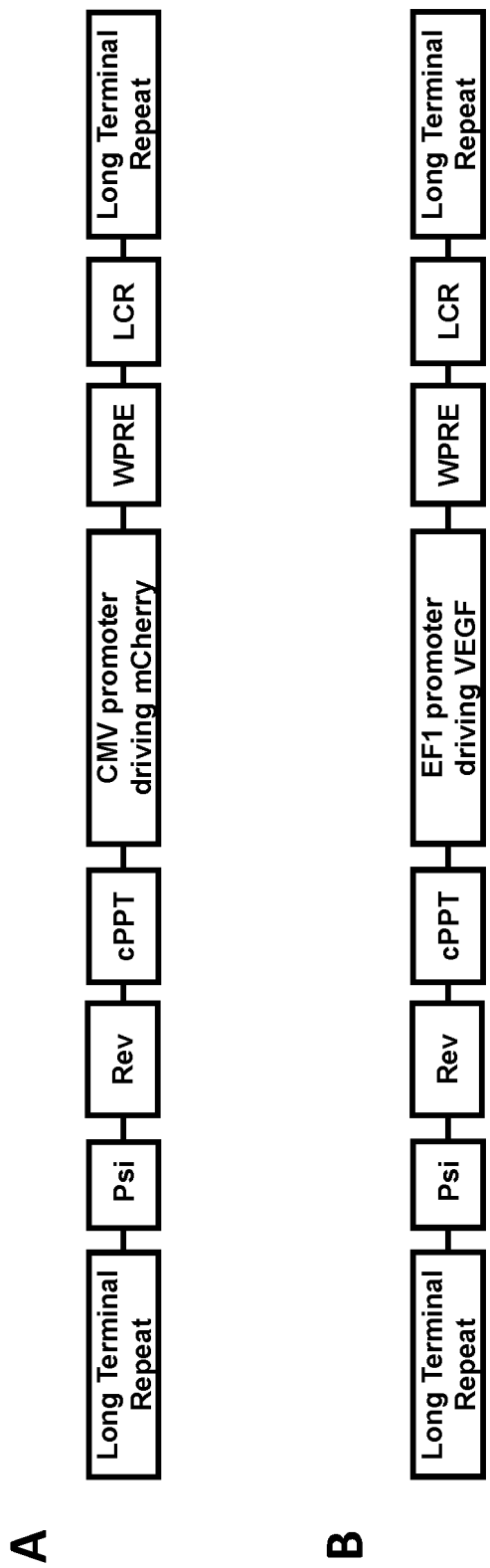
FIG. 5 depicts exemplary vector-in-vector (VIV) embodiments that express (A) mCherry and (B) VEGF, respectively.

Notably, in reference to FIG. 5A, the full length LCR or the 3' fragments were utilized in the LCR region depicted in FIG. 5A. More specifically, depictions of the designed constructs are demonstrated as Vectors 9-13 in FIG. 7 herein. Additional elements shown in FIG. 7 refer to: the psi packaging element (SEQ ID NO: 22); the rev element (SEQ ID NO: 23); the cPPT (central polypurine tract) element (SEQ ID NO: 24); and the posttranscriptional regulatory element of woodchuck hepatitis virus (WPRE) (SEQ ID NO: 25).

Figure 6:
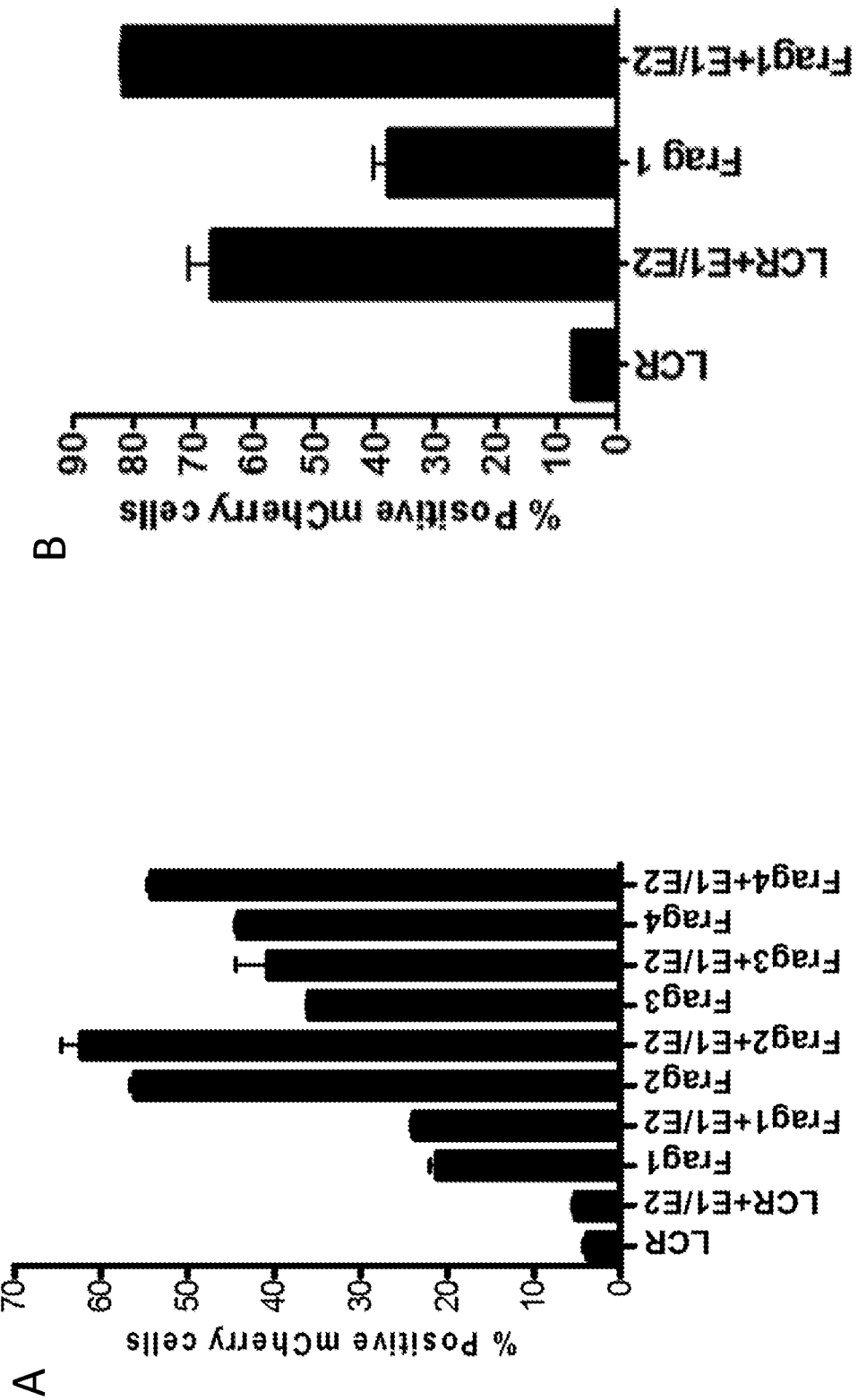
FIG. 6 depicts expression of mCherry-positive cells for variously described constructs when E1 and E2 are provided by plasmids (A) or with lentivirus (B), respectively.

After 24 hours, cells were transfected with plasmids containing HPV16 E1 (SEQ ID NO: 6) and E2 (SEQ ID NO: 7) with Lipofectamine 2000. After 2 days, mCherry expression was analyzed by FACS. The results for these experiments are depicted in FIG. 6A herein.

To contrast with the above experiments wherein E1 and E2 were introduced through plasmids, a second set of experiments were performed as described below. Briefly, 293T cells were transduced with a D64V integrase-deficient lentiviral vector expressing mCherry and the full length HPV16 long control region (LCR) (SEQ ID NO: 1) or a shorter Fragment 1 (SEQ ID NO: 2) based on the generalized vector shown in FIG. 5A herein. At the same time, cells were transduced with lentivirus expressing HPV16 E1 (SEQ ID NO: 6) and E2 (SEQ ID NO: 7). After 2 days, mCherry expression was analyzed by FACS, as shown in FIG. 6B herein. As shown in FIG. 6B herein, a greater percentage of mCherry cells was achieved when E1 and E2 were introduced with the D64V integrase-deficient lentiviral vector expressing mCherry and the full-length LCR (SEQ ID NO: 1) or the shorter fragment 1 (also referred to herein as Fragment 1, and also referred to herein as SEQ ID NO: 2).

The data detailed in this Example demonstrate that when E1 and E2 are expressed via lentiviral-mediated expression, there was stronger expression and thus more activation of HPV ori (LCR) full-length and fragments.

Secondly, the data from this Example demonstrates that there is a difference in HPV ori activation depending on the size of the LCR region. For example, with reference to FIG. 6, there was a more significant change in the expression of mCherry when using full-length LCR (SEQ ID NO: 1) and Fragment 1 (SEQ ID NO: 2), as compared with Fragments 2 (SEQ ID NO: 3), 3 (SEQ ID NO: 4), and 4 (SEQ ID NO: 5).

Example 9—Expression of VEGF

Figure 8:
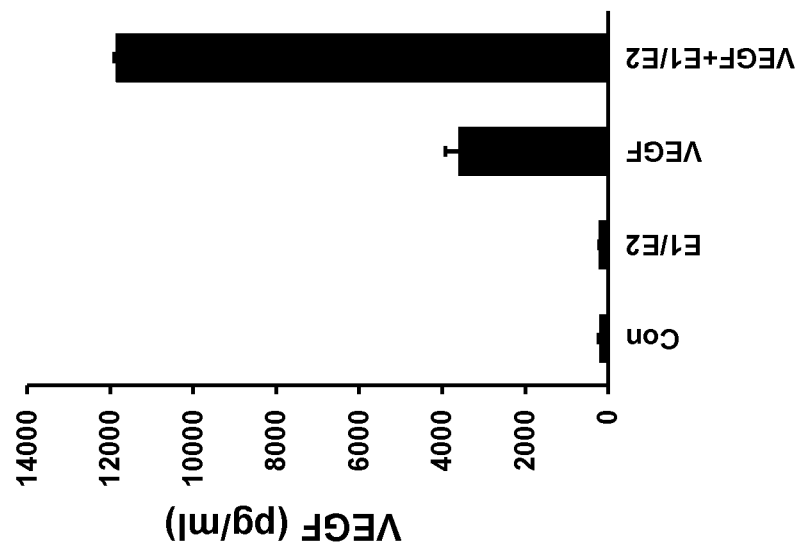
FIG. 8 depicts expression levels of VEGF for variously described constructs that contain fragment 1 of the HPV16 long control region (LCR).

As mentioned herein, VEGF can be selected to be a "cargo" region for treating, among other things, a bone injury. To further analyze the level of VEGF expression, 293T cells were transduced with a D64V integrase-deficient lentiviral vector containing a human cDNA for VEGF (SEQ ID NO: 26) and Fragment 1 (SEQ ID NO: 2) of the HPV16 long control region (LCR) (see: FIG. 5B for generalized description of VEGF-containing vector). At the same time, cells were transduced with lentiviral vectors containing HPV16 E1 (SEQ ID NO: 6) and E2 (SEQ ID NO: 7). After 2 days, cell culture media was collected and analyzed with an ELISA kit for VEGF (Thermo Scientific). As shown in FIG. 8, there was an increase in VEGF levels (3,594 pg/ml) with the VEGF expressing vector, which was further increased with E1 and E2 (11,856 pg/ml).

In a manner similar to the mCherry results from Example 8 above, the results demonstrate that there was a difference in HPV ori activation depending on the size of the LCR region. As shown in FIG. 8, there was an approximate 3-fold change in VEGF levels after adding E1/E2. Therefore, the full-length LCR (SEQ ID NO: 1) or Fragment 1 (SEQ ID NO: 2) expresses a gene of interest (i.e., VEGF) at a low level, but when E1/E2 was introduced, there was a strong induction of expression. In contrast, the other fragments tested expressed at a higher initial level and so there was a reduced difference upon introducing E1/E2.

Example 10—Development of E1 and E2-Containing Vectors

Using standard molecular biology techniques (e.g., Sambrook; Molecular Cloning: A Laboratory Manual, 4$^{th}$ Ed.) as well as the techniques described herein, a series of lentiviral vectors containing the HPV LCRs and E1 and E2 were developed as described in greater detail below. These vectors are also depicted in FIG. 9 herein.

Figure 9:
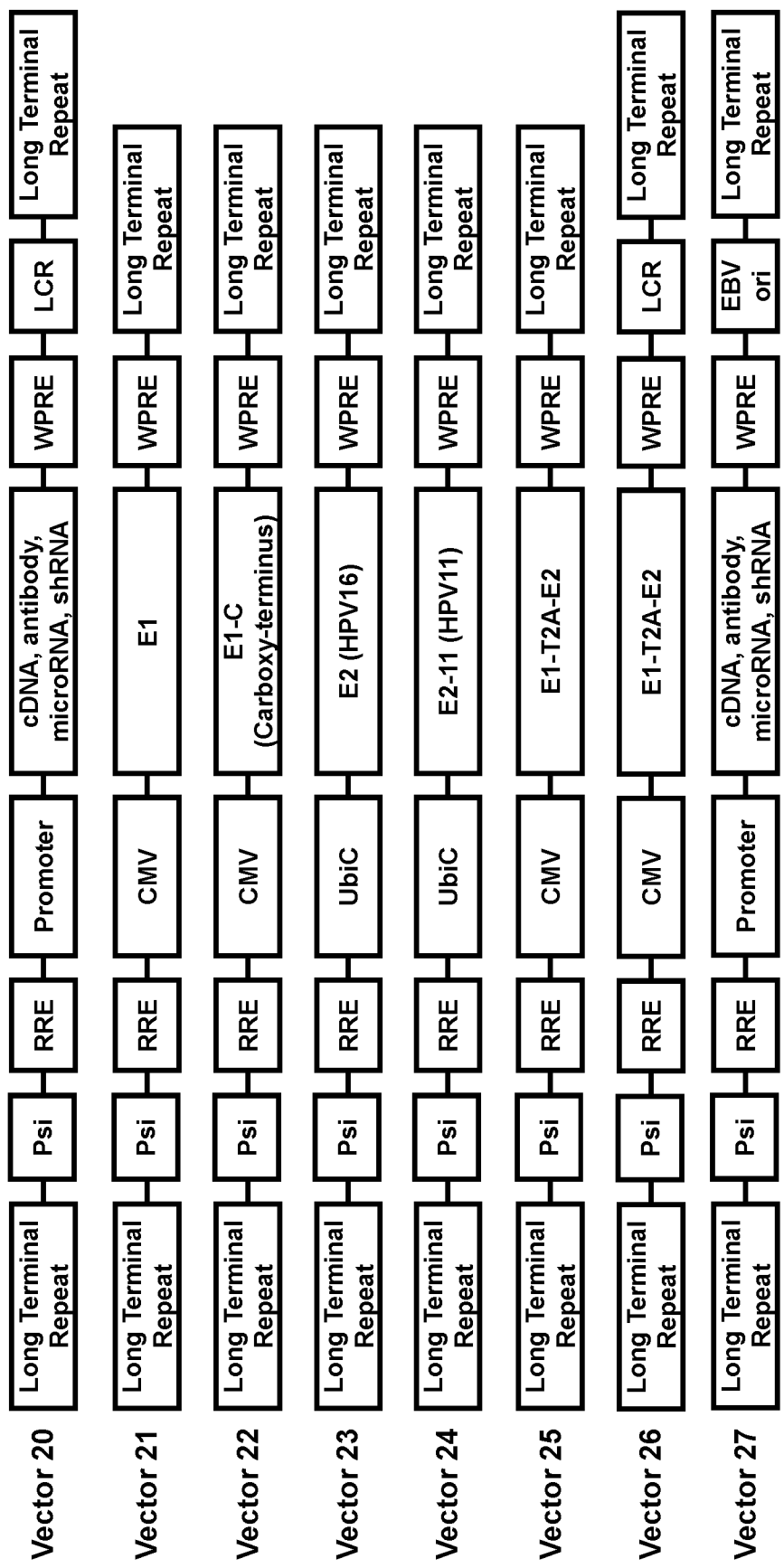
FIG. 9 depicts exemplary vector-in-vector (VIV) embodiments used in conjunction with Examples detailed herein.

Referring to FIG. 9, Vector 20 was developed and is a general lentiviral vector for expressing a cDNA, a microRNA, or a shRNA. Referring to Vector 20, and from left to right, key components of the vector as developed are: a long terminal repeat portion (SEQ ID NO: 27); a psi packaging element (SEQ ID NO: 22); a rev response element (RRE) (SEQ ID NO: 23); a promoter; a cDNA, microRNA, shRNA or other cargo element; a posttranscriptional regulatory element of woodchuck hepatitis virus (WPRE) (SEQ ID NO: 25), a LCR portion, which can contain fragments of the LCR as detailed herein; and a long terminal repeat portion (SEQ ID NO: 28).

Referring to FIG. 9, Vector 21 was developed and is a lentiviral vector for expressing E1. Referring to Vector 21, and from left to right, key components of the vector as developed are: a long terminal repeat portion (SEQ ID NO: 27); a psi packaging element (SEQ ID NO: 22); a rev response element (RRE) (SEQ ID NO: 23); a CMV promoter (SEQ ID NO: 29); E1 (SEQ ID NO: 6); a posttranscriptional regulatory element of woodchuck hepatitis virus (WPRE) (SEQ ID NO: 25); and a long terminal repeat portion (SEQ ID NO: 28).

Referring to FIG. 9, Vector 22 was developed and is a lentiviral vector for expressing E1-C (carboxy terminus) (SEQ ID NO: 8). Referring to Vector 22, and from left to right, key components of the vector as developed are: a long terminal repeat portion (SEQ ID NO: 27); a psi packaging element (SEQ ID NO: 22); a rev response element (RRE) (SEQ ID NO: 23); a CMV promoter (SEQ ID NO: 29); E1-C(SEQ ID NO: 8); a posttranscriptional regulatory element of woodchuck hepatitis virus (WPRE) (SEQ ID NO: 25); and a long terminal repeat portion (SEQ ID NO: 28).

Referring to FIG. 9, Vector 23 was developed and is a lentiviral vector for expressing E2 (HPV16) (SEQ ID NO: 7). Referring to Vector 23, and from left to right, key components of the vector as developed are: a long terminal repeat portion (SEQ ID NO: 27); a psi packaging element (SEQ ID NO: 22); a rev response element (RRE) (SEQ ID NO: 23); a UbiC promoter (SEQ ID NO: 30); E2 (HPV16) (SEQ ID NO: 7); a posttranscriptional regulatory element of woodchuck hepatitis virus (WPRE) (SEQ ID NO: 25); and a long terminal repeat portion (SEQ ID NO: 28).

Referring to FIG. 9, Vector 24 was developed and is a lentiviral vector for expressing E2-11 (HPV11) (SEQ ID NO: 9). Referring to Vector 24, and from left to right, key components of the vector as developed are: a long terminal repeat portion (SEQ ID NO: 27); a psi packaging element (SEQ ID NO: 22); a rev response element (RRE) (SEQ ID NO: 23); a UbiC promoter (SEQ ID NO: 30); E2-11 (HPV11) (SEQ ID NO: 9); a posttranscriptional regulatory element of woodchuck hepatitis virus (WPRE) (SEQ ID NO: 25); and a long terminal repeat element (SEQ ID NO: 28).

Referring to FIG. 9, Vector 25 was developed and is a lentiviral vector for expressing E1-T2A-E2 (SEQ ID NO: 10). Referring to Vector 25, and from left to right, key components of the vector as developed are: a long terminal repeat portion (SEQ ID NO: 27); a psi packaging element (SEQ ID NO: 22); a rev response element (RRE) (SEQ ID NO: 23); a CMV promoter (SEQ ID NO: 29); E1-T2A-E2 (SEQ ID NO: 10); a posttranscriptional regulatory element of woodchuck hepatitis virus (WPRE) (SEQ ID NO: 25); and a long terminal repeat portion (SEQ ID NO: 28).

Referring to FIG. 9, Vector 26 was developed and is a lentiviral vector for expressing E1-T2A-E2 (SEQ ID NO: 10) and full-length LCR (SEQ ID NO: 1) or a fragment thereof (e.g., SEQ ID NOs: 2-5). Referring to Vector 26, and from left to right, key components of the vector as developed are: a long terminal repeat portion (SEQ ID NO: 27); a psi packaging element (SEQ ID NO: 22); a rev response element (RRE) (SEQ ID NO: 23); a CMV promoter (SEQ ID NO: 29); E1-T2A-E2 (SEQ ID NO: 10); a posttranscriptional regulatory element of woodchuck hepatitis virus (WPRE) (SEQ ID NO: 25); a LCR portion, and a long terminal repeat portion (SEQ ID NO: 28).

Still referring to FIG. 9, Vector 27 depicts a general lentiviral vector for expressing, for example, a cDNA, an antibody, a microRNA, or a shRNA. Referring to Vector 27, and from left to right, key components of the vector as developed are: a long terminal repeat portion (SEQ ID NO: 27); a psi packaging element (SEQ ID NO: 22); a rev response element (RRE) (SEQ ID NO: 23); a promoter; a cDNA. microRNA, shRNA or other cargo element; a posttranscriptional regulatory element of woodchuck hepatitis virus (WPRE) (SEQ ID NO: 25); a EBV ori (SEQ ID NO: 31); and a long terminal repeat element (SEQ ID NO: 28).

Figure 10:
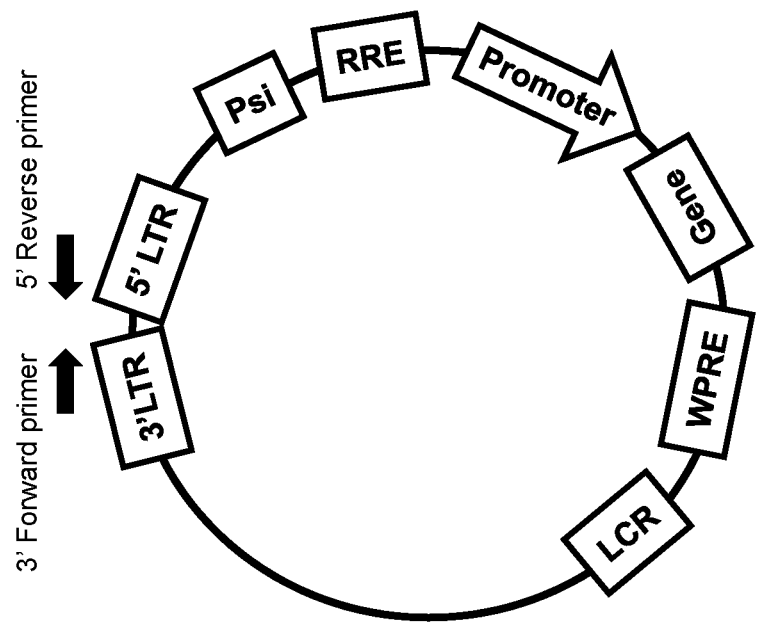
FIG. 10 depicts an exemplary diagram of an episomal form of a non-integrating lentiviral vector according to embodiments of the present invention.

The linear vectors detailed herein circularize intracellularly as shown, for example in FIG. 10, which depicts a circularization of Vector 20 (as shown in FIG. 9). For purposes of experiments detailed herein, FIG. 10 details a primer set as arrows which are located on the 3' and 5' Long Terminal Repeats (LTRs). This primer set has been designed to amplify the episomal form of the lentiviral vector, and does not amplify the integrated form of the vector. Appropriate primers for detection of lentiviral episomes contain the following sequences:

```
3'LTR Fwd
CTAATTCACTCCCAACGAAG;       (SEQ ID NO: 11)
and

5'LTR Rev
GCCGAGTCCTGCGTCGAGAG.       (SEQ ID NO: 12)
```

In the experiments detailed herein, integrase-deficient lentiviral vector copy number was regulated by a combination of utilizing Vector 20 in combination with Vector 21 or Vector 22 or Vector 23 or Vector 24. Alternately, integrase-deficient lentiviral vector copy number was regulated by a combination of utilizing Vector 20 in combination with Vector 25 or Vector 26.

Example 11—Development of LCR Fragments and Related Vectors

As discussed herein, the LCR portion of the vectors detailed herein can be and were modified through the use of fragments such as Fragment 1 (SEQ ID NO: 2), Fragment 2 (SEQ ID NO: 3), Fragment 3 (SEQ ID NO: 4); and Fragment 4 (SEQ ID NO: 5).

The genomic organization of the LCR and the fragments described herein is depicted in FIG. 11. Therein, the full-length LCR (top portion) contains a series of AP1, YY1, E1, and E2 binding sites. As shown, for example, in FIG. 11, Fragment 1 (SEQ ID NO: 2), Fragment 2 (SEQ ID NO: 3), Fragment 3 (SEQ ID NO: 4), and Fragment 4 (SEQ ID NO: 5) represent increasing LCRs with increasing 5' truncations which reduces a series of AP1, YY1, and E2 binding sites. Lentiviral vectors which make use of the LCR fragments are detailed herein (e.g., FIG. 7 and related Examples herein).

Example 12—Testing of Vectors Containing LCR Fragments and E1/E2 Variants

To test vectors containing the various LCR fragments detailed herein, 293T cells were transduced with D64V integrase-deficient lentiviral vectors containing either full length HPV16 long control region (LCR) or Fragment 1 (SEQ ID NO: 2), Fragment 2 (SEQ ID NO: 3), Fragment 3

Figure 7:
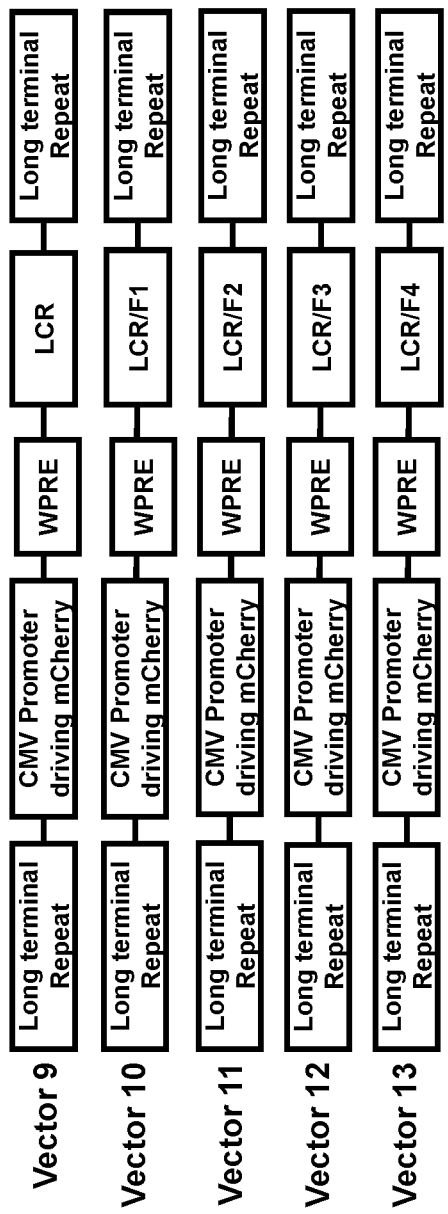
FIG. 7 depicts exemplary vector-in-vector (VIV) embodiments used in conjunction with Examples detailed herein.

(SEQ ID NO: 4), and Fragment 4 (SEQ ID NO: 5) as described herein (see, for e.g., FIG. 7 and related Examples herein).

Figure 16:
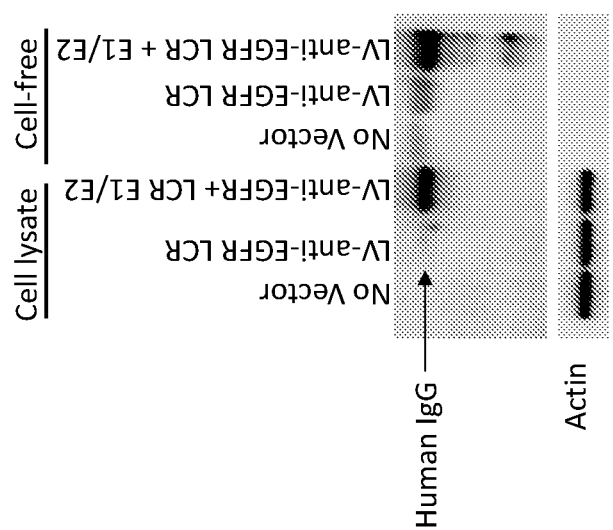
FIG. 16 depicts expression of an anti-EGFR antibody using an integrase-deficient lentiviral vector containing a HPV ori sequence.

After 24 hours, cells were transfected with plasmids containing HPV16 E1 (SEQ ID NO: 6) and E2 (SEQ ID NO: 7) with Lipofectamine 2000. After 2 days, DNA was extracted for analysis by qPCR. Primers represented by SEQ ID NO: 11 and SEQ ID NO: 12, which are specific for the episomal form of the lentiviral vector were used to determine the episomal copy number. Notably, this primer set amplified only 1- and 2-LTR episomes. The data for this Example is depicted in FIG. 16. Therein, the numbers associated with the LCR and fragments thereof reflect a fold-change increase for each of the conditions following the addition of E1 and E2.

In a separate set of related experiments, analysis was carried out for mCherry expression from integrase-deficient lentiviral vectors containing the HPV LCR and 3' fragments thereof. Briefly, 293T cells were transduced with D64V integrase-deficient lentiviral vectors expressing mCherry and either full length HPV16 long control region (LCR) or Fragment 1 (SEQ ID NO: 2), Fragment 2 (SEQ ID NO: 3), Fragment 3 (SEQ ID NO: 4), and Fragment 4 (SEQ ID NO: 5). At the same time, cells were transduced with lentivirus expressing HPV16 E1 (SEQ ID NO: 6) and E2 (SEQ ID NO: 7). After 2 days, mCherry expression was analyzed by FACS.

Figure 13:
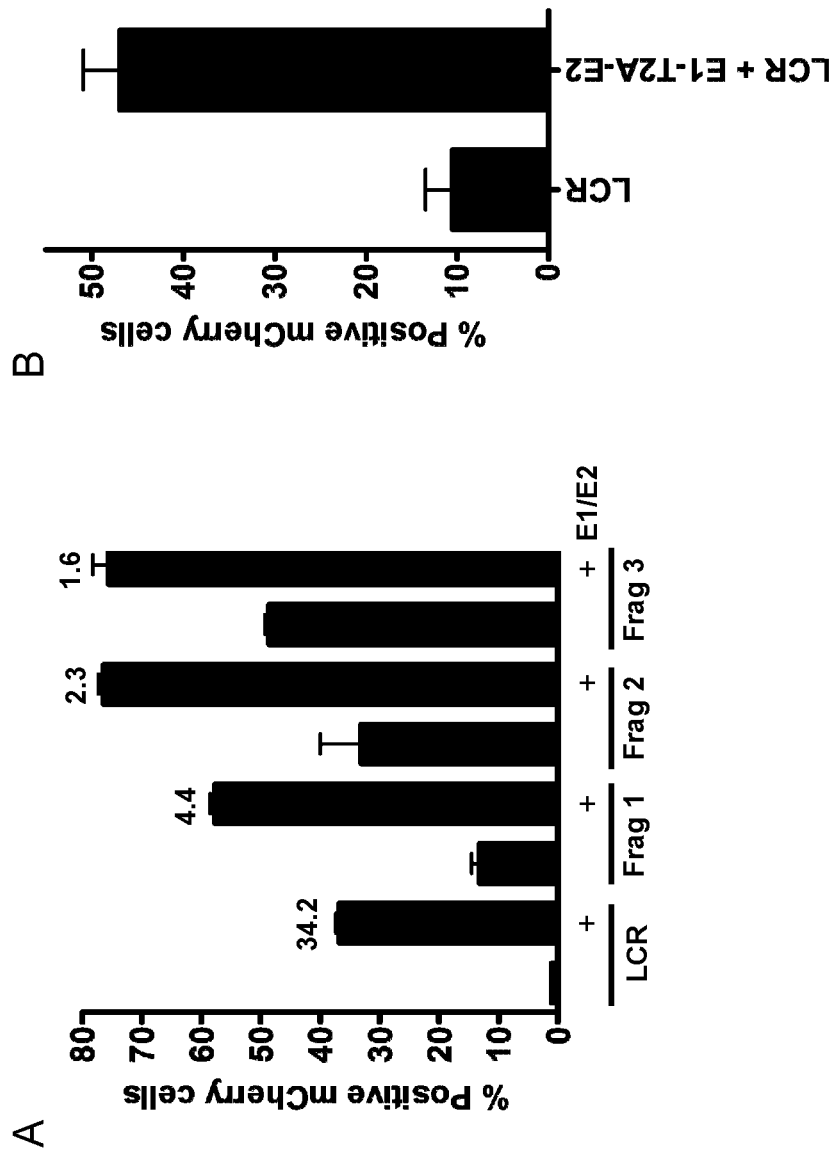
FIG. 13 depicts an analysis of (A) mCherry expression from integrase-deficient lentiviral vectors containing the HPV LCR and 3' fragments; and (B) mCherry expression from integrase-deficient vectors which either express or do not express HPV16 E1-T2A-E2 from a single vector.

As shown in FIG. 13A, the percent of mCherry cells are identified for each of the tested conditions. The numbers associated with the LCR and fragments thereof reflect a fold-change increase for each of the conditions following the addition of E1 and E2.

In a separate set of related experiments, 293T cells were transduced with a D64V integrase-deficient lentiviral vector expressing mCherry and the full-length HPV16 long control region identified previously as SEQ ID NO: 1. At the same time, cells were transduced with lentivirus expressing HPV16 E1-T2A-E2 (SEQ ID NO: 10) from a single vector (see: Vector 25 from FIG. 9). After 2 days, mCherry expression was analyzed by FACS and the data is depicted in FIG. 13B. As shown therein, transduction with HPV16 E1-T2A-E2 (SEQ ID NO: 10) resulted in a significant increase in positive mCherry cells.

Figure 14:
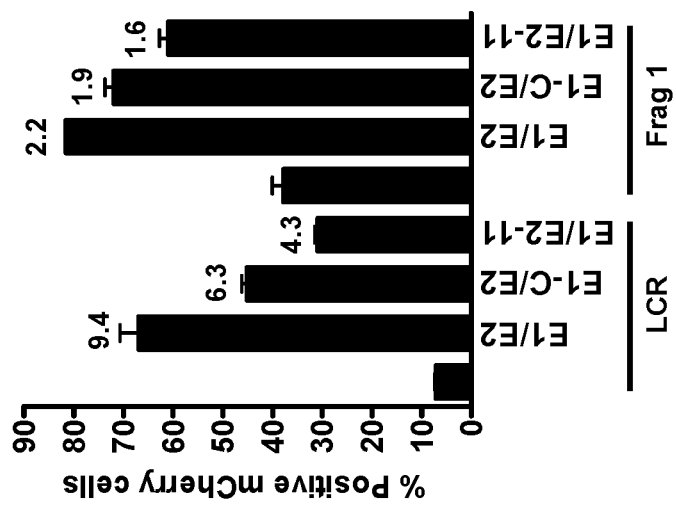
FIG. 14 depicts an analysis of mCherry expression from an integrase-deficient lentiviral vector containing the HPV LCR following the addition of E1, E1-C, and E2-11.

In a separate set of related experiments, an analysis was conducted of mCherry expression using integrase-deficient lentiviral vectors containing HPV LCR following the addition of E1, E1-C, and E2-11. Briefly, 293T cells were transduced with a D64V integrase-deficient lentiviral vector expressing mCherry and HPV16 LCR (SEQ ID NO: 1) or Fragment 1 (SEQ ID NO: 2). At the same time, cells were transduced with HPV16 E1 (i.e., Vector 21 in FIG. 9; and SEQ ID NO: 6) or a E1 carboxy (C)-terminal fragment (i.e., Vector 22 in FIG. 9; and SEQ ID NO: 8) and HPV16 E2 (i.e., Vector 23 in FIG. 9; and SEQ ID NO: 7) or HPV11 E2 (i.e., Vector 24 in FIG. 9; and SEQ ID NO: 9). After 2 days, mCherry expression was analyzed by FACS. As shown in FIG. 14, the percent of mCherry cells are identified for each of the tested conditions. The numbers associated with the tested conditions reflect a fold-change increase for each of the conditions following the addition of E1 and E2.

Example 13—Antibody Expression

As mentioned herein, one of the features of the disclosed system is the usefulness of the disclosed system to express an antibody. In a series of representative experiments detailed herein, an anti-HER2 antibody was expressed using the lentiviral vector system. Briefly, 293T cells were infected with a D64 integrase-deficient lentiviral vector (i.e., Vector 20) containing an antibody sequence against HER2 (SEQ ID NO: 13) and the HPV LCR (SEQ ID NO: 1) sequence.

Figure 15:
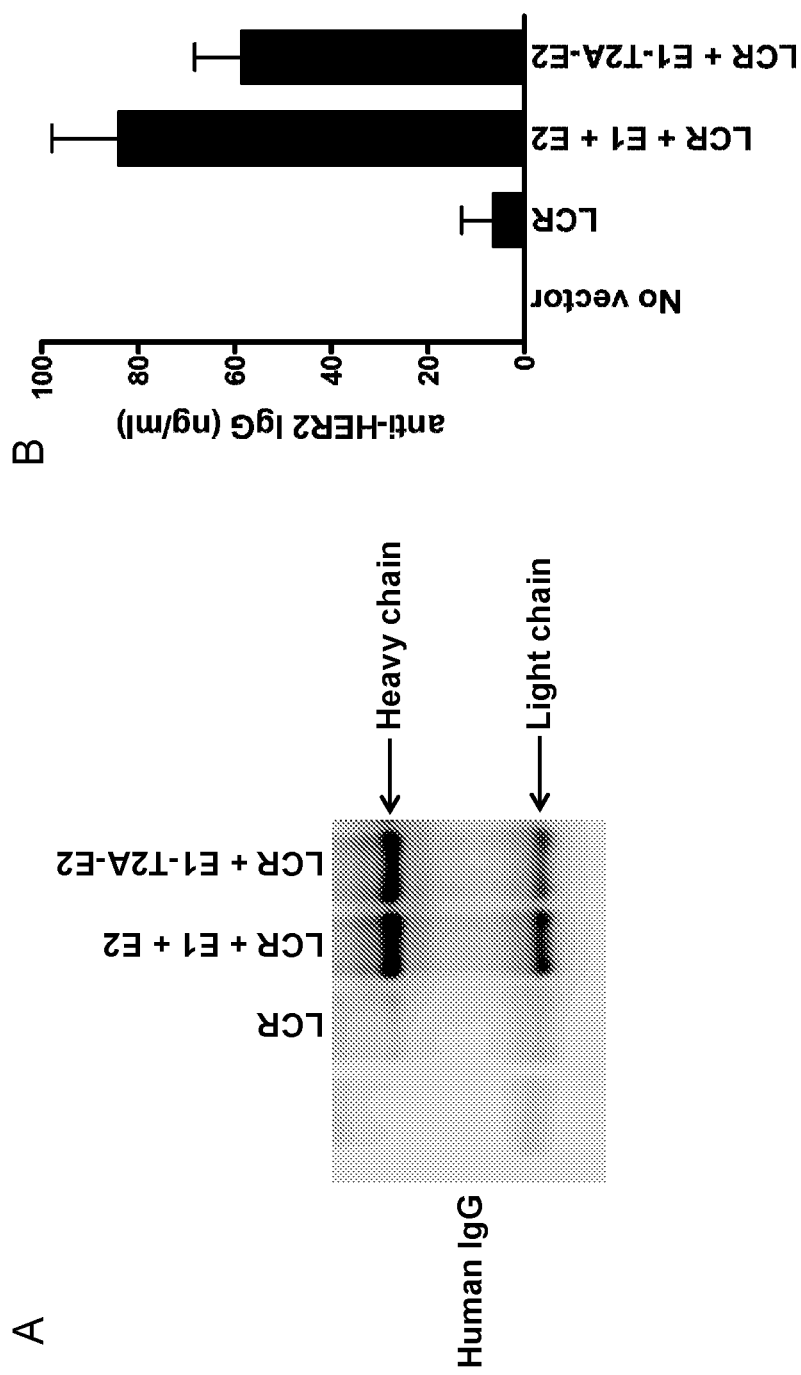
FIG. 15 depicts expression of an anti-HER2 antibody using an integrase-deficient lentiviral vector containing the HPV LCR as determined by (A) immunoblot; and (B) IgG concentration.

At the same time, cells were infected with lentiviral vectors containing E1 (SEQ ID NO: 6) and E2 (SEQ ID NO: 7). After 3 days, cell culture media was collected. Antibody was purified from the media using Protein A/G agarose beads. An immunoblot was performed using a sheep anti-human antibody (Thermo Scientific). Antibody production was increased with the addition of E1 and E2 as shown in FIG. 15A. Further, as shown in FIG. 15B, anti-HER2 IgG concentration was determined using the EasyTiter IgG kit (Thermo Scientific).

Further, as shown in FIG. 16 herein, additional antibodies can also be expressed using the systems disclosed herein. In FIG. 16, an immunoblot demonstrating expression of an anti-EGFR antibody (SEQ ID NO: 14) is shown. Briefly, 293T cells were infected with a D64 integrase-deficient lentiviral vector containing an antibody sequence against EGFR (see: SEQ ID NO: 14 below) and the HPV fragment 2 (SEQ ID NO: 3).

After 24 hours, cells were infected with lentiviral vectors containing E1 (SEQ ID NO: 6) and E2 (SEQ ID NO: 7). After 3 days, cell lysate and cell culture media was collected. Antibody was purified from media using Protein A/G agarose beads and extracted from cells by cell lysis. An immunoblot was performed using a sheep anti-human antibody (Thermo Scientific) and an anti-actin (Sigma) antibody for a protein loading control for cell lysate. Antibody production was increased in both cell lysate and media with the addition of E1 and E2, as shown in FIG. 16.

Example 14—microRNA Expression and Knock-Down

As mentioned herein, one of the features of the disclosed system is the usefulness of the disclosed system to express a microRNA. As a non-limiting example, constructs were designed to express microRNA for CCR5 based on the SEQ ID NO: 15.

Figure 17:
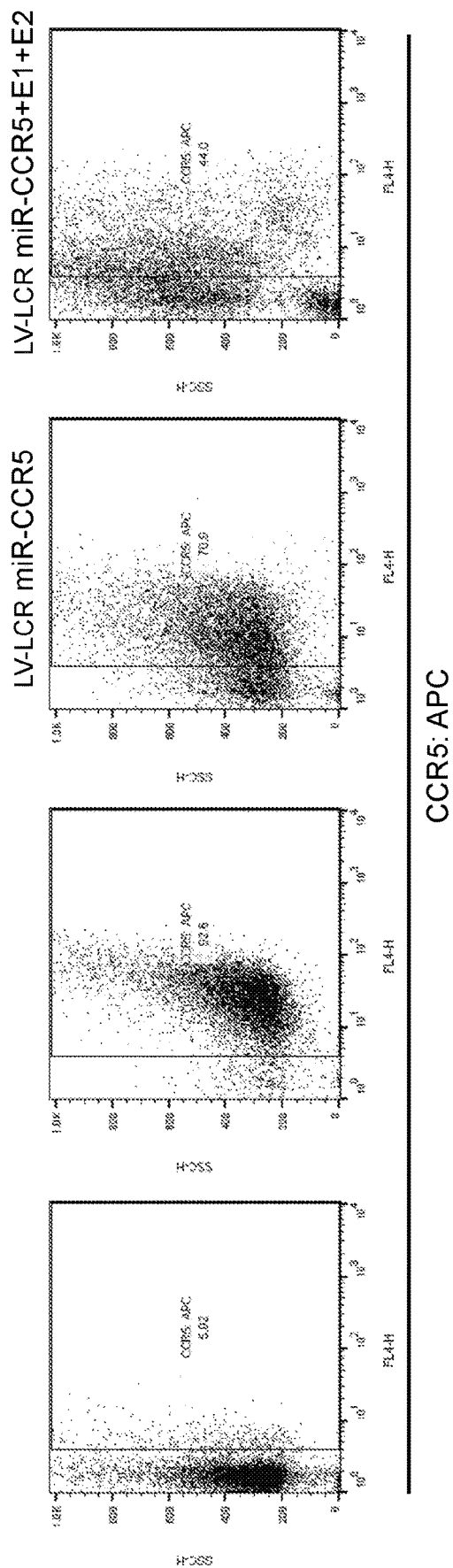
FIG. 17 depicts a knock-down of CCR5 expression using a lentiviral vector that contains full-length LCR of HPV16.

Briefly, HeLa cells expressing CCR5 were infected with a D64 integrase-deficient lentiviral vector (i.e., Vector 20) containing a microRNA sequence against CCR5 (SEQ ID NO: 15) and the full-length HPV LCR (SEQ ID NO: 1) sequence. At the same time, cells were infected with lentiviral vectors containing E1 and E2. After 3 days, cells were collected and analyzed for CCR5 expression by FACS analysis with an anti-CCR5 APC-conjugated antibody. As shown in FIG. 17, the percentage of CCR5 positive cells decreased from 92.6% to 70.9% with LV-LCR miR-CCR5 and to 44% with LV-LCR miR-CCR5 plus E1 and E2.

Figure 18:
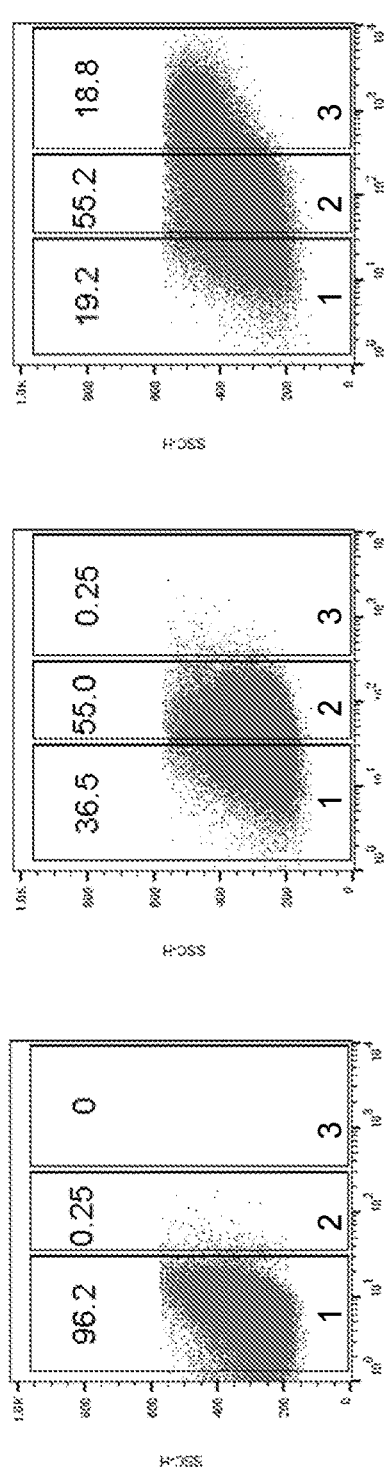
FIG. 18 depicts a knock-down of CCR5 expression using a lentiviral vector that contains Frag 2 of the LCR of HPV16.

In related experiments, a D64 integrase-deficient lentiviral vector containing a microRNA sequence against CCR5 and the Fragment 2 (SEQ ID NO: 3) LCR sequence were utilized. As shown in FIG. 18, there was a similar decrease in CCR5 expression following the addition of miR-CCR5 and even more so when E1 and E2 were added.

Referring in more detail to FIG. 18, the upper panels show the distribution of cells, each represented by a single dot, based on the level of expression of mCherry. The lower panels show the corresponding change in CCR5 expression that is related to the level of DNA replication and production of a miRNA against CCR5. CCR5 is detected by a fluorescent monoclonal antibody used for staining the cell surface. Without any LV vector (left panels) there is no expression of mCherry (all cells are in Sector 1) and CCR5 expression is uniformly high at around 200 fluorescence intensity units. By adding LV-LCR (Fragment 2; SEQ ID NO: 3) containing miRCCR5 we find cells with basal expression of mCherry (55% of cells now found in the Sector 2) and some reduction in CCR5 expression leading to a new population with fluorescence intensity centered around 30 intensity units (dashed line on the lower, center panel). By adding both LV-LCR miRCCR5 and a non-integrating lentivirus vector expressing E1 and E2 replication proteins, we find 18.8% of cells with highest expression of mCherry (Sector 3) and find a new population (curve 3, gray and dashed line) with even lower CCR5 expression that is less than 20 fluorescence intensity units. These data demonstrate the capacity for a VIV containing LCR Fragment 2 (SEQ ID NO: 3) to express a basal level of miRCCR5 that is biologically active in reducing cell surface expression of the CCR5 protein. Further, the results show the impact of adding E1/E2 DNA replication proteins on vector copy number (related to the expression of mCherry) and increased miRCCR5 expression leading to further reduction in cell surface CCR5 expression.

Example 15—EBV-Based Initiator Protein

As mentioned herein, initiator proteins such as E1 (SEQ ID NO: 6) and E2 (SEQ ID NO: 7) are used to augment the effectiveness of the systems described herein. An alternate initiator protein that can be used in the current system is EBNA-1 (SEQ ID NO: 32). Accordingly in a series of experiments, 293T cells were transduced with a D64V integrase-deficient lentiviral vector (i.e., Vector 27) expressing GFP and the Epstein-Barr Virus (EBV) OriP sequence (SEQ ID NO: 31).

Figure 19:
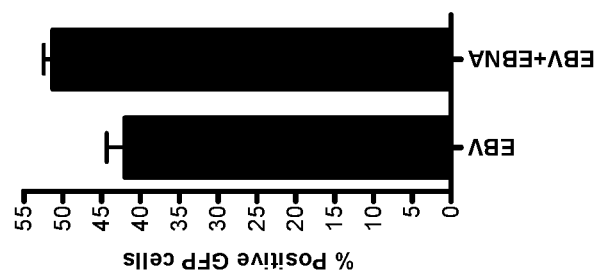
FIG. 19 depicts expression of GFP in cells transduced with a D64V integrase-deficient lentiviral vector using an Epstein-Barr Virus (EBV) oriP sequence.

After 24 hours, cells were transfected with a plasmid containing EBV EBNA-1 (SEQ ID NO: 32) with Lipofectamine 2000. After 2 days, GFP expression was analyzed by FACS. As shown in representative data in FIG. 19, EBV plus EBNA resulted in enhanced GFP expression. Accordingly, this data demonstrates that the initiator protein/ori interaction is not limited to E1/E2 interactions but can also include Epstein-Barr viral components.

Example 16—LCR Fragment Combinations and Analysis

Figure 20:
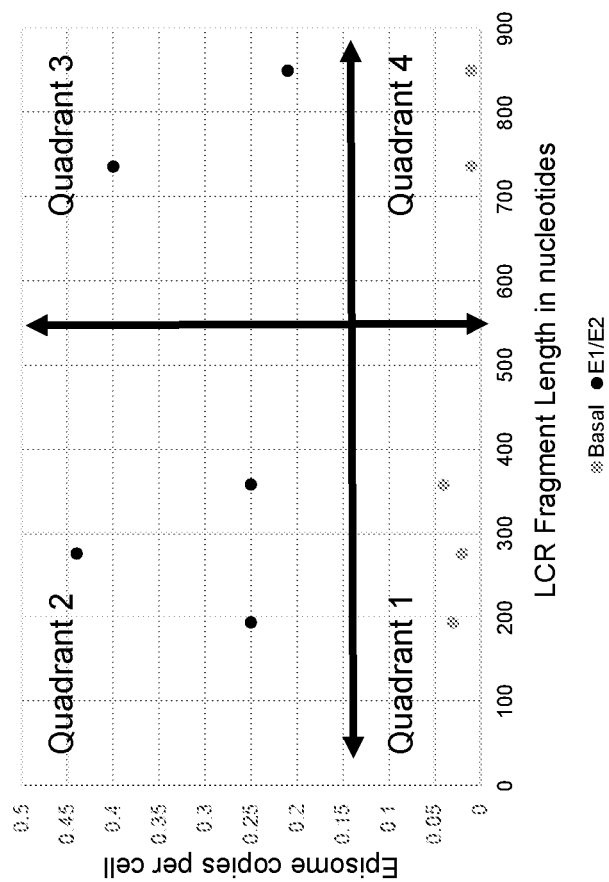
FIG. 20 depicts a schematic demonstrating the basal and E1-E2-induced episomal copy number for Frag 1, Frag 2, Frag 3, Frag 4, and full-length LCR of HPV16.

Based on the data detailed herein, varied levels of expression, as determined by episome copies per cell, can be attributed to the various LCR fragments tested herein. As shown in FIG. 20, and moving from right to left, data for full-length LCR (SEQ ID NO: 1), Fragment 1 (SEQ ID NO: 2), Fragment 2 (SEQ ID NO: 3), Fragment 3 (SEQ ID NO: 4) and Fragment 4 (SEQ ID NO: 5) are shown with and without E1/E2.

Referring to both FIGS. 11 and 20, increasing deletions from the 5' end of LCR remove key functional elements. As detailed herein, basal activity can be defined by the number of episomal DNA copies measured by quantitative PCR assay, when LCR or fragments of LCR are present within a lentivirus-derived episome vector, without added E1/E2 proteins. Inducible activity can be measured by transfecting expression plasmids containing E1 and E2, then introducing a lentivirus-derived episome vector before measuring episomal DNA copy number per cell in a quantitative PCR assay. Similar results were obtained when the E1/E2 protein expression construct was delivered as a non-integrating lentivirus vector. As detailed herein, basal activity has been determined to be highest for Fragments 2, 3 and 4 of the LCR. This indicates that basal activity is suppressed by the presence of a YY1 transcription factor binding site that is present in both LCR and Fragment 1 but not Fragments 2-4, as shown diagrammatically in FIG. 11. Within Fragments 2-4, Fragment 2 had the highest basal expression and was the only fragment to include both AP1 transcription factor binding sites. Thus, basal transcription is increased when the YY1 site is removed and both AP1 sites are preserved. As detailed herein, inducible activity was determined to be highest for Fragments 1 and 3, lower for Fragments 2 and 4, and lowest for intact LCR. There is an unidentified element within LCR that is not present in Fragment 1 and it acts to suppress inducible DNA replication. When the YY1 and AP1 sites are present (Fragment 1), episomal DNA levels are lower compared to removing YY1 and all AP1 sites (Fragment 3). When the AP1 sites are present without YY1 (Fragment 2) or when YY1, AP1 and two of four E2 binding sites are removed (Fragment 4) inducible episomal DNA formation is intermediate and similar to LCR.

As summarized in FIG. 20, the data detailed herein demonstrates definable differences in basal level expression and the ability for expression to be induced. Based on this summary data, at least four quadrants of activity can be defined as shown initially in FIG. 20.

Moving to FIG. 21, the four quadrants represent varying degrees of activity attributable to the LCR and their fragments. For example, as shown in FIG. 21, Quadrant 1 reflects low activity but 3-4 times higher activity than Quadrant 4, and with a smaller LCR fragment. Quadrant 2 reflects high activity, again with a smaller LCR fragment. Quadrant 3 reflects higher activity but this time with a relatively longer LCR fragment. Finally, Quadrant 4 reflects very low activity with a relatively longer LCR fragment.

As detailed in FIG. 21, each Quadrant can reasonably be associated with a particular preferred outcome. As a first example, when a preferred outcome is for use in gene editing, a LCR chosen from Quadrant 1 can be selected. As a second example, when a preferred outcome is cellular reprogramming, a LCR from Quadrant 2 can be selected. As a third example, when a preferred outcome is immune stimulation, a LCR from Quadrant 3 can be selected. As a fourth example, when a preferred outcome is a placebo effect, a LCR from Quadrant 4 can be selected. Importantly, and based on the preferred outcome, varied LCR fragments can be employed using the current system.

SEQUENCES

The following sequences are referred to herein:

| SEQ ID NO: | Description | Sequence |
|---|---|---|
| 1 | HPV16 LCR nucleotide sequence (945 nucleotides; also referred to herein as LCR | AAGGCCAAACCAAAATTTACATTAGGAAAACGAAA AGCTACACCCACCACCTCATCTACCTCTACAACTGC TAAACGCAAAAAACGTAAGCTGTAAGTATTGTATGT ATGTTGAATTAGTGTTGTTTGTTGTGTATATGTTTGT ATGTGCTTGTATGTGCTTGTAAATATTAAGTTGTAT GTGTGTTTGTATGTATGGTATAATAAACACGTGTGT ATGTGTTTTTAAATGCTTGTGTAACTATTGTGTCATG CAACATAAATAAACTTATTGTTTCAACACCTACTAA TTGTGTTGTGGTTATTCATTGTATATAAACTATATTT GCTACATCCTGTTTTTGTTTTATATATACTATATTTT GTAGCGCCAGGCCCATTTTGTAGCTTCAACCGAATT CGGTTGCATGCTTTTTGGCACAAAATGTGTTTTTTA AATAGTTCTATGTCAGCAACTATGGTTTAAACTTGT ACGTTTCCTGCTTGCCATGCGTGCCAAATCCCTGTTT |

| SEQ ID NO: | Description | Sequence |
|---|---|---|
| | | TCCTGACCTGCACTGCTTGCCAACCATTCCATTGTTT TTTACACTGCACTATGTGCAACTACTGAATCACTAT GTACATTGTGTCTATATAAAATAAATCACTATGCGCC AACGCCTTACATACCGCTGTTAGGCACATATTTTTG GCTTGTTTTAACTAACCTAATTGCATATTTGGCATA AGGTTTAAACTTCTAAGGCCAACTAAATGTCACCCT AGTTCATACATGAACTGTGTAAAGGTTAGTCATACA TTGTTCATTTGTAAAACTGCACATGGGTGTGTGCAA ACCGATTTTGGGTTACACATTTACAAGCAACTTATA TAATAATACTAAACTACAATAATTCATGTATAAAAC TAAGGGCGTAACCGAAATCGGTTGAACCGAAACCG GTTAGTATAAAAGCAGACATTTTATGCACCAAAAG AGAACT |
| 2 | HPV16 LCR fragment 1 nucleotide sequence (736 nucleotides, 209 bases deleted from 5' terminus; also referred to herein as Fragment 1) | GTGTGTATGTGTTTTTAAATGCTTGTGTAACTATTGT GTCATGCAACATAAATAAACTTATTGTTTCAACACC TACTAATTGTGTTGTGGTTATTCATTGTATATAAACT ATATTTGCTACATCCTGTTTTTGTTTTATATATACTA TATTTTGTAGCGCCAGGCCCATTTTGTAGCTTCAAC CGAATTCGGTTGCATGCTTTTTGGCACAAAATGTGT TTTTTTAAATAGTTCTATGTCAGCAACTATGGTTTAA ACTTGGTGTTTACATACCGCTGTTAGGCACATATTT CCTGTTTTCCTGACCTGCACTGCTTGCCAACCATTCC ATTGTTTTTACACTGCACTATGTGCAACTACTGAAT CACTATGTACATTGTGTCTATATAAAATAAATCACTA TGCGCCAACGCCTTACATACCGCTGTTAGGCACATA TTTTTGGCTTGTTTTAACTAACCTAATTGCATATTTG GCATAAGGTTTAAACTTCTAAGGCCAACTAAATGTC ACCCTAGTTCATACATGAACTGTGTAAAGGTTAGTC ATACATTGTTCATTTGTAAAACTGCACATGGGTGTG TGCAAACCGATTTTGGGTTACACATTTACAAGCAAC TTATATAATAATACTAAACTACAATAATTCATGTAT AAAACTAAGGGCGTAACCGAAATCGGTTGAACCGA AACCGGTTAGTATAAAAGCAGACATTTTATGCACCA AAAGAGAACT |
| 3 | HPV16 LCR fragment 2 nucleotide sequence (358 nucleotides, 587 nucleotides deleted from 5' terminus; also referred to herein as Fragment 2) | TGTGTCATATAAAATAAATCACTATGCGCCAACGCC TTACATACCGCTGTTAGGCACATATTTTTGGCTTGTT TAACTAACCTAATTGCATATTTGGCATAAGGTTTAA ACTTCTAAGGCCAACTAAATGTCACCCTAGTTCAT ACATGAACTGTGTAAAGGTTAGTCATACATTGTTCA TTTGTAAAACTGCACATGGGTGTGTGCAAACCGATT TTGGGTTACACATTTACAAGCAACTTATATAATAAT ACTAAACTACAATAATTCATGTATAAAACTAAGGGC GTAACCGAAATCGGTTGAACCGAAACCGGTTAGTA TAAAAGCAGACATTTTATGCACCAAAAGAGAACT |
| 4 | HPV16 LCR fragment 3 nucleotide sequence (276 nucleotides, 669 bases deleted from 5' terminus; also referred to herein as Fragment 3) | CTAATTGCATATTTGGCATAAGGTTTAAACTTCTAA GGCCAACTAAATGTCACCCTAGTTCATACATGAACT GTGTAAAGGTTAGTCATACATTGTTCATTTGTAAAA CTGCACATGGGTGTGTGCAAACCGATTTTGGGTTAC ACATTTACAAGCAACTTATATAATAATACTAAACTA CAATAATTCATGTATAAAACTAAGGGCGTAACCGA AATCGGTTGAACCGAAACCGGTTAGTATAAAAGCA GACATTTTATGCACCAAAAGAGAACT |
| 5 | HPV16 LCR fragment 4 nucleotide sequence (194 nucleotides, 751 nucleotides deleted from 5' terminus; also referred to herein as Fragment 4) | TAGTCATACATTGTTCATTTGTAAAACTGCACATGG GTGTGTGCAAACCGATTTTGGGTTACACATTTACAA GCAACTTATATAATAATACTAAACTACAATAATTCA TGTATAAAACTAAGGGCGTAACCGAAATCGGTTGA ACCGAAACCGGTTAGTATAAAAGCAGACATTTTATG CACCAAAAGAGAACT |
| 6 | E1 HPV16 codon-optimized nucleotide sequence (1,950 nucleotides; also referred to herein as E1) | ATGGCAGACCCCGCTGGAACAAATGGAGAGGAGGG CACTGGGTGTAACGGCTGGTTTTACGTGGAAGCAGT CGTAGAGAAGAAGACAGGCGACGCCATTTCAGACG ACGAGAATGAGAACGATAGCGACACTGGTGAGGAT CTTGTGGACTTTATTGTGAACGACAATGACTATCTC ACCCAGGCAGAAACCGAGACCGCCCACGCCCTCTT CACAGCCCAGGAAGCTAAGCAACATCGGGATGCAG TGCAGGTGCTCAAAAGAAAGTACCTGGTTAGTCCTC TGTCCGACATCTCTGGATGCGTCGACAATAATATCA GTCCAAGGCTGAAGGCTATATGCATAGAGAAGCAG TCAAGAGCGGCGAAGAGGAGACTGTTTGAAAGCGA GGATAGTGGATACGGGAACACAGAAGTCGAGACCC AACAGATGCTCCAGGTGGAGGGTCGCCATGAGACT GAGACCCCCTGCTCCCAGTACAGCGGCGGATCAGG CGGTGGATGCTCTCAGTACTCCAGTGGGTCCGGCGG GGAGGGTGTTTCCGAAAGACACACCATCTGTCAGA CCCCCCTGACTAATATTCTGAACGTACTGAAAACAT CCAACGCCAAGGCTGCCATGCTGGCGAAGTTTAAG GAGCTGTATGGCGTGAGCTTCAGCGAACTGGTGAG ACCATTCAAGAGCAACAAGAGCACCTGTTGTGATTG GTGTATTGCCGCCTTTGGGCTGACTCCATCCATCGC TGACTCTATTAAAACCCTGTTGCAACAGTACTGCCT CTACCTGCATATTCAGTCCCTCGCTTGCTCCTGGGG AATGGTGGTGCTGCTTCTGGTTCGGTATAAGTGTGG CAAAAACAGGGAGACCATCGAGAAGCTCCTTAGTA AGCTCCTGTGTGTGTCTCCCATGTGCATGATGATTG AACCGCCAAAATTGCGGAGCACGGCCGCCGCCCTG TACTGGTACAAAACAGGCATAAGCAACATCAGCGA AGTGTATGGTGACACGCCAGAATGGATACAGAGAC AGACCGTGCTCCAGCACAGTTTTAACGATTGCACAT TTGAGCTGTCTCAGATGGTGCAGTGGGCTTATGATA ATGACATTGTAGACGATTCCGAAATAGCGTATAAGT ACGCCCAGCTCGCAGATACCAATTCCAATGCCAGCG CATTTCTGAAGTCCAATTCACAGGCAAAGATAGTAA AGGATTGCGCTACAATGTCCGCCATTATAAAGA GCGGAGAAAAGCAGATGTCAATGTCCCAATGGAT CAAGTATAGGTGTGATCGCGTTGATGATGGCGGTGA TTGGAAGCAGATCGTGATGTTCCTCCGCTATCAAGG CGTAGAATTCATGTCATTCCTGACCGCCCTGAAACG CTTCCTGCAGGGCATTCTCAAAAAAATTGCATCCT GCTGTATGGCGCGGCTAACACTGGAAAGAGTCTGTT CGGCATGAGCCTTATGAAGTTCCTCCAGGGATCCGT GATATGCTTTGTGAACAGCAAATCACACTTTTGGCT TCAGCCATTGGCAGATGCAAAGATCGGCATGCTGG ACGACGCCACAGTCCCATGCTGGAACTACATAGAC GATAATCTCCGAAACGCATTGGACGGCAATCTGGTG AGCATGGACGTCAAGCACAGGCCTCTGGTGCAACT GAAGTGTCCCCCTCTCCTCATTACGTCAAACATCAA CGCCGGAACAGATAGTCGGTGGCCGTACCTGCACA ATAGACTTGTGGTGTTTACATTTCCTAATGAATTCCC ATTTGACGAAAACGGCAATCCAGTATACGAGCTGA ATGACAAGAACTGGAAGAGTTTTTTCTCTAGGACAT GGTCCAGGTTGAGTCTCCACGAAGACGAGGATAAA GAGAATGACGGAGACTCTTTGCCCACTTTTAAGTGC GTGTCTGGACAAAATACCAATACCCTGTGA |

| SEQ ID NO: | Description | Sequence |
|---|---|---|
| 7 | E2 HPV16 nucleotide sequence (natural sequence, not codon-optimized; also referred to herein as E2) | ATGGAGACTCTTTGCCAACGTTTAAATGTGTGTCAG GACAAAATACTAACACATTATGAAAATGATAGTAC AGACCTACGTGACCATATAGACTATTGGAAACACAT GCGCCTAGAATGTGCTATTTATTACAAGGCCAGAGA AATGGGATTTAAACATATTAACCACCAGGTGGTGCC AACACTGGCTGTATCAAAGAATAAAGCATTACAAG CAATTGAACTGCAACTAACGTTAGAAACAATATATA ACTCACAATATAGTAATGAAAAGTGGACATTACAA GACGTTAGCCTTGAAGTGTATTTAACTGCACCAACA GGATGTATAAAAAACATGGATATACAGTGGAAGT GCAGTTTGATGGAGACATATGCAATACAATGCATTA TACAAACTGGACACATATATATTTGTGAAGAAGC ATCAGTAACTGTGGTAGAGGGTCAAGTTGACTATTA TGGTTTATATTATGTTCATGAAGGAATACGAACATA TTTTGTGCAGTTTAAAGATGATGCAGAAAAATATAG TAAAAATAAAGTATGGGAAGTTCATGCGGGTGGTC AGGTAATATATGTCCTACATCTGTGTTTAGCAGCA ACGAAGTATCCTCTCCTGAAATTATTAGGCAGCACT TGGCCAACCACCCCGCCGCGACCCATACCAAAGCC GTCGCCTTGGGCACCGAAGAAACACAGACGACTAT CCAGCGACCAAGATCAGAGCCAGACACCGGAAACC CCTGCCACACCACTAAGTTGTTGCACAGAGACTCAG TGGACAGTGCTCCAATCCTCACTGCATTTAACAGCT CACACAAAGGACGGATTAACTGTAATAGTAACACT ACACCCATAGTACATTTAAAAGGTGATGCTAATACT TTAAAATGTTTAAGATATAGATTTAAAAAGCATTGT ACATTGTATACTGCAGTGTCGTCTACATGGCATTGG ACAGGACATAATGTAAAACATAAAAGTGCAATTGT TACACTTACATATGATATAGTGAATGGCAACGTGACCA ATTTTTGTCTCAAGTTAAAATACCAAAAACTATTAC AGTGTCTACTGGATTTATGTCTATATGA |
| 8 | The E11-C (carboxy terminus) sequence used in Vector 22 is as follows: | ATGTACTCCAGTGGGTCCGGCGGGGAGGGTGTTTCC GAAAGACACACCATCTGTCAGACCCCCCTGACTAAT ATTCTGAACGTACTGAAAACATCCAACGCCAAGGCT GCCATGCTGGCGAAGTTTAAGGAGCTGTATGGCGTG AGCTTCAGCGAACTGGTGAGACCATTCAAGAGCAA CAAGAGCACCTGTTGTGATTGGTGTATTGCCGCGTT TGGGCTGACTCCATCCATCGCTGACTCTATTAAAAC CCTGTTGCAACAGTACTGCCTCTACCTGCATATTCA GTCCCTCGCTTGCTCCTGGGGAATGGTGGTGCTGCT TCTGGTTCGGTATAAGTGTGGCAAAAACAGGGAGA CCATCGAGAAGCTCCTTAGTAAGCTCCTGTGTGTGT CTCCCATGTGCATGATGATTGAACCGCCAAAATTGC GGAGCACGGCCGCCGCCCTGTACTGGTACAAAACA GGCATAAGCAACATCAGCGAAGTGTATGGTGACAC GCCAGAATGGATACAGAGACAGACCGTGCTCCAGC ACAGTTTTAACGATTGCACATTTGAGCTGTCTCAGA TGGTGCAGTGGGCTTATGATAATGACATTGTAGACG ATTCCGAAATAGCGTATAAGTACGCCCAGCTCGCAG ATACCAATTCCAATGCCAGCGCATTTCTGAAGTCCA ATTCACAGGCAAAGATAGTAAAGGATTGCGCTACA ATGTGCCGCCATTATAAAGAGCGGAGAAAAAGCA GATGTCAATGTCCCAATGGATCAAGTATAGGTGTGA TCGCGTTGATGATGCGGTGATTGGAAGCAGATCGT GATGTTCCTCCGCTATCAAGGCGTAGAATTCATGTC ATTCCTGACCGCCCTGAAACGCTTCCTGCAGGGCAT TCCTAAAAAAATTGCATCCTGCTGTATGGCGCGGC TAACACTGGAAAGAGTCTGTTCGGCATGAGCCTTAT GAAGTTCCTCCAGGGATCCGTGATATGCTTTGTGAA CAGCAAATCACACTTTTGGCTTCAGCCATTGGCAGA TGCAAAGATCGGCATGCTGGACGACGCCACAGTCC CATGCTGGAACTACAGTAAGTACGCTATTCCCGAAAC GCATTGGACGGCAATCGGTGAGCATGGACGTCAA GCACAGGCCTCTGGTGCAACTGAAGTGTCCCCCTCT CCTCATTACGTCAAACATCAACGCCGGAACAGATA GTCGGTGGCCGTACCTGCACAATAGACTTGTGGTGT TTACATTTCCTAATGAATTCCCATTTGACGAAAACG GCAATCCAGTATACGAGCTGAATGACAAGAACTGG AAGAGTTTTTTCTCTAGGACATGGTCCAGGTTGAGT CTCCACGAAGACGAGGATAAAGAATGACGGAGA CTCTTTGCCCACTTTTAAGTGCGTGTCTGGACAAAA TACCAATACCCTGTGA |
| 9 | E2-11 (HPV 11) | ATGGAAGCCATTGCCAAAAGGCTTGATGCTTGCCAG GATCAGCTTCTCGAGCTGTATGAGGAGAACTCTATT GACATTCATAAACACATCATGCACTGGAAATGCATT AGACTGGAGAGCGTGTTGCTGCACAAAGCGAAGCA GATGGGACTGAGCCACATTGGGCTTCAGGTGGTCCC ACCCCTTACTGTGTCAGAGACAAAGGGGCATAATG CCATCGAGATGCAGATGCATTTGGAGTCCCTGGCGA AAACCCAGTATGGTGTCGAGCCATGGACGCTGCAG GACACCAGTTACGAAATGTGGCTCACCCCACCCAA ACGCTGCTTTAAGAAGCAGGGAAATACTGTGGAGG TAAAGTTCGATGGCTGTGAGGACAATGTTATGGAGT ACGTGGTCTGGACACACATCTACTTGCAGGATAATG ACTCTTGGGTAAAAGTCACTTCCTCCGTTGATGCCA AGGGCATCTATTACACGTGTGGACAATTCAAGACGT ACTACGTCAATTTCAATAAGGAAGCTCAGAAGTAC GGCAGCACAAACCATTGGGAAGTTTGCTATGGCTCT ACTGTTATTTGTTCCCTGCTTCAGTGAGTAGCACA GTCCGGGAAGTCAGTATAGCCGAACCCACCACTTAC ACCCCAGCCCAGAACCGCCCCTACAGTTTCCGCT TGCACCACTGAGGACGGCGTGTCTGCACCTCCCCGC AAGCGTGCAAGAGGACCCAGCACTAACAACACCCT GTGTGTGGCCAACATACGGTCAGTGGACAGTACAA TCAACAACATCGTAACCGACAATTACAACAAGCAC CAGAGGCGGAATAATTGTCACTCCGCAGCAACACC GATAGTGCAACTGCAAGGTGATAGCAACTGCCTGA AATGCTTCCGCTATAGGCTGAATGATAAGTATAAAC ACCTGTTTGAACTGGCATCTAGCACCTGGCATTGGG CCTCTCCTGAAGCTCCACACAAGAACGCTATTGTGA CACTGACTTATAGCTCCGAAGAGCAACGACAGCAA TTTCTGAACAGCGTGAAAATCCCTCCGACCATCAGA CATAAGGTGGGGTTTATGTCACTCCATCTCCCTAA |
| 10 | E1-T2A-E2 | ATGGCAGACCCCGCTGGAACAAATGGAGAGGAGGG CACTGGCTGTAACGGCTGGTTTTACGTGGAAGCAGT CGTAGAGAAGAAGACAGGCGACGCCATTTCAGACG ACGAGAATGAGAACGATAGCGACACTGGTGAGGAT CTTGTGGACTTTATTGTGAACGACAATGACTATCTC ACCCAGGCCAGAAACCAGAGACCGCCCACGCCCTT CACAGACCCAGGAGGCTCAAGCAACATCGGGAATCAG TGCAGGTGCTCAAAAGAAAGTACCTGGTTAGTCCTC TGTCCGACATCTCTGGATGCGTCGACAATAATATCA GTCCAAGGCTGAAGGCTATATGCATAGAGAAGCAG TCAAGAGCGGCGAAGAGGAGACTGTTTGAAAGCGA GGATAGTGGATACGGGAACACAGAAGTCGAGACCC AACAGATGCTCCAGGTGGAGGGTCGCCATGAGACT GAGACCCCCTGCTCCCAGTACAGCGGCGGATCAGG CGGTGGATGCTCTCAGTACTCCAGTGGGTCCGGCGG GGAGGGTGTTTCCGAAAGACACACCATCTGTCAGA CCCCCCCTGACTAATATTCTGAACGTACTGAAAACAT CCAACGCCAAGGCTGCCATGCTGGCGAAGTTTAAG GAGCTGTATGGCGTGAGCTTCAGCGAACTGGTGAG ACCATTCAAGAGCAACAAGAGCACCTGTTGTGATTG GTGTATTGCCGCCTTTGGGCTGACTCCATCCATCGC TGACTCTATTAAAACCCTGTTGCAACAGTACTGCCT CTACCTGCATATTCAGTCCCTCGCTTGCTCCTGGGG AATGGTGGTGCTGCTTCTGGTTCGGTATAAGTGTGG CAAAAACAGGGAGACCATCGAGAAGCTCCTTAGTA AGCTCCTGTGTGTGTCTCCCATGTGCATGATGATTG AACCGCCAAAATTGCGGAGCACGGCCGCCGCCCTG TACTGGTACAAAACAGGCATAAGCAACATCAGCGA AGTGTATGGTGACACGCCAGAATGGATACAGAGAC AGACCGTGCTCCAGCACAGTTTTAACGATTGCACAT TTGAGCTGTCTCAGATGGTGCAGTGGGCTTATGATA ATGACATTGTAGATTCCGAAATAGCGTATAAGT ACGCCCAGCTCGCAGATACCAATTCCAATGCCAGCG CATTTCTGAAGTCCAATTCACAGGCAAAGATAGTAA AGGATTGCGCTACAATGTGCCGCCATTATAAAGA GCGGAGAAAAAGCAGATGTCAATGTCCCAATGGAT CAAGTATAGGTGTGATCGCGTTGATGATGCGGTGA TTGGAAGCAGATCGTGATGTTCCTCCGCTATCAAGG CGTAGAATTCATGTCATTCCTGACCGCCCTGAAACG CTTCCTGCAGGGCATTCCTAAAAAAATTGCATCCT GCTGTATGGCGCGGCTAACACTGGAAAGAGTCTGTT CGGCATGAGCCTTATGAAGTTCCTCCAGGGATCCGT GATATGCTTTGTGAACAGCAAATCACACTTTTGGCT |

| SEQ ID NO: | Description | Sequence |
|---|---|---|
| | | TCAGCCATTGGCAGATGCAAAGATCGGCATGCTGG ACGACGCCACAGTCCCATGCTGGAACTACATAGAC GATAATCTCCGAAACGCATTGGACGGCAATCTGGTG AGCATGGACGTCAAGCACAGGCCTCTGGTGCAACT GAAGTGTCCCCCTCTCCTCATTACGTCAAACATCAA CGCCGGAACAGATAGTCGGTGGCCGTACCTGCACA ATAGACTTGTGGTGTTTACATTTCCTAATGAATTCCC ATTTGACGAAAACGGCAATCCAGTATACGAGCTGA ATGACAAGAACTGGAAGAGTTTTTTCTCTAGGACAT GGTCCAGGTTGAGTCTCCACGAAGACGAGGATAAA GAGAATGACGGAGACTCTTTGCCCACTTTTAAGTGC GTGTCTGGACAAAATACCAATACCCTGGGAAGCGG AGAGGGCAGAGGAAGTCTGCTAACATGCGGTGACG TCGAGGAGAATCCTGGACCTATGGAGACTCTTTGCC AACGTTTAAATGTGTGTCAGGACAAAATACTAACAC ATTATGAAAATGATAGTACAGACCTACGTGACCATA TAGACTATTGGAAACACATGCGCCTAGAATGTGCTA TTTATTACAAGGCCAGAGAAATGGGATTTAAACATA TTAACCACCAGGTGGTGCCAACACTGGCTGTATCAA AGAATAAAGCATTACAAGCAATTGAACTGCAACTA ACGTTAGAAACAATATATAACTCACAATATAGTAAT GAAAAGTGGACATTACAAGACGTTAGCCTTGAAGT GTATTTAACTGCACCAACAGGATGTATAAAAAAAC ATGGATATACAGTGGAAGTGCAGTTTGATGGAGAC ATATGCAATACAATGCATTATACAAACTGGACACAT ATATATATTTGTGAAGAAGCATCAGTAACTGTGGTA GAGGGTCAAGTTGACTATTATGGTTTATATTATGTT CATGAAGGAATACGAACATATTTTGTGCAGTTTAAA GATGATGCAGAAAAATATAGTAAAAATAAAGTATG GGAAGTTCATGCGGGTGGTCAGGTAATATTATGTT TACATCTGTGTTTAGCAGCAACGAAGTATCCTCTCC TGAAATTATTAGGCAGCACTTGGCCAACCACTCCGC CGCGACCCATACCAAAGCCGTCGCCTTGGGCACCG AAGAAACACAGACGACTATGCAGCGACCAAGATCA GAGCCAGACACCGGAAACCCCTGCCACACCACTAA GTTGTTGCACAGAGACTCAGTGGACAGTGCTCCAAT CCTCACTGCATTTAACAGCTCACACAAAGGACGGAT TAACTGTAATAGTAACACTACACCCATAGTACATTT AAAAGGTGATGTAATACTTTAAAATGTTTAAGATA TAGATTTAAAAAGCATTGTACATTGTATACTGCAGT GTCGTCTACATGGCATTGGACAGGACATAATGTAAA ACATAAAGTGCAATTGTTACACTTACATATGATAG TGAATGCAACGTGACCAATTTTTGTCTCAAGTTAA AATACCAAAACTATTACAGTGTCTACTGGATTTAT GTCTATATGA |
| 11 | 3' LTR Fwd primer | CTAATTCACTCCCAACGAAG |
| 12 | 5' LTR Rev | GCCGAGTCCTGCGTCGAGAG |
| 13 | Anti-HER2 antibody nucleotide sequence | ATGTACAGGATGCAACTCCTGTCTTGCATTGCACTA AGTCTTGCACTTGTCACGGAGGTTCAGCTGGTGGAG TCTGGCGGTGGCCTGGTGCAGCCAGGGGGCTCACTC CGTTTGTCCTGTGCAGCTTCTGGCTTCAACATTAAA GACACCTATATACACTGGGTGCGTCAGGCCCCGGGT AAGGGCCTGGAATGGGTTGCAAGGATTTATCCTACG AATGGTTATACTAGATATGCCGATAGCGTCAAGGGC CGTTTCACTATAAGCGCAGACACATCCAAAAACAC AGCCTACCTGCAGATGAACAGCCTGCGTGCTGAGG ACACTGCCGTCTATTATTGTTCTAGATGGGGAGGGG ACGGCTTCTATGCTATGGACGTGTGGGGTCAAGGAA CCCTGGTCACCGTCTCCTCGGCTAGCACCAAGGGCC CATCGGTCTTCCCCCTGGCACCCTCCTCCAAGAGCA CCTCTGGGGGCACAGCGGCCCTGGGCTGCCTGGTCA AGGACTACTTCCCCGAACCGGTGACGGTGTCGTGGA ACTCAGGCGCCCTGACCAGCGGCGTGCACACCTTCC CGGCTGTCCTACAGTCCTCAGGACTCTACTCCCTCA GCAGCGTGGTGACCGTGCCCTCCAGCAGCTTGGGCA CCCAGACCTACATCTGCAACGTGAATCACAAGCCCA GCAACACCAAGGTGGACAAGAAAGTTGAGCCCAAA TCTTGTGACAAAACTCACACATGCCCACCGTGCCCA GCACCTGAACTCCTGGGGGGACCGTCAGTCTTCCTC |
| | | TTCCCCCCAAAACCCAAGGACACCCTCATGATCTCC CGGACCCCTGAGGTCACATGCGTGGTGGTGGACGT GAGCCACGAAGACCCTGAGGTCAAGTTCAACTGGT ACGTGGACGGCGTGGAGGTGCATAATGCCAAGACA AAGCCGCGGGAGGAGCAGTACAACAGCACGTACCG TGTGGTCAGCGTCCTCACCGTCCTGCACCAGGACTG GCTGAATGGCAAGGAGTACAAGTGCAAGGTCTCCA ACAAAGCCCTCCCAGCCCCCATCGAGAAAACCATCT CCAAAGCCAAAGGGCAGCCCCGAGAACCACAGGTG TACACCCTGCCCCCATCCCGGGATGAGCTGACCAAG AACCAGGTCAGCCTGACCTGCCTGGTCAAAGGCTTC TATCCCAGCGACATCGCCGTGGAGTGGGAGAGCAA TGGGCAGCCGGAGAACAACTACAAGACCACGCCTC CCGTGCTGGACTCCGACGGCTCCTTCTTCCTCTACA GCAAGCTCACCGTGGACAAGAGCAGGTGGCAGCAG GGGAACGTCTTCTCATGCTCCGTGATGCATGAGGCT CTGCACAACCACTACACGCAGAAGAGCCTCTCCCTG TCTCCGGGTAAACGTAGACGAAAAGCGGGAAGCGG AGAGGGCAGAGGAAGTCTGCTAACATGCGGTGACG TCGAGGAGAATCCTGGACCTGGATCCATGTACAGG ATGCAACTCCTGTCTTGCATTGCACTAAGTCTTGCA CTTGTCACGGAGATCCAGATGACCCAGTCCCCGAGC TCCCTGTCCGCCTCTGTGGGCGATAGGGTCACCATC ACCTGCCGTGCCAGTCAGGATGTGAATACTGCTGTA GCCTGGTATCAACAGAAACCAGGAAAAGCTCCGAA ACTACTGATTTACTCGGCATCCTTCCTCGAGTCTGG AGTCCCTTCTCGCTTCTCTGGTTCCAGATCTGGGAC GGATTTCACTCTGACCATCAGCAGTCTGCAGCCGGA AGACTTCGCAACTTATTACTGTCAGCAACATTATAC TACTCCTCCCACGTTCGGACAGGGTACCAAGGTGGA GATCAAAGAATTCGTGGCTGCACCATCTGTCTTCAT CTTCCCGCCATCTGATGAGCAGTTGAAATCTGGAAC TGCCTCTGTTGTGTGCCTGCTGAATAACTTCTATCCC AGAGAGGCCAAAGTACAGTGGAAGGTGGATAACGC CCTCCAATCGGGTAACTCCCAGGAGAGTGTCACAG AGCAGGACAGCAAGGACAGCACCTACAGCCTCAGC AGCACCCTGACGCTGAGCAAAGCAGACTACGAGAA ACACAAAGTCTACGCCTGCGAAGTCACCCATCAGG GCCTGAGCTCGCCCGTCACAAAGAGCTTCAACAGG GGAGAGTGTTAG |
| 14 | anti-EGFR antibody nucleotide sequence | ATGCAGGTGCAGCTGGTGAAGCAGAGCGGACCCGGGGCT CGTCCAGCCCTCGCCAGAGCCTGAGCATCACCTGCAC GGTGAGCGGCTTCAGCCTGACCAACTACGGGGTGC ACTGGGTCCGGCAGTCGCCCGGCAAGGGGCTGGAG TGGCTGGGCGTGATCTGGAGCGGCGGGAACACCGA CTACAACACCCCTTCACGAGCCGCCTGAGCATCAA CAAGGACAACAGCAAGTCGCAGGTGTTCTTCAAGA TGAACAGCCTCCAGAGCAACGACACCGCCATCTACT ACTGCGCGCGGGCCCTGACCTACTACGACTACGAGT TCGCCTACTGGGGCCAGGGGACCCTGGTCACCGTG AGCGCCGCGAGCACCAAGGGCCCGAGCGTGTTCCC CCTCGCCCCCTCCAGCAAGAGCACCAGCGGCGGGA CCGCCGCCCTGGGCTGCCTGGTCAAGGACTACTTCC CCGAGCCGGTGACGGTGAGCTGGAACTCGGGCGCC CTCACCAGCGGCGTCCACACCTTCCCCGCGGTGCTG CAGAGCAGCGGCCTGTACAGCCTCAGCTCGGTGGT CACCGTGCCCAGCAGCAGCCTGGGCACGCAGACCT ACATCTGCAACGTGAACCACAAGCCCAGCAACACC AAGGTCGACAAGCGTGTGGAGCCGAAGTCGCCCAA GAGCTGCGACAAGACCCACACGTGCCCGCCCTGCC CCGCCCCCGAGCTGCTCGGCGGGCCCAGCGTGTTCC TGTTCCCGCCCAAGCCCAAGGACACCCTGATGATCA GCCGGACCCCCGAGGTCACCTGCGTGGTGGTCGAC GTGAGCCACGAGGACCCGGAGGTGAAGTTCAACTG GTACGTCGACGGCGTGGAGGTGCACAACGCCAAGA CGAAGCCCCGCGAGGAGCAGTACAACAGCACCTAC CGGGTCGTGTCGGTGCTCACCGTCCTGCACCAGGAC TGGCTGAACGGGAAGGAGTACAAGTGCAAGGTGAG CAACAAGGCCCTCCCCGCGCCCATCGAGAAGACCA TCAGCAAGGCCAAGGGCCAGCCGCGCGAGCCCCAG GTGTACACGCTGCCCCCCAGCCGGGACGAGCTGAC CAAGAACCAGGTCAGCCTCACCTGCCTGGTGAAGG GGTTCTACCCGTCGGACATCGCCGTGGAGTGGGAG AGCAACGGCCAGCCCGAGAACAACTACAAGACCAC |

| SEQ ID NO: | Description | Sequence |
|---|---|---|
| | | GCCCCCGGTCCTGGACAGCGACGGCAGCTTCTTCCT CTACAGCAAGCTGACCGTGGACAAGAGCCGCTGGC AGCAGGGGAACGTGTTCTCGTGCAGCGTCATGCAC GAGGGCCCTGCACAACCACTACACCCAGAAGAGCCT CAGCCTGAGCCCCGGCAAGTGAGGAAGCGGAGAGG GCAGAGGAAGTCTGCTAACATGCGGTGACGTCGAG GAGAATCCTGGACCTGGATCCATGGACATCCTGCTC ACCCAGAGCCCGGTGATCCTGTCGGTCAGCCCCGGC GAGCGGGTGAGCTTCAGCTGCCGCGCCAGCCAGTC GATCGGGACGAACATCCACTGGTACCAGCAGCGGA CCAACGGCAGCCCCCGCCTGCTCATCAAGTACGCGA GCGAGAGCATCAGCGGGATTCCCTCGCGGTTCAGC GGCAGCGGGAGCGGCACCGACTTCACCCTGAGCAT CAACAGCGTGGAGTCGGAGGACATCGCCGACTACT ACTGCCAGCAGAACAACAACTGGCCGACGACCTTC GGCGCCGGGACCAAGCTGGAGCTCAAGCGCGAATT CGTGGCTGCACCATCTGTCTTCATCTTCCCGCCATCT GATGAGCAGTTGAAATCTGGAACTGCCTCTGTTGTG TGCCTGCTGAATAACTTCTATCCCAGAGAGGCCAAA GTACAGTGGAAGGTGGATAACGCCCTCCAATCGGG TAACTCCCAGGAGAGTGTCACAGAGCAGGACAGCA AGGACAGCACCTACAGCCTCAGCAGCACCCTGACG CTGAGCAAAGCAGACTACGAGAAACACAAAGTCTA CGCCTGCGAAGTCACCCATCAGGGCCTGAGCTCGCC CGTCACAAAGAGCTTCAACAGGGGAGAGTGTTAGG CG |
| 15 | CCR5 microRNA target sequence | GAGCAAGCTCAGTTTACA |
| 16 | Epstein-Barr OriP sequence | ATGAGGATAGCATATGCTACCCGGATACAGATTAG GATAGCATATACTACCCAGATATAGATTAGGATAGC ATATACTACCCAGATATAGATTAGGATAGCCTATGC TACCCAGATATAAATTAGGATAGCATATACTACCCA GATATAGATTAGGATAGCATATGCTACCCAGATATA GATTAGGATAGCCTATGCTACCCAGATATAGATTAG GATAGCATATGCTACCCAGATATAGATTAGGATAGC ATATGCTATCCAGATATTTGGGTAGTATATGCTACC CAGATATAAATTAGGATAGCATATACTACCCTAATC TCTATTAGGATAGCATATGCTACCCGGATACAGATT AGGATAGCATATACTACCCAGATATAGATTAGGAT AGCATATGCTACCCAGATATAGATTAGGATAGCCTA TGCTACCCAGATATAAATTAGGATAGCATATACTAC CCAGATATAGATTAGGATAGCATATGCTACCCAGAT ATAGATTAGGATAGCCTATGCTACCCAGATATAGAT TAGGATAGCATATGCTATCCAGATATTTGGGTAGTA TATGCTACCCATGGCAACATTAGCCCACCGTGCTCT CAGCGACCTCGTGAATATGAGGACCAACAACCCTG TGCTTGGCGCTCAGGCGCAAGTGTGTGTAATTTGTC CTCCAGATCGCAGCAATCGCGCCCCTATCTTGGCCC GCCCACCTACTTATGCAGGTATTCCCGGGGTGCCA TTAGTGGTTTTGTGGGCAAGTGGTTTGACCGCAGTG GTTAGCGGGGTTACAATCAGCCAAGTTATTACACCC TTATTTTACAGTCCAAAACCGCAGGGCGGCGTGTGG GGGCTGACGCGTGCCCCCACTCCACAATTTCAAAAA AAAGAGTGGCCACTTGTCTTTGTTTATGGGCCCCAT TGGCGTGGAGCCCGTTTAATTTTCGGGGGTGTTAG AGACAACCAGTGGAGTCCGCTGCTGTCGGCGTCCAC TCTCTTTCCCCTTGTTACAAATAGAGTGTAACAACA TGGTTCACCTGTCTTGGTCCCTGCCTGGGACACATC TTAATAACCCCAGTATCATATTGCACTAGGATTATG TGTTGCCCATAGCCATAAATTCGTGTGAGATGGACA TCCAGTCTTTACGGCTTGTCCCCACCCCATGGATTTC TATTGTTAAAGATATTCAGAATGTTTCATTCCTACA CTAGTATTTATTGCCCAAGGGGTTTGTGAGGGTTAT ATTGGTGTCATAGCACAATGCCACCACTGAACCCCC CGTCCAAATTTATTCTGGGGCGTCACCTGAAACC TTGTTTTCGAGCACCTCACATACACCTTACTGTTCAC AACTCAGCAGTTATTCTATTAGCTAAACGAAGGAGA ATGAAGAAGCAGGCGAAGATTCAGGAGAGTTCACT GCCCGCTCCTTGATCTTCAGCCACTGCCCTTGTGACT AAAATGGTTCACTACCCTCGTGGAATCCTGACCCCA TGTAAATAAACCGTGACAGCTCATGGGGTGGGAG ATATCGCTGTTCCTTAGGACCCCTTTTACTAACCCTAA TTCGATAGCATATGCTTCCCGTTGGGTAACATATGC TATTGAATTAGGGTTAGTCTGGATAGTATATACTAC TACCCGGGAAGCATATGCTACCCGTTTAGGGT |
| 17 | Platelet-derived growth factor (PDGF) | ATGAATCGCTGCTGGGCGCTCTTCCTGTCTCTCTGCT GCTACCTGCGTCTGGTCAGCGCCGAGGGGGACCCC ATTCCCGAGGAGCTTTATGAGATGCTGAGTGACCAC TCGATCCGCTCCTTTGATGATCTCCAACGCCTGCTG CACGGAGACCCCGGAGAGGAAGATGGGGCCGAGTT GGACCTGAACATGACCCGCTCCCACTCTGGAGGCG AGCTGGAGAGCTTGGCTCGTGGAAGAAGGAGCCTG GGTTCCCTGACCATTGCTGAGCCGGCCATGATCGCC GAGTGCAAGACGCGCACCGAGGTGTTCGAGATCTC CCGGCGCCTCATAGACCGCACCAACGCCAACTTCCT GGTGTGGCCGCCCTGTGTGGAGGTGCAGCGCTGCTC CGGCTGCTGCAACAACCGCAACGTGCAGTGCCGCC CCACCCAGGTGCAGCTGCGACCTGTCCAGGTGAGA AAGATCGAGATTGTGCGCAAGAAGCCAATCTTTAA GAAGGCCACGGTGACGCTGGAAGACCACCTGGCAT GCAAGTGTGAGACAGTGGCAGCTGCACGGCCTGTG ACCCGAAGCCCGGGGGTTCCAGGAGCAGCGAGC CAAAACGCCCCAAACTCGGGTGACCATTCGGACGG TGCGAGTCCGCCGGCCCCCAAGGGCAAGCACCGG AAATTCAAGCACACGCATGACAAGACGGCACTGAA GGAGACCCTTGGAGCCTAG |
| 18 | Bone morphogenetic protein 1 (BMP1) nucleotide sequence (NM_001199.3) | ATGCCCGGCGTGGCCCGCCTGCCGCTGCTGCTCGGG CTGCTGCTGCTCCCGCGTCCCGGCCGGCCGCTGGAC TTGGCCGACTACACCTATGACCTGGCCGAGGAGGA CGACTCGGAGCCCCTCAACTACAAAGACCCCTGCA AGGCGGCTGCCTTTCTTGGGGACATTGCCCTGGACG AAGAGGACCTGAGGGCCTTCCAGGTACAGCAGGCT GTGGATCTCAGACGGCACAGCTCGTAAGTCCTCC ATCAAAGCTGCAGTTCCAGGAAACACTTCTTACCCCG AGCTGCCAGAGCACCAACGGGCAGCCTCAGAGGGG AGCCTGTGGGAGATGGAGAGGTAGATCCCGTAGCC GGCGGGCGGCGACGTCCCGACCAGAGCGTGTGTGG CCCGATGGGGTCATCCCCTTTGTCATTGGGGGAAAC TTCACTGGTAGCCAGAGGGCAGTCTTCCGGCAGGCC ATGAGGCACTGGGAGAAGCACACCTGTGTCACCTTC CTGGAGCGCACTGACGAGGACAGCTATATTGTGTTC ACCTATCGACCTTGCGGGTGCTGCTCCTACTGGTGGGT CGCCGCGGCGGGGGCCCCCAGGCCATCTCCATCGG CAAGAACTGTGACAAGTTCGGCATTGTGGTCCACGA GCTGGGCCACGTCGTCGGCTTCTGGCACGAACACAC TCGGCCAGACCGGGACCGCCACGTTTCATCGTTCG TGAGAACATCAGCCAGGCAGGAGTATAACTTCC TGAAGATGGAGCCTCAGGAGGTGGATCCCTGGGG GAGACCTATGACTTCGACAGCATCATGCATTACGCT CGGAACACATTCTCCAGGGGCATCTTCCTGGATCA ATTGTCCCCAAGTATGAGGTGAACGGGGTGAAACC TCCCATTGGCCAAAGGACACGGCTCAGCAAGGGGG ACATTGCCCAAGCCCGCAAGCTTTACAAGTGCCCAG CCTGTGGAGAACCCTGCAAGACAGGCAAC TTCTCCTCCCCTGAATACCCAATGGCTACTCTGCTC ACATGCACTGCGTGTGGCGCATCTCTGTCACACCCG GGGAGAAGATCATCCTGAACTTCACGTCCCTGGACC TGTACCGCAGCCGCCTGTGCTGGTACGACTATGTGG AGGTCCGAGATGGCTTCTGGAGGAAGGCGCCCCTC CGAGGCCGCTTCTGCGGGTCCAAACTCCCTGAGCCT ATCGTCTCCACTGACAGCCGCCTCTGGGTTGAATTC CGCAGCAGCAGCAATTGGGTTGGAAAGGGCTTCTTT GCAGTCTACGAAGCCATCTGCGGGGTGATGTGAA AAAGGACTATGGCCACATTCAATCGCCCAACTACCC AGACGATTACCGCCCAGCAAAGTCTGCATCTGGC GGATCCAGGTGTCTGAGGGCTTCCACGTGGGCCTCA CATTCCAGTCCTTTGAGATTGAGCGCCACGACAGCT GTGCCTACGACTATCTGGAGGTTCGCGACGGCCAC AGTGAGAGCAGCACCCTCATCGGGCGCTACTGTGG CTATGAGAAGCCTGATGACATCAAGAGCACGTCCA GCCGCCTCTGGCTCAAGTTCGTCTCTGACGGGTCCA TTAACAAAGCGGGCTTTGCCGTCAACTTTTTCAAAG AGGTGGACGAGTGCTCTCGGCCCAACCGCGGGGGC TGTGAGCAGCGGTGCCTCAACACCCTGGGCAGCTAC |

| SEQ ID NO: | Description | Sequence |
|---|---|---|
| | | AAGTGCAGCTGTGACCCCGGGTACGAGCTGGCCCC AGACAAGCGCCGCTGTGAGGCTGCTTGTGGCGGATT CCTCACCAAGCTCAACGGCTCCATCACCAGCCCGGG CTGGCCCAAGGAGTACCCCCCCAACAAGAACTGCA TCTGGCAGCTGGTGGCCCCCACCCAGTACCGCATCT CCCTGCAGTTTGACTTCTTTGAGACAGAGGGCAATG ATGTGTGCAAGTACGACTTCGTGGAGGTGCGCAGTG GACTCACAGCTGACTCCAAGCTGCATGGCAAGTTCT GTGGTTCTGAGAAGCCCGAGGTCATCACCTCCCAGT ACAACAACATGCGCTGGAGTTCAAGTCCGACAAC ACCGTGTCCAAAAAGGGCTTCAAGGCCCACTTCTTC TCAGAAAAGAGGCCAGCTCTGCAGCCCCCTCGGGG ACGCCCCCACCAGCTCAAATTCCGAGTGCAGAAAA GAAACCGGACCCCCCAGTGA |
| 19 | U89348.1 Human papillomavirus type 16 variant nucleotide sequence | ACTACAATAATCCATGTATAAAACTAAGGGCGTAA CCGAAATCGGTTGAACCGAAACCGGTTAGTATAAA AGCAGACATTTTATGCACCAAAAGAGAACTGCAAT GTTTCAGGACCCACAGGAGCGACCCGGAAAGTTAC CACAGTTATGCACAGAGCTGCAAACAACTATACAT GATATAATATTAGAATGTGTGTACTGCAAGCAACAG TTACTGCGACGTGAGGTATATGACTTTGCTTTTCGG GATTTATGCATAGTATATAGAGATGGGAATCCATAT GCTGTATGTGATAAATGTTTAAAGTTTTATTCTAAA ATTAGTGAGTATAGACATTATTGTTATAGTGTGTAT GGAACAACATTAGAACAGCAATACAACAAACCGTT GTGTGATTTGTTAATTAGGTGTATTAACTGTCAAAA GCCACTGTGTCCTGAAGAAAAGCAAAGACATCTGG ACAAAAAGCAAAGATTCCATAATATAAGGGGTCGG TGGACCGGTCGATGTATGTCTTGTTGCAGATCATCA AGAACACGTAGAGAAACCCAGCTGTAATCATGCAT GGAGATACACCTACATTGCATGAATATATGTTAGAT TTGCAACCAGAGACAACTGATCTCTACTGTTATGAG CAATTAAATGACAGCTCAGAGGAGGAGGATGAAAT AGATGGTCCAGCTGGACAAGCAGAACCGGACAGAG CCCATTACAATATTGTAACCTTTTGTTGCAAGTGTG ACTCTACGCTTCGGTTGTGCGTACAAAGCACACACG TAGACATTCGTACTTTGGAAGACCTGTTAATGGCA CACTAGGAATTGTGTGCCCCATCTGTTCTCAGAAAC CATAATCTACCATGGCTGATCCTGCAGGTACCAATG GGGAAGAGGGTACGGGATGTAATGGATGGTTTTAT GTAGAGGCTGTAGTGGAAAAAAAACAGGGGATGC TATATCAGATGACGAGAACGAAAATGACAGTGATA CAGGTGAAGATTTGGTAGATTTTATAGTAAATGATA ATGATTATTTAACACAGGCAGAAACAGAGACAGCA CATGCGTTGTTTACTGCACAGGAAGCAAAACAACAT AGAGATGCAGTACAGGTTCTAAAACGAAGATATTT GGGTAGTCCACTTAGTGATATTAGTGGATGTGTAGA CAATAATATTAGTCCTAGATTAAAAGCTATATGTAT AGAAAAACAAAGTAGAGCTGCAAAAAGGAGATTAT TTGAAAGCAAAGACAGCGGGTATGGCTATACTGAA GTGGAAACTCAGCAGATGTTACAGGTAGAAGGGCG CCATGAGACTGAAACACCATGTAGTCAGTATAGTG GTGGAAGTGGGGGTGGTTGCAGTCAGTACAGTAGT GGAAGTGGGGGAGGGGTGTTAGTGAAAGACACAA TATATGCCAAACACCACTTACAAATATTTTAAATGT ACTAAAAACTAGTAATGCAAAGGCAGCAATGTTAG CAAAATTTAAAGAGTTATACGGGGTGAGTTTTACAG AATTAGTAAGACCAT TTAAAAGTAATAAATCAACGTGTTGCGATTGGTGTA TTGCTGCATTTGGACTTACACCCAGTATAGCTGACA GTATAAAAACACTATTACAACAATATTGTTTATATT TACACATTCAAAGTTTAGCATGTTCATGGGGAATGG TTGTGTTACTATTAGTAAGATATAAATGTGGAAAAA ATAGAGAAACAATTGAAAAATTGCTGTCTAAACTAT TATGTGTGTCTCCAATGTGTATGATGATAGAGCCTC CAAAATTGCGTAGTACAGCAGCAGCATTATATTGGT ATAAAACAGGTATATCAAATATTAGTGAAGTGTATG GAGACAGTGAACGAAGTGACATGGAACAACAGTA TTACAACATAGTTTTAATGATTGTACATTTGAATTAT CACAGATGGTACAATGGGCCTACGATAATGACATA GTAGACAGTGAAATTGCATATAAATATGCACA ATTGGCAGACACTAATAGTAATGCAAGTGCCTTTCT AAAAAGTAATTCACAGGCAAAAATTGTAAAGGATT GTGCAACAATGTGTAGACATTAT |
| | | AAACGAGCAGAAAAAAAACAAATGAGTATGAGTCA ATGGATAAAATATAGATGTGATAGGGTAGATGATG GAGGTGATTGGAAGCAAATTGTTATGTTTTTAAGGT ATCAAGGTGTAGAGTTTATGTCATTTTTAACTGCAT TAAAAAGATTTTTGCAAGGCATACCTAAAAAAAATT GCATATTACTATATGGTGCAGCTAACACAGGTAAAT CATTATTTGGTATGAGTTTAATGAAATTTCTGCAAG GGTCTGTAATATGTTTTGTAAATTCTAAAAGCCATT TTTGGTTACAACCATTAGCAGATGCCAAAATAGGTA TGTTAGATGATGCTACAGTGCCCTGTTGGAACTATA TAGATGACAATTTAAGAAATGCATTGGATGGAAATT TAGTTTCTATGGATGTAAAGCATAGACCATTGGTAC AACTAAATGCCCTCCATTATTAATTACATCATAACA TTAATGCTGGTACAGATTCTAGGTGGCCTTATTTAC ATAATAGATTGGTGGTGTTTACATTTCCTAATGAGT TTCCATTTGACGAAAACGGAAA TCCAGTGTATGAGCTTAATGATAAGAACTGGAAATC CTTTTTCTCAAGGACGTGGTCCAGATTAAGTTTGCA CGAGGACGAGGACAAGGAAAAACGATGGAGACTCTT TGCCAACGTTTAAATGTGTGTCAGGACAAAATACTA ACACATTATGAAAATGATAGTACAGACCTACGTGA CCATATAGACTATTGGAAACACATCGCGCTAGAATG TGCTATTTATTACAAGGCCAGAGAAATGGGATTTAA ACATATTAACCACCAGGTGGTGCCAACGCTGGCTGT ATCAAAGAATAAAGCATTACAAGCAATTGAACTGC AACTAACGTTAGAACAATATATAACTCACAATATA GTAATGAAAAGTGGACATTACAAGACGTTAGCCTT GAAGTGTATTTAACTGCACCAACAGGATGTATAAA AAAACATGGATATACAGTGGAAGTGCAGTTTGATG GAGACATATGCAATACAATGCATTATACAAACTGG ACACATATATATATTTGTGAAGAAGCATCAGTAACT GTGGTAGAGGGTCAAGTTGACTATTATGGTTTATAT TATGTTCATGAAGGAATACGAACATATTTTGTGCAG TTTAAAGATGATGCAGAAAAATATAGTAAAAATAA AGTATGGGAAGTTCATGCGGGTGGTCAGGTAATATT ATGTCCTACATCTGTGTTTAGCAGCAACGAAGTATC CTCTCCTGAAACTATTAGGCAGCACTTGGCAACCA CTCCGCCGCGACCCATACCAAA GCCGTCGCCTTGGGCACCGAAGAAACAGACGAC TATCCAGCGACCAAGATCAGAGCCAGACACCGGAA ACCCCTGCCACACCACTAAGTTGTTGCACAGAGACT CAGTGGACAGTGCTCCAATCCTCACTGCATTTAACA GCTCACACAAAGGACGGATTAACTGTAATAGTAAC ACTACACCCATAGTACATTTAAAAGGTGATGCT AATACTTTAAAATGTTTAAGATATAGATTTAAAAAG CATTGTAAATTGTATACTGCAGTCGTCTCTACATGG CATTGGACAGCAAATAATGTAAAACATAAAAGTGC AATTGTTACACTTACATATGATAGTGAATGGCAACG TGACCAATTTTGTCTCAAGTTAAAATACCAAAAAC TATTACAGTGTCTACTGGATTTATGTCTATATGACA AATCTTGATCTGCATACACAACATTACTGGCGTGC TTTTTGCTTTGCTTTTGTGCTTTTGTGTGTCTGCCT ATTAATACGTCCGCTGCTTTTGTCTGTGTCTACATAC ACATCATTAATACTATTGGTATTACTATTGTGGATA ACAGCAGCCTCTGCGTTTAGGTGTTTTATTGTATAT ATTGTATTTGTTTATATACCATTATTTTTAATACATA CACATGCACGCTTTTAATTACATAATGTATATGTA CATAATGTAATTGTTACATATAATTGTTGTATACCA TAACTTACTATTTTTTCTTTTTATTTTCATATATAAT TTTTTTTTGTTTGTTTGTTGTTTTTTAATAAACTGT TCTCACTTAACAATGCGACACAAACGTTCTGCAAAA CGCACAAAACGTGCATCGGCTACCCAACTTTATAAA ACATGCAAACAGGCAGGTACATGTCCACCTGACATT ATACCTAAG GTTGAAGGCAAAACTATTGCTGATCAAATATTACAA TATGGAAGTATGGGTGTATTTTTGGTGGGTTAGGA ATTGGAACAGGGTCGGGTACAGGCGGACGCACTGG GTATATTCCATTGGGAACAAGGCCTCCCACAGCTAC AGATACTTGTCCTCGTAAGCCCCCTTTAACAGT AGATCCTGTGGGCCCTTCTGATCCTTCTATAGTTTCT TTAGTGGAAGAAACTAGTTTTATTGATGCTGGTGCA CCAACATCTGTACCTTCCATCCCCCAGATGTATCA GGATTTAGTATTACTACTTCAACTGATACCACACCT GCTATATTAGATATTAATAATACTGTTACTACTGTT ACTACACATAATAATCCCACTTTCACTGACCCATCT |

| SEQ ID NO: | Description | Sequence |
|---|---|---|
| | | GTATTGCAGCCTCCAACACCTGCAGAAACTGGAGG
GCATTTTACACTTTCATCATCCACTATTAGTACACAT
AATTATGAAGAAATTCCTATGGATACATTTATTGTT
AGCACAAACCCTAACACAGTAACTAGTAGCACACC
CATACCAGGGTCTCGCCCAGTGGCACGCCTAGGATT
ATATAGTCGCACAACACAACAAGTTAAAGTTGTAG
ACCCTGCTTTTGTAACCACTCCCACTAAACTTATTAC
ATATGATAATCCTGCATATGAAGGTATAGATGTGGA
TAATACATTATATTTTCCTAGTAATGATAATAGTATT
AATATAGCTCCAGATCCTGACTTTTTGGATATAGTT
GCTTTACATAGGCCAGCATTAACCTCTAGGCGTACT
GGCATTAGGTACAGTAGAATTGGTAATAAACAAAC
ACTACGTACTCGTAGTGGAAAATCTATAGGTGCTAA
GGTACATTATTATTATGATTTGAGTACTATTGATCCT
GCAGAAGAAA
TAGAATTACAAACTATAACACCTTCTACATATACTA
CCACTTCACATGCAGCCTCACCTACTTCTATTAATA
ATGGCTTATATGATATTTATGCAGATGACTTTATTA
CAGATACTTCTACAACCCCGGTACCATCTGTACCCT
CTACATCTTTATCAGGTTATATTCCTGCAAATACAA
CAATTCCTTTTGGTGGTGCATACAATATTCCTTTAGT
ATCAGGTCCTGATATACCCATTAATATAACTGACCA
AGCTCCTTCATTAATTCCTATAGTTCCAGGGTCTCCA
CAATATACAATTATTGCTGATGCAGGTGACTTTTAT
TTACATCCTAGTTATTACATGTTA
CGAAAACGACGTAAACGTTTACCATATTTTTTTTCA
GATGTCTCTTTGGCTGCCTAGTGAGGCCACTGTCTA
CTTGCCTCCTGTCCCAGTATCTAAGGTTGTAAGCAC
GGATGAATATGTTGCACGCACAAACATATATATTCA
TGCAGGAACATCCAGACTACTTGCAGTTGGACATCC
CTATTTTCCTATTAAAAAACCTAACAATAACAAAAT
ATTAGTTCCTAAAGTATCAGGATTACAATACAGGGT
ATTTAGAATACATTTACCTGACCCCAATAAGTTTGG
TTTTCCTGACACCTCATTTTATAATCCAGATACACA
GCGGCTGGTTTGGGCCTGTGTAGGTGTTGAGGTAGG
TCGTGGTCAGCCATTAGGTGTGGGCATTAGTGGCCA
TCCTTTATTAAATAAATTGGATGACACAGAAAATGC
TAGTGCTTATGCAGCAAATGCAGGTGTGGATAATAG
AGAATGTATATCTATGGATTACAAACAAACACAATT
GTGTTTAATTGGTTGCAAACCACCTATAGGGGAACA
CTGGGGCAAAGGATCCCAT
GTACCAATGTTGCAGTAAATCCAGGTGATTGTCCAC
CATTAGAGTTAATAAACACAGTTATTCAGGATGGTG
ATATGGTTGATACTGGCTTTGGTGCTATGGACTTTA
CTACATTACAGGCTAACAAAAGTGAAGTTCCACTGG
ATATTTGTACATCTATTTGCAAATATCCAGATTATAT
TAAAATGGTGTCAGAACCATATGGCGACAGCTTATT
TTTTTATTTACGAAGGGAACAAATGTTTGTTAGACA
TTTATTTAATAGGGCTGGTGCTGTTGGTGAAAATGT
ACCAGACGATTTATACATTAAAGGCTCTGGGTCTAC
TGCCAATTTAGCCAGTTCAATTATTTTCCTACACCG
AGTGGTTCTATGGTTACCTCTGATGCCCAAATATTC
AATAAACCTTATTGGTTACAACGAGCACAGGGCCA
CAATAATGGCATTTGTTGGGGTAACCAACTATTTGT
TACTGTTGTTGATACTACACGCAGTACAAATATGTC
ATTATGTGCTGCCATATCTACTTCAGAAACTACATA
TAAAAATACTAACTTTAAGGAGTACCTACGACATGG
GGAGGAATATGATTTACAGTTTATTTTTCAACTGTG
CAAAATAACCTTAACTGCAGACGTTATGACATACAT
ACATTCTATGAATTCCACTATTTTGGAGGACTGGAA
TTTTGGTCTACAACCCCCCCAGGAGGCACACTAGA
AGATACTTATAGGTTTGTAACATCCCAGGCAATTGC
TTGTCAAAAACATACACCTCCAGCACCTAAAGAAG
ATCCCCTTAAAAAATACACTTTTTGGGAAGTAAATT
TAAAGGAAAAGTTTTCTGACGCCTAGATCAGTTTC
CTTTAGGACGCAAATTTTTACTACAAGCAGGATTGA
AGGCCAAACCAAATTTACATTAGGAAAACGAAAA
GCTACACCCACCACCTCATCTACCTCTACAACTGCT
AAACGACAAAAACGTAAGCTGTAAGTATTGTATGT
ATGTTGAATTAGTGTTGTTTGTTTTATATGTTTGT
ATGTGCTTGTATGTGCTTGTAAATATTAAGTTGTAT
GTGTGTTTGTATGTATGGTATAATAAACACGTGTGT
ATGTGTTTTTAAATGCTTGTGTAACTATTGTGTGATG
CAACATAAATAAACTTATTGTTTCAACACCTACTAA
TTGTGTTGTGGTTATTCATTGTATATAAACTATATTT | |
| | | GCTACAATCTGTTTTTGTTTTATATATACTATATTTT
GTAGCGCCAGCGGCCATTTTGTAGCTTCAACCGAAT
TCGGTTGCATGCTTTTTGGCACAAAATGTGTTTTTTT
AAATAGTTCTATGTCAGCAACTATAGTTTAAACTTG
TACGTTTCCTGCTTGCCATGCGTGCCAAATCCCTGTT
TTCCTGACCTGCACTGCTTGCCAACCATTCCATTGTT
TTTTACACTGCACTATGTGCAACTACTGAATCACTA
TGTACATTGTGTCATATAAAATAAATCACTATGCGC
CAACGCCTTACATACCGCTGTTAGGCACATATTTTT
GGCTTGTTTTAACTAACCTAATTGCATATTTGGCAT
AAGGTTTAAACTTCTAAGGCAACTAAATGTCACCC
TAGTTCATACATGAACTGTGTAAAGGTTAGTCATAC
ATTGTTCATTTGTAAAACTGCACATGGGTGTGTGCA
AACCGTTTTGGGTTACACATTTACAAGCAACTTATA
TAATAATACTAA |
| 20 | GFP Fwd primer: | GGATCCGCCACCATGGAGAGCGACGAGAGCGGC |
| 21 | GFP Rev primer: | GAATTCTTAGCGAGATCCGGTGGAGCC |
| 22 | Psi packaging element | TACGCCAAAAATTTTGACTAGCGGAGGCTAGAAGG AGAGAG |
| 23 | Rev response element | AGGAGCTTTGTTCCTTGGGTTCTTGGGAGCAGCAGG AAGCACTATGGGCGCAGCCTCAATGACGCTGACGG TACAGGCCAGACAATTATTGTCTGGTATAGTGCAGC AGCAGAACATGTTGCTGAGGGCTATTGAGGCGCAA CAGCATCTGTTGCAACTCACAGTCTGGGGCATCAAG CAGCTCCAGGCAAGAATCCTGGCTGTGGAAAGATA CCTAAAGGATCAACAGCTCC |
| 24 | cPPT nucleotide sequence | TTTTAAAAGAAAAGGGGGGATTGGGGGGTACAGTG CAGGGGAAAGAATAGTAGACATAATAGCAACAGAC ATACAAACTAAAGAATTACAAAAACAAATTACAAA ATTCAAAATTTTA |
| 25 | WPRE nucleotide sequence | AATCAACCTCTGATTACAAAATTTGTGAAAGATTGA CTGGTATTCTTAACTATGTTGCTCCTTTTACGCTATG TGGATACGCTGCTTTAATGCCTTTGTATCATGCTATT GCTTCCCGTATGGCTTTCATTTTCTCCTCCTTGTATA AATCCTGGTTGCTGTCTCTTTATGAGGAGTTGTGGC CCGTTGTCAGGCAACGTGGCGTGGTGTGCACTGTGT TTGCTGACGCAACCCCCACTGGTTGGGGCATTGCCA CCACCTGTCAGCTCCTTTCCGGGACTTTCGCTTTCCC CCTCCCTATTGCCACGGCGGAACTCATCGCCGCCTG CCTTGCCCGCTGCTGGACAGGGGCTCGGCTGTTGGG CACTGACAATTCCGTGGTGTTGTCGGGGAAATCATC GTCCTTTCCTTGGCTGCTCGCCTGTGTTGCCACCTGG ATTCTGCGCGGGACGTCCTTCTGCTACGTCCCTTCG CCCTCAATCCAGCGGACCTTCCTTCCCGCGGCCTG CTGCCGGCTCTGCGGCCTCTTCCGCGTCTTCGCCTTC GCCCTCAGACGAGTCGGATCTCCCTTTGGGCCGCCT CCCCGCCT |
| 26 | VEGF nucleotide sequence | ATGACGGACAGACAGACAGACACCGCCCCCAGCCC CAGCTACCACCTCCTCCCCGGCCGGCGGCGGACAGT GGACGGCGGCGGAGCCGCGGGCAGGGGGTCGGGCT CGCGGCGTCGCACTGAAACTTTTCGTCCAACTTCTG GGCTGTTCTCGCTTCGGAGGAGCCGTGGTCCGCGCG GGGGAAGCCGAGCCGAGCGGAGCCGCGAGAAGTGC TAGCTCGGGCCGGGAGGAGCCGCAGCCGGAGGAGG GGGAGGAGGAAGAAGAGAAGGAAGAGGAGAGGGG GCCGCAGTGGCGACTCGGCGCTCGGAAGCCGGGCT CATGGACGGGTGAGGCGGCGGTGTGCGCAGACAGT GCTCCAGCCGCGCGCGCTCCCCAGGCCCTGGCCCGG GCTCGGGCCGGGAGGAAGAGTAGCTCGCCGAGG CGCCGAGGAGAGCGGGCCGCCCCACAGCCCGAGCC GGAGAGGGAGCGCGAGCCGCGCCGGCCCCGGTCGG GCCTCCGAAACCATGAACTTTCTGCTGTCTTGGGTG CATTGGAGCCTTGCCTTGCTGCTCTACCTCCACCAT GCCAAGTGGTCCCAGGCTGCACCCATGGCAGAAGG |

| SEQ ID NO: | Description | Sequence |
|---|---|---|
| | | AGGAGGGCAGAATCATCACGAAGTGGTGAAGTTCA TGGATGTCTATCAGCGCAGCTACTGCCATCCAATCG AGACCCTGGTGGACATCTTCCAGGAGTACCCTGATG AGATCGAGTACATCTTCAAGCCATCCTGTGTGCCCC TGATGCGATGCGGGGGCTGCTGCAATGACGAGGGC CTGGAGTGTGTGCCCACTGAGGAGTCCAACATCACC ATGCAGATTATGCGGATCAAACCTCACCAAGGCCA GCACATAGGAGAGATGAGCTTCCTACAGCACAACA AATGTGAATGCAGACCAAAGAAAGATAGAGCAAGA CAAGAAAAAAATCAGTTCGAGGAAAGGGAAAGG GGCAAAAACGAAAGCGCAAGAAATCCCGGTATAAG TCCTGGAGCGTGTACGTTGGTGCCCGCTGCTGTCTA ATGCCCTGGAGCCTCCCTGGCCCCCATCCCTGTGGG CCTTGCTCAGAGCGGAGAAAGCATTTGTTTGTACAA GATCCGCAGACGTGTAAATGTTCCTGCAAAAACAC AGACTCGCGTTGCAAGGCGAGGCAGCTTGAGTTAA ACGAACGTACTTGCAGATGTGACAAGCCGAGGCGG TGA |
| 27 | 5' LTR nucleotide sequence | GGTCTCTCTGGTTAGACCAGATCTGAGCCTGGGAGC TCTCTGGCTAACTAGGGAACCCACTGCTTAAGCCTC AATAAAGCTTGCCTTGAGTGCTTCAAGTAGTGTGTG CCCGTCTGTTGTGTGACTCTGGTAACTAGAGATCCC TCAGACCCTTTTAGTCAGTGTGGAAAATCTCTAGCA |
| 28 | 3' LTR nucleotide sequence | TGGAAGGGCTAATTCACTCCCAACGAAGATAAGAT CTGCTTTTTGCTTGTACTGGGTCTCTCTGGTTAGACC AGATCTGAGCCTGGGAGCTCTCTGGCTAACTAGGGA ACCCACTGCTTAAGCCTCAATAAAGCTTGCCTTGAG TGCTTCAAGTAGTGTGTGCCCGTCTGTTGTGTGACT CTGGTAACTAGAGATCCCTCAGACCCTTTTAGTCAG TGTGGAAAATCTCTAGCAGTAGTAGTTCATGTCA |
| 29 | CMV promoter nucleotide sequence | ACTAGTATTATGCCCAGTACATGACCTTATGGGACT TTCCTACTTGGCAGTACATCTACGTATTAGTCATCG CTATTACCATGGTGATGCGGTTTTGGCAGTACATCA ATGGGCGTGGATAGCGGTTTGACTCACGGGGATTTC CAAGTCTCCACCCCATTGACGTCAATGGGAGTTTGT TTTGGCACCAAAATCAACGGGACTTTCCAAAATGTC GTAACAACTCCGCCCCATTGACGCAAATGGGCGGT AGGCGTGTACGGTGGGAGGTTTATATAAGCAGAGC TCGTTTAGTGAACCGTCAGATCGCCTGGAGACGCCA TCCACGCTGTTTTGACCTCCATAGAAGA |
| 30 | UbiC promoter nucleotide sequence | GCGCCGGGTTTTGGCGCCTCCCGCGGGCGCCCCCCT CCTCACGGCGAGCGCTGCCACGTCAGACGAAGGGC GCAGGAGCGTTCCTGATCCTTCCGCCCGGACGCTCA GGACAGCGGCCCGCTGCTCATAAGACTCGGCCTTAG AACCCCAGTATCAGCAGAAGGACATTTTAGGACGG GACTTGGGTGACTCTAGGGCACTGGTTTTCTTTCCA GAGAGCGGAACAGGCGAGGAAAAAGTAGTCCCTTCT CGGCGATTCTGCGGAGGGATCTCCGTGGGCGGTG AACGCCGATGATTATATAAGGACGCGCCGGGTGTG GCACAGTAGTTCCGTCGCAGCCGGGATTTGGGTCG CGGTTCTTGTTTGTGGATCGCTGTGATCGTCACTTGG TGAGTTGCGGGCTGCTGGGCTGGCCGGGGCTTTCGT GGCCGCCGGGCCGCTCGGTGGGACGGAAGCGTGTG GAGAGACCGCCAAGGGCTGTAGTCTGGGTCCGCGA GCAAGGTTGCCCTGAACTGGGGGTTGGGGGGAGCG CACAAAATGGCGGCTGTTCCCGAGTCTTGAATGGAA GACGCTTGTAAGGCGGGCTGTGAGGTCGTTGAAAC AAGGTGGGGGCATGGTGGGCGGCAAGAACCCAAG GTCTTGAGGCCTTCGCTAATGCGGGAAAGCTCTTAT TCGGGTGAGATGGCTGGGGCACCATCTGGGGACC CTGACGTGAAGTTTGTCACTGACTGGAGAACTCGG GTTTGTCGTCTGTTGCGGGGCGCAGTTATGCGGT GCCGTTGGGCAGTGCACCCGTACCTTTGGGAGCGC GCCTCGTCGTGTCGTGACGTCACCCGTTCTGTTGG CTTATAATGCAGGGTGGGGCCACCTGCCGGTAGGT TGCGGTAGGCTTTTCTCCGTCGCAGGACGCAGGGTT CGGGCCTAGGGTAGGCTCTCCTGAATCGACAGGCG CCGGACCTCTGGTGAGGGGAGGGATAAGTGAGGCG |

| SEQ ID NO: | Description | Sequence |
|---|---|---|
| | | TCAGTTTCTTTGGTCGGTTTTATGTACCTATCTTCTT AAGTAGCTGAAGCTCCGGTTTTGAACTATGCGCTCG GGGTTGGCGAGTGTGTTTTGTGAAGTTTTTTAGGCA CCTTTTGAAATGTAATCATTTGGGTCAATATGTAAT TTTCAGTGTTAGACTAGTAAA |
| 31 | EBV ori | ATGAGGATAGCATATGCTACCCGGATACAGATTAG GATAGCATATACTACCCAGATATAGATTAGGATAGC ATATGCTACCCAGATATAGATTAGGATAGCCTATGC TACCCAGATATAAATTAGGATAGCATATACTACCCA GATATAGATTAGGATAGCATATGCTACCCAGATATA GATTAGGATAGCCTATGCTACCCAGATATAGATTAG GATAGCATATGCTACCCAGATATAGATTAGGATAGC ATATGCTATCCAGATATTTGGGTAGTATATGCTACC CAGATATAAATTAGGATAGCATATACTACCCTAATC TCTATTAGGATAGCATATGCTACCCGGATACAGATT AGGATAGCATATACTACCCAGATATAGATTAGGAT AGCATATGCTACCCAGATATAGATTAGGATAGCCTA TGCTACCCAGATATAAATTAGGATAGCATATACTAC CCAGATATAGATTAGGATAGCATATGCTACCCAGAT ATAGATTAGGATAGCCTATGCTACCCAGATATAGAT TAGGATAGCATATGCTATCCAGATATTTGGGTAGTA TATGCTACCCATGGCAACATTAGCCACCGTGCTCT CAGCGACCTCGTGAATATGAGGACCAACAACCCTG TGCTTGGCGCTCAGGCGCAAGTGTGTGTAATTTGTC CTCCAGATCGCAGCAATCGCGCCCCTATCTTGGCC GCCCACCTACTTATGCAGGTATTCCCCGGGGTGCCA TTAGTGGTTTTGTGGGCAAGTGGTTTGACCGCAGTG GTTAGCGGGGTTACAATCAGCCAAGTTATTACACCC TTATTTTACAGTCCAAAACCGCAGGGCGGCGTGTGG GGGCTGACGCGTGCCCCCACTCCACAATTTCAAAA AAAGAGTGGCCACTTGTCTTTGTTTATGGGCCCCAT TGGCGTGGAGCCCGTTTAATTTTCGGGGGTGTTAG AGACAACCAGTGGAGTCCGCTGCTGTCGGCGTCCAC TCTCTTTCCCCTTGTTACAAATAGAGTGTAACAACA TGGTTCACCTGTCTTGGTCCCTGCCTGGGACACATC TTAATAACCCCAGTATCATATTGCACTAGGATTATG TGTTGCCCATAGCCATAAATTCGTGTGAGATGGACA TCCAGTCTTTACGGCTTGTCCCCACCCCATGGATTTC TATTGTTAAAGATATTCAGAATGTTTCATTCCTACA CTAGTATTTATTGCCCAAGGGGTTTGTGAGGGTTAT ATTGGTGTCATAGCACAATGCCACCACTGAACCCCC CGTCCAAATTTTATTCTGGGGGCGTCACCTGAAACC TTGTTTTCGAGCACCTCACATACACCTTACTGTTCAC AACTCAGCAGTTATTCTATTAGCTAAACGAAGGAGA ATGAAGAAGCAGGCGAAGATTCAGGAGAGTTCACT GCCCGCTCCTTGATCTTCAGCCACTGCCCTTGTGACT AAAATGGTTCACTACCCTCGTGAATCCTGACCCCA TGTAAATAAAACCGTGACAGCTCATGGGGTGGGAG ATATCGCTGTTCCTTAGGACCCTTTTACTAACCCTAA TTCGATAGCATATGCTTCCCGTTGGGTAACATATGC TATTGAATTAGGGTTAGTCTGGATAGTATATACTAC TACCCGGGAAGCATATGCTACCCGTTTAGGGT |
| 32 | EBNA-1 | ATGTCTGACGAGGGGCCAGGTACAGGACCTGGAAA TGGCCTAGGAGAAGGGGAGACACATCTGGACCAG AAGCTCCGGCGGCAGTGGACCTCAAAGAAGGGG GGTGATAACCATGGACGAGGACGGGAAGAGGACG AGGACGAGGAGGCGGAAGACCAGGAGCCCCGGGC GGCTCAGGATCAGGGCCAAGACATAGAGATGGTGT CCGGAGACCCAAAAACGTCCAAGTTGCATTGGCT GCAAAGGGACCCACGGTGGAACAGGAGCAGGAGC AGGAGCGGGAGGGGCAGGAGCAGGAGGGGCAGGA GCAGGAGGAGGCAGGAGCAGGAGGAGGGGCAGGA GAGGGGCAGGAGGGGCAGGAGGGGCAGGAGCAGG AGGAGGGGCAGGAGCAGGAGGAGGGGCAGGAGGG GCAGGAGGGGCAGGAGCAGGAGGGGCAGGAGCAGG AGGAGGGGCAGGAGCAGGAGGAGGGGCAGGAGGG AGGGGCAGGAGGGGCAGGAGGAGGGGCAGGAGGA GGAGGGGCAGGAGCAGGAGGAGGGGCAGGAGGGG CAGGAGGGGCAGGAGCAGGAGGAGGGGCAGGAGG GCAGGAGCAGGAGGAGGGGCAGGAGCAGGAGGGG CAGGAGCAGGAGGAGGGGCAGGAGCAGGAGGGGCA |

| SEQ ID NO: | Description | Sequence |
|---|---|---|
| | | GGAGCAGGAGGGGCAGGAGCAGGAGGGGCAGGAG<br>GGGCAGGAGCAGGAGGGGCAGGAGGGGCAGGAGC<br>AGGAGGGGCAGGAGGGGCAGGAGCAGGAGGAGGG<br>GCAGGAGGGGCAGGAGCAGGAGGAGGGGCAGGAG<br>GGGCAGGAGCAGGAGGGGCAGGAGGGGCAGGAGC<br>AGGAGGGGCAGGAGGGGCAGGAGCAGGAGGGGCA<br>GGAGGGGCAGGAGCAGGAGGAGGGGCAGGAGCAG<br>GAGGGGCAGGAGCAGGAGGTGGAGGCCGGGGTCG<br>AGGAGGCAGTGGAGGCCGGGGTCGAGGAGGTAGTG<br>GAGGCCGGGGTCGAGGAGGTAGTGGAGGCCGCCGG<br>GGTAGAGGACGTGAAAGAGCCAGGGGGGGAAGTC<br>GTGAAAGAGCCAGGGGGAGAGGTCGTGGACGTGGA<br>GAAAAGAGGCCCAGGAGTCCCAGTAGTCAGTCATC<br>ATCATCCGGGTCTCCACCGCGCAGGCCCCCTCCAGG<br>TAGAAGGCCATTTTTCCACCCTGTAGGGGAAGCCGA<br>TTATTTTGAATACCACCAAGAAGGTGGCCCAGATGG<br>TGAGCCTGACGTGCCCCCGGGAGCGATAGAGCAGG<br>GCCCCGCAGATGACCCAGGAGAGAAGCCCAAGCACT<br>GGACCCCGGGGTCAGGGTGATGGAGGCAGGCGCAA<br>AAAAGGAGGGTGGTTTGGAAAGCATCGTGGTCAAG<br>GAGGTTCCAACCCGAAATTTGAGAACATTGCAGAA<br>GGTTTAAGAGCTCTCCTGGCTAGGAGTCACGTAGAA | |

| SEQ ID NO: | Description | Sequence |
|---|---|---|
| | | AGGACTACCGACGAAGGAACTTGGGTCGCCGGTGT<br>GTTCGTATATGGAGGTAGTAAGACCTCCCTTTACAA<br>CCTAAGGCGAGGAACTGCCCTTGCTATTCCACAATG<br>TCGTCTTACACCATTGAGTCGTCTCCCCTTTGGAATG<br>GCCCCTGGACCCGGCCCACAACCTGGCCCGCTAAG<br>GGAGTCCATTGTCTGTTATTTCATGGTCTTTTTACAA<br>ACTCATATATTTGCTGAGGTTTTGAAGGATGCGATT<br>AAGGACCTTGTTATGACAAAGCCCGCTCCTACCTGC<br>AATATCAGGGTGACTGTGTGCAGCTTTGACGATGGA<br>GTAGATTTGCCTCCCTGGTTTCCACCTATGGTGGAA<br>GGGGCTGCCGCGAGGGTGATGACGAGATGACGG<br>AGATGAAGGAGGTGATGGAGATGAGGGTGAGGAA<br>GGGCAGGAGTGA | |

While certain preferred embodiments of the present invention have been described and specifically exemplified herein, it is not intended that the invention be limited to such embodiments. Various modifications may be made thereto without departing from the scope and spirit of the present invention.

What is claimed is:

1. A non-integrating viral delivery system, the system comprising:
   a viral carrier, wherein the viral carrier contains a defective integrase gene;
   a heterologous viral episomal origin of DNA replication;
   a first sequence encoding at least one initiator protein specific for the heterologous viral episomal origin of DNA replication, wherein expression of the first sequence is inducible; and
   a second sequence encoding at least one gene, gene product, shRNA, siRNA, miRNA, or other RNA of interest,
   wherein the at least one initiator protein, when expressed, functions to regulate expression of the second sequence; and
   wherein the heterologous viral episomal origin of DNA replication comprises a sequence having at least 95% sequence identity with SEQ ID NO: 1.

2. The non-integrating viral delivery system of claim 1, wherein the viral carrier is a lentivirus.

3. The non-integrating viral delivery system of claim 1, wherein the at least one initiator protein specific for the heterologous viral episomal origin of DNA replication comprises E1.

4. The non-integrating viral delivery system of claim 1, wherein the at least one initiator protein specific for the heterologous viral episomal origin of DNA replication comprises E2.

5. The non-integrating viral delivery system of claim 1, wherein the system comprises at least two initiator proteins specific for the heterologous viral episomal origin of DNA replication.

6. The non-integrating viral delivery system of claim 5, wherein the at least two initiator proteins specific for the heterologous viral episomal origin of DNA replication are E1 and E2.

7. The non-integrating viral delivery system of claim 1, wherein the sequence encoding the at least one initiator protein is present on a single discrete plasmid or a non-integrating viral vector.

8. The non-integrating viral delivery system of claim 1, wherein the system comprises at least two initiator proteins specific for the heterologous viral episomal origin of DNA replication, and wherein the sequence encoding the at least two initiator proteins is present on a single discrete plasmid or a non-integrating viral vector.

9. The non-integrating viral delivery system of claim 1, wherein the system comprises at least two initiator proteins specific for the heterologous viral episomal origin of DNA replication, wherein the sequence for a first initiator protein and the sequence for a second initiator protein are present on discrete plasmids or non-integrating viral vectors.

10. The non-integrating viral delivery system of claim 1, wherein the at least one gene product comprises an antibody, an antibody fragment, or a growth factor.

11. The non-integrating viral delivery system of claim 1, wherein the miRNA comprises a CCR5 miRNA.

12. A pharmaceutical composition comprising the non-integrating viral delivery system of claim 1 and at least one pharmaceutically acceptable carrier.

* * * * *

SEQUENCE LISTING

<160> NUMBER OF SEQ ID NOS: 32

<210> SEQ ID NO 1
<211> LENGTH: 946
<212> TYPE: DNA
<213> ORGANISM: human papillomavirus type 16

<400> SEQUENCE: 1

```
aaggccaaac caaatttac attaggaaaa cgaaaagcta cacccaccac ctcatctacc      60
tctacaactg ctaaacgcaa aaaacgtaag ctgtaagtat tgtatgtatg ttgaattagt    120
gttgtttgtt gtgtatatgt ttgtatgtgc ttgtatgtgc ttgtaaatat taagttgtat   180
gtgtgtttgt atgtatggta taataaacac gtgtgtatgt gttttttaaat gcttgtgtaa   240 ctattgtgtc atgcaacata aataaactta ttgtttcaac acctactaat tgtgttgtgg   300
ttattcattg tatataaact atatttgcta catcctgttt ttgtttttata tatactatat   360 tttgtagcgc caggcccatt ttgtagcttc aaccgaattc ggttgcatgc ttttttggcac   420 aaaatgtgtt ttttttaaata gttctatgtc agcaactatg gtttaaactt gtacgtttcc   480
tgcttgccat gcgtgccaaa tccctgtttt cctgacctgc actgcttgcc aaccattcca   540 ttgttttttta cactgcacta tgtgcaacta ctgaatcact atgtacattg tgtcatataa   600
aataaatcac tatgcgccaa cgccttacat accgctgtta ggcacatatt tttggcttgt   660
tttaactaac ctaattgcat atttggcata aggtttaaac ttctaaggcc aactaaatgt   720 cacctagtt catacatgaa ctgtgtaaag gttagtcata cattgttcat ttgtaaaact   780
gcacatgggt gtgtgcaaac cgatttgggg ttacacattt acaagcaact tatataataa   840
tactaaacta caataattca tgtataaaac taagggcgta accgaaatcg gttgaaccga   900
aaccggttag tataaaagca gacattttat gcaccaaaag agaact                   946
```

<210> SEQ ID NO 2
<211> LENGTH: 736
<212> TYPE: DNA
<213> ORGANISM: human papillomavirus type 16

<400> SEQUENCE: 2

```
gtgtgtatgt gttttttaaat gcttgtgtaa ctattgtgtc atgcaacata aataaactta     60
ttgtttcaac acctactaat tgtgttgtgg ttattcattg tatataaact atatttgcta    120
catcctgttt ttgttttata tatactatat tttgtagcgc caggcccatt ttgtagcttc    180
aaccgaattc ggttgcatgc tttttggcac aaaatgtgtt tttttaaata gttctatgtc    240
agcaactatg gttaaaactt gtacgtttcc tgcttgccat gcgtgccaaa tccctgtttt    300
cctgacctgc actgcttgcc aaccattcca tgttttttta cactgcacta tgtgcaacta    360
ctgaatcact atgtacattg tgtcatataa aataaatcac tatgcgccaa cgccttacat    420
accgctgtta ggcacatatt tttggcttgt tttaactaac ctaattgcat atttggcata    480
aggtttaaac ttctaaggcc aactaaatgt caccctagtt catacatgaa ctgtgtaaag    540
gttagtcata cattgttcat ttgtaaaact gcacatgggt gtgtgcaaac cgattttggg    600
ttacacattt acaagcaact tatataataa tactaaacta caataattca tgtataaaac    660
taagggcgta accgaaatcg gttgaaccga accggttag tataaaagca gacattttat     720
gcaccaaaag agaact                                                    736
```

<210> SEQ ID NO 3
<211> LENGTH: 358
<212> TYPE: DNA
<213> ORGANISM: human papillomavirus type 16

<400> SEQUENCE: 3

```
tgtgtcatat aaaataaatc actatgcgcc aacgccttac ataccgctgt taggcacata     60
ttttggcctt gttttaacta acctaattgc atatttggca taaggtttaa acttctaagg    120
ccaactaaat gtcaccctag ttcatacatg aactgtgtaa aggttagtca tcattgttc     180
atttgtaaaa ctgcacatgg gtgtgtgcaa accgattttg ggttacacat ttacaagcaa    240
cttatataat aatactaaac tacaataatt catgtataaa actaagggcg taaccgaaat    300
cggttgaacc gaaaccggtt agtataaaag cagacatttt atgcaccaaa agagaact     358
```

<210> SEQ ID NO 4
<211> LENGTH: 276
<212> TYPE: DNA
<213> ORGANISM: human papillomavirus type 16

<400> SEQUENCE: 4

```
ctaattgcat atttggcata aggtttaaac ttctaaggcc aactaaatgt caccctagtt     60
catacatgaa ctgtgtaaag gttagtcata cattgttcat ttgtaaaact gcacatgggt    120
gtgtgcaaac cgattttggg ttacacattt acaagcaact tatataataa tactaaacta    180
caataattca tgtataaaac taagggcgta accgaaatcg gttgaaccga accggttag    240
tataaaagca gacattttat gcaccaaaag agaact                              276
```

<210> SEQ ID NO 5
<211> LENGTH: 194
<212> TYPE: DNA
<213> ORGANISM: human papillomavirus type 16

<400> SEQUENCE: 5

```
tagtcataca ttgttcattt gtaaaactgc acatgggtgt gtgcaaaccg attttgggtt     60
acacatttac aagcaactta tataataata ctaaactaca ataattcatg tataaaacta    120
agggcgtaac cgaaatcggt tgaaccgaaa ccggttagta taaaagcaga catttatgc    180
```

| | |
|---|---|
| accaaaagag aact | 194 |

<210> SEQ ID NO 6
<211> LENGTH: 1950
<212> TYPE: DNA
<213> ORGANISM: human papillomavirus type 16

<400> SEQUENCE: 6

| | |
|---|---|
| atggcagacc ccgctggaac aaatggagag gagggcactg ggtgtaacgg ctggttttac | 60 |
| gtggaagcag tcgtagagaa gaagacaggc gacgccattt cagacgacga gaatgagaac | 120 |
| gatagcgaca ctggtgagga tcttgtggac tttattgtga cgacaatga ctatctcacc | 180 |
| caggcagaaa ccgagaccgc ccacgccctc ttcacagccc aggaagctaa gcaacatcgg | 240 |
| gatgcagtgc aggtgctcaa agaaagtac ctggttagtc ctctgtccga catctctgga | 300 |
| tgcgtcgaca taatatcag tccaaggctg aaggctatat gcatagagaa gcagtcaaga | 360 |
| gcggcgaaga ggagactgtt tgaaagcgag atagtggat acgggaacac agaagtcgag | 420 |
| acccaacaga tgctccaggt ggagggtcgc catgagactg agacccctg ctcccagtac | 480 |
| agcggcggat caggcggtgg atgctctcag tactccagtg ggtccggcgg ggagggtgtt | 540 |
| tccgaaagac acaccatctg tcagaccccc ctgactaata ttctgaacgt actgaaaaca | 600 |
| tccaacgcca aggctgccat gctggcgaag tttaaggagc tgtatggcgt gagcttcagc | 660 |
| gaactggtga ccattcaa gagcaacaag agcacctgtt gtgattggtg tattgccgcc | 720 |
| tttgggctga ctccatccat cgctgactct attaaaaccc tgttgcaaca gtactgcctc | 780 |
| tacctgcata ttcagtccct cgcttgctcc tggggaatgg tggtgctgct tctggttcgg | 840 |
| tataagtgtg gcaaaaacag ggagaccatc gagaagctcc ttagtaagct cctgtgtgtg | 900 |
| tctcccatgt gcatgatgat tgaaccgcca aaattgcgga gcacggccgc cgccctgtac | 960 |
| tggtacaaaa caggcataag caacatcagc gaagtgtatg gtgacacgcc agaatggata | 1020 |
| cagagacaga ccgtgctcca gcacagtttt aacgattgca catttgagct gtctcagatg | 1080 |
| gtgcagtggg cttatgataa tgacattgta gacgattccg aaatagcgta taagtacgcc | 1140 |
| cagctcgcag ataccaattc caatgccagc gcatttctga gtccaattc acaggcaaag | 1200 |
| atagtaaagg attgcgctac aatgtgccgc cattataaaa gagcggagaa aaagcagatg | 1260 |
| tcaatgtccc aatggatcaa gtataggtgt gatcgcgttg atgatggcgg tgattggaag | 1320 |
| cagatcgtga tgttcctccg ctatcaaggc gtagaattca tgtcattcct gaccgccctg | 1380 |
| aaacgcttcc tgcagggcat tcctaaaaaa aattgcatcc tgctgtatgg cgcggctaac | 1440 |
| actggaaaga gtctgttcgg catgagcctt atgaagttcc tccagggatc cgtgatatgc | 1500 |
| tttgtgaaca gcaaatcaca cttttggctt cagccattgg cagatgcaaa gatcggcatg | 1560 |
| ctggacgacg ccacagtccc atgctggaac tacatagacg ataatctccg aaacgcattg | 1620 |
| gacggcaatc tggtgagcat ggacgtcaag cacaggcctc tggtgcaact gaagtgtccc | 1680 |
| cctctcctca ttacgtcaaa catcaacgcc ggaacagata tcggtggcc gtacctgcac | 1740 |
| aatagacttg tggtgtttac atttcctaat gaattcccat ttgacgaaaa cggcaatcca | 1800 |
| gtatacgagc tgaatgacaa gaactggaag agttttttct ctaggacatg gtccaggttg | 1860 |
| agtctccacg aagacgagga taaagagaat gacggagact ctttgcccac ttttaagtgc | 1920 |
| gtgtctggac aaaataccaa taccctgtga | 1950 |

<210> SEQ ID NO 7

```
<211> LENGTH: 1098
<212> TYPE: DNA
<213> ORGANISM: human papillomavirus type 16

<400> SEQUENCE: 7
atggagactc tttgccaacg tttaaatgtg tgtcaggaca aaatactaac acattatgaa      60
aatgatagta cagacctacg tgaccatata gactattgga aacacatgcg cctagaatgt    120
gctatttatt acaaggccag agaaatggga tttaaacata ttaaccacca ggtggtgcca    180
acactggctg tatcaaagaa taaagcatta caagcaattg aactgcaact aacgttagaa    240
acaatatata actcacaata tagtaatgaa agtggacat tacaagacgt tagccttgaa     300
gtgtatttaa ctgcaccaac aggatgtata aaaaaacatg gatatacagt ggaagtgcag    360
tttgatggag acatatgcaa tacaatgcat tatacaaact ggacacatat atatatttgt    420
gaagaagcat cagtaactgt ggtagagggt caagttgact attatggttt atattatgtt    480
catgaaggaa tacgaacata ttttgtgcag tttaaagatg atgcagaaaa atatagtaaa    540
aataaagtat gggaagttca tgcgggtggt caggtaatat tatgtcctac atctgtgttt    600
agcagcaacg aagtatcctc tcctgaaatt attaggcagc acttggccaa ccaccccgcc    660
gcgacccata ccaaagccgt cgccttgggc accgaagaaa cacagacgac tatccagcga    720
ccaagatcag agccagacac cggaaacccc tgccacacca ctaagttgtt gcacagagac    780
tcagtggaca gtgctccaat cctcactgca tttaacagct cacacaaagg acggattaac    840
tgtaatagta acactacacc catagtacat ttaaaaggtg atgctaatac tttaaaatgt    900
ttaagatata gatttaaaaa gcattgtaca ttgtatactg cagtgtcgtc tacatggcat    960
tggacaggac ataatgtaaa acataaaagt gcaattgtta cacttacata tgatagtgaa   1020
tggcaacgtg accaatttttt gtctcaagtt aaaataccaa aaactattac agtgtctact   1080
ggatttatgt ctatatga                                                 1098

<210> SEQ ID NO 8
<211> LENGTH: 1443
<212> TYPE: DNA
<213> ORGANISM: human papillomavirus type 16

<400> SEQUENCE: 8
atgtactcca gtgggtccgg cggggagggt gtttccgaaa gacacaccat ctgtcagacc      60
cccctgacta atattctgaa cgtactgaaa acatccaacg ccaaggctgc catgctggcg    120
aagtttaagg agctgtatgg cgtgagcttc agcgaactgg tgagaccatt caagagcaac    180
aagagcacct gttgtgattg gtgtattgcc gcctttgggc tgactccatc catcgctgac    240
tctattaaaa ccctgttgca acagtactgc ctctacctgc atattcagtc cctcgcttgc    300
tcctggggaa tggtggtgct gcttctggtt cggtataagt gtggcaaaaa cagggagacc    360
atcgagaagc tccttagtaa gctcctgtgt gtgtctccca tgcatgat gattgaaccg     420 ccaaaattgc ggagcacggc cgccgccctg tactggtaca aaacaggcat aagcaacatc    480
agcgaagtgt atggtgacac gccagaatgg atacagagac agaccgtgct ccagcacagt    540
tttaacgatt gcacatttga gctgtctcag atggtgcagt gggcttatga taatgacatt    600
gtagacgatt ccgaaatagc gtataagtac gcccagctcg cagataccaa ttccaatgcc    660
agcgcatttc tgaagtccaa ttcacaggca aagatagtaa aggattgcgc tacaatgtgc    720
cgccattata aagagcgga gaaaagcag atgtcaatgt cccaatggat caagtatagg    780
tgtgatcgcg ttgatgatgg cggtgattgg aagcagatcg tgatgttcct ccgctatcaa    840
```

```
ggcgtagaat tcatgtcatt cctgaccgcc ctgaaacgct tcctgcaggg cattcctaaa      900
aaaaattgca tcctgctgta tggcgcggct aacactggaa agagtctgtt cggcatgagc      960
cttatgaagt tcctccaggg atccgtgata tgctttgtga acagcaaatc acacttttgg     1020
cttcagccat tggcagatgc aaagatcggc atgctgacg acgccacagt ccatgctgg       1080 aactacatag acgataatct ccgaaacgca ttggacggca atctggtgag catggacgtc     1140
aagcacaggc tctggtgca actgaagtgt ccccctctcc tcattacgtc aaacatcaac      1200
gccggaacag atagtcggtg gccgtacctg cacaatagac ttgtggtgtt tacatttcct     1260
aatgaattcc catttgacga aacggcaat ccagtatacg agctgaatga caagaactgg      1320
aagagttttt tctctaggac atggtccagg ttgagtctcc acgaagacga ggataaagag     1380
aatgacggag actctttgcc cacttttaag tgcgtgtctg acaaaatac caatacccctg    1440 tga                                                                  1443

<210> SEQ ID NO 9
<211> LENGTH: 1104
<212> TYPE: DNA
<213> ORGANISM: human papillomavirus type 11

<400> SEQUENCE: 9
atggaagcca ttgccaaaag gcttgatgct tgccaggatc agcttctcga gctgtatgag       60
gagaactcta ttgacattca taaacacatc atgcactgga aatgcattag actggagagc     120
gtgttgctgc acaaagcgaa gcagatggga ctgagccaca ttgggcttca ggtggtccca     180
ccccttactg tgtcagagac aaaggggcat aatgccatcg agatgcagat gcatttggag     240
tccctggcga aacccagta tggtgtcgag ccatggacgc tgcaggacac cagttacgaa      300
atgtggctca ccccacccaa acgctgcttt aagaagcagg gaaatactgt ggaggtaaag     360
ttcgatggct gtgaggacaa tgttatggag tacgtggtct ggacacacat ctacttgcag     420
gataatgact cttgggtaaa agtcacttcc tccgttgatg ccaagggcat ctattacacg     480
tgtggacaat tcaagacgta ctacgtcaat ttcaataagg aagctcagaa gtacggcagc     540
acaaaccatt gggaagtttg ctatggctct actgttattt gttcccctgc ttcagtgagt     600
agcacagtcc gggaagtcag tatagccgaa cccaccactt acacccccagc ccagacaacc     660 gcccctacag tttccgcttg caccactgag gacggcgtgt ctgcacctcc ccgcaagcgt     720
gcaagaggac ccagcactaa caacaccctg tgtgtggcca acatacggtc agtggacagt     780
acaatcaaca acatcgtaac cgacaattac aacaagcacc agaggcggaa taattgtcac     840
tccgcagcaa caccgatagt gcaactgcaa ggtgatagca actgcctgaa atgcttccgc     900
tataggctga atgataagta taaacacctg tttgaactgg catctagcac ctggcattgg     960
gcctctcctg aagctccaca caagaacgct attgtgacac tgacttatag ctccgaagag    1020
caacgacagc aatttctgaa cagcgtgaaa atccctccga ccatcagaca taaggtgggg    1080
tttatgtcac tccatctcct ctaa                                           1104

<210> SEQ ID NO 10
<211> LENGTH: 3108
<212> TYPE: DNA
<213> ORGANISM: human papillomavirus type 16

<400> SEQUENCE: 10
atggcagacc ccgctggaac aaatggagag gagggcactg gtgtaacgg ctggttttac       60
```

-continued

```
gtggaagcag tcgtagagaa gaagacaggc gacgccattt cagacgacga gaatgagaac      120
gatagcgaca ctggtgagga tcttgtggac tttattgtga acgacaatga ctatctcacc      180
caggcagaaa ccgagaccgc ccacgccctc ttcacagccc aggaagctaa gcaacatcgg      240
gatgcagtgc aggtgctcaa aagaaagtac ctggttagtc ctctgtccga catctctgga      300
tgcgtcgaca ataatatcag tccaaggctg aaggctatat gcatagagaa gcagtcaaga      360
gcggcgaaga ggagactgtt tgaaagcgag atagtggat acgggaacac agaagtcgag      420
acccaacaga tgctccaggt ggagggtcgc catgagactg agacccctg ctcccagtac       480 agcggcggat caggcggtgg atgctctcag tactccagtg ggtccggcgg ggagggtgtt      540
tccgaaagac acaccatctg tcagaccccc ctgactaata ttctgaacgt actgaaaaca      600
tccaacgcca aggctgccat gctggcgaag tttaaggagc tgtatggcgt gagcttcagc      660
gaactggtga ccattcaa gagcaacaag agcacctgtt gtgattggtg tattgccgcc        720
tttgggctga ctccatccat cgctgactct attaaaaccc tgttgcaaca gtactgcctc      780
tacctgcata ttcagtccct cgcttgctcc tggggaatgg tggtgctgct tctggttcgg      840
tataagtgtg gcaaaaacag ggagaccatc gagaagctcc ttagtaagct cctgtgtgtg      900
tctcccatgt gcatgatgat tgaaccgcca aaattgcgga gcacggccgc cgccctgtac      960
tggtacaaaa caggcataag caacatcagc gaagtgtatg gtgacacgcc agaatggata     1020
cagagacaga ccgtgctcca gcacagtttt aacgattgca catttgagct gtctcagatg     1080
gtgcagtggg cttatgataa tgacattgta gacgattccg aaatagcgta taagtacgcc     1140
cagctcgcag ataccaattc caatgccagc gcatttctga gtccaattc acaggcaaag      1200 atagtaaagg attgcgctac aatgtgccgc cattataaaa gagcggagaa aaagcagatg     1260
tcaatgtccc aatggatcaa gtaggtgt gatcgcgttg atgatggcgg tgattggaag       1320
cagatcgtga tgttcctccg ctatcaaggc gtagaattca tgtcattcct gaccgccctg     1380
aaacgcttcc tgcagggcat tcctaaaaaa aattgcatcc tgctgtatgg cgcggctaac     1440
actggaaaga gtctgttcgg catgagcctt atgaagttcc tccagggatc cgtgatatgc     1500
tttgtgaaca gcaaatcaca cttttggctt cagccattgg cagatgcaaa gatcggcatg     1560
ctggacgacg ccacagtccc atgctggaac tacatagacg ataatctccg aaacgcattg     1620
gacggcaatc tggtgagcat ggacgtcaag cacaggcctc tggtgcaact gaagtgtccc     1680
cctctcctca ttacgtcaaa catcaacgcc ggaacagata gtcggtggcc gtacctgcac     1740
aatagacttg tggtgtttac atttcctaat gaattcccat tgacgaaaa cggcaatcca      1800 gtatacgagc tgaatgacaa gaactggaag agttttttct ctaggacatg gtccaggttg     1860
agtctccacg aagacgagga taaagagaat gacggagact cttttgcccac ttttaagtgc    1920 gtgtctggac aaaataccaa taccctggga agcggagagg gcagaggaag tctgctaaca     1980
tgcggtgacg tcgaggagaa tcctggacct atggagactc tttgccaacg tttaaatgtg     2040
tgtcaggaca aaatactaac acattatgaa aatgatagta cagacctacg tgaccatata     2100
gactattgga acacatgcg cctagaatgt gctatttatt acaaggccag agaaatggga     2160
tttaaacata ttaaccacca ggtggtgcca cactggctg tatcaaagaa taagcatta      2220 caagcaattg aactgcaact aacgttagaa acaatatata actcacaata tagtaatgaa     2280
aagtggacat acaagacgt tagccttgaa gtgtatttaa ctgcaccaac aggatgtata     2340 aaaaacatg gatatacagt ggaagtgcag tttgatggag acatatgcaa tacaatgcat     2400
tatacaaact ggacacatat atatattgt gaagaagcat cagtaactgt ggtagagggt     2460
```

```
caagttgact attatggttt atattatgtt catgaaggaa tacgaacata tttttgtgcag    2520 tttaaagatg atgcagaaaa atatagtaaa aataaagtat gggaagttca tgcgggtggt    2580
caggtaatat tatgtcctac atctgtgttt agcagcaacg aagtatcctc tcctgaaatt    2640
attaggcagc acttggccaa ccactccgcc gcgacccata ccaaagccgt cgccttgggc    2700
accgaagaaa cacagacgac tatgcagcga ccaagatcag agccagacac cggaaacccc    2760
tgccacacca ctaagttgtt gcacagagac tcagtggaca gtgctccaat cctcactgca    2820
tttaacagct cacacaaagg acggattaac tgtaatagta acactacacc catagtacat    2880
ttaaaaggtg atgctaatac tttaaaatgt ttaagtatat gatttaaaaa gcattgtaca    2940
ttgtatactg cagtgtcgtc tacatggcat tggacaggac ataatgtaaa acataaaagt    3000
gcaattgtta cacttacata tgatagtgaa tggcaacgtg accaattttt gtctcaagtt    3060
aaaataccaa aaactattac agtgtctact ggatttatgt ctatatga              3108

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ctaattcact cccaacgaag                                                    20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gccgagtcct gcgtcgagag                                                    20

<210> SEQ ID NO 13
<211> LENGTH: 2187
<212> TYPE: DNA
<213> ORGANISM: Artificial Sequence
<220> FEATURE:
<223> OTHER INFORMATION: Anti-HER2 Antibody

<400> SEQUENCE: 13
atgtacagga tgcaactcct gtcttgcatt gcactaagtc ttgcacttgt cacggaggtt    60
cagctggtgg agtctggcgg tggcctggtg cagccagggg gctcactccg tttgtcctgt    120
gcagcttctg gcttcaacat taaagacacc tatatacact gggtgcgtca ggccccgggt    180
aagggcctgg aatgggttgc aaggatttat cctacgaatg gttatactag atatgccgat    240
agcgtcaagg gccgtttcac tataagcgca gacacatcca aaaacacagc ctacctgcag    300
atgaacagcc tgcgtgctga ggacactgcc gtctattatt gttctagatg ggagggggac    360
ggcttctatg ctatggacgt gtggggtcaa ggaaccctgg tcaccgtctc ctcggctagc    420
accaagggcc catcggtctt ccccctggca ccctcctcca agagcacctc tgggggcaca    480
gcggccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcacccca gacctacatc    660
```

| | |
|---|---|
| tgcaacgtga atcacaagcc cagcaacacc aaggtggaca agaaagttga gcccaaatct | 720 |
| tgtgacaaaa ctcacacatg cccaccgtgc ccagcacctg aactcctggg gggaccgtca | 780 |
| gtcttcctct tccccccaaa acccaaggac accctcatga tctcccggac ccctgaggtc | 840 |
| acatgcgtgg tggtggacgt gagccacgaa gaccctgagg tcaagttcaa ctggtacgtg | 900 |
| gacggcgtgg aggtgcataa tgccaagaca aagccgcggg aggagcagta caacagcacg | 960 |
| taccgtgtgg tcagcgtcct caccgtcctg caccaggact ggctgaatgg caaggagtac | 1020 |
| aagtgcaagg tctccaacaa agccctccca gcccccatcg agaaaaccat ctccaaagcc | 1080 |
| aaagggcagc cccgagaacc acaggtgtac accctgcccc catcccggga tgagctgacc | 1140 |
| aagaaccagg tcagcctgac ctgcctggtc aaaggcttct atcccagcga catcgccgtg | 1200 |
| gagtgggaga gcaatgggca gccggagaac aactacaaga ccacgcctcc cgtgctggac | 1260 |
| tccgacggct ccttcttcct ctacagcaag ctcaccgtgg acaagagcag gtggcagcag | 1320 |
| gggaacgtct tctcatgctc cgtgatgcat gaggctctgc acaaccacta cacgcagaag | 1380 |
| agcctctccc tgtctccggg taaacgtaga cgaaagcgcg gaagcggaga gggcagagga | 1440 |
| agtctgctaa catgcggtga cgtcgaggag aatcctggac ctggatccat gtacaggatg | 1500 |
| caactcctgt cttgcattgc actaagtctt gcacttgtca cggatatcca gatgacccag | 1560 |
| tccccgagct ccctgtccgc ctctgtgggc gatagggtca ccatcacctg ccgtgccagt | 1620 |
| caggatgtga atactgctgt agcctggtat caacagaaac caggaaaagc tccgaaacta | 1680 |
| ctgatttact cggcatcctt cctcgagtct ggagtccctt ctcgcttctc tggttccaga | 1740 |
| tctgggacgg atttcactct gaccatcagc agtctgcagc cggaagactt cgcaacttat | 1800 |
| tactgtcagc aacattatac tactcctccc acgttcggac agggtaccaa ggtggagatc | 1860 |
| aaagaattcg tggctgcacc atctgtcttc atcttcccgc catctgatga gcagttgaaa | 1920 |
| tctggaactg cctctgttgt gtgcctgctg aataacttct atcccagaga ggccaaagta | 1980 |
| cagtggaagg tggataacgc cctccaatcg ggtaactccc aggagagtgt cacagagcag | 2040 |
| gacagcaagg acagcaccta cagcctcagc agcaccctga cgctgagcaa agcagactac | 2100 |
| gagaaacaca aagtctacgc ctgcgaagtc acccatcagg gcctgagctc gcccgtcaca | 2160 |
| aagagcttca caggggaga gtgttag | 2187 |

<210> SEQ ID NO 14
<211> LENGTH: 2085
<212> TYPE: DNA
<213> ORGANISM: Artificial Sequence
<220> FEATURE:
<223> OTHER INFORMATION: Anti-EGFR Antibody

<400> SEQUENCE: 14

| | |
|---|---|
| atgcaggtgc agctgaagca gagcggcccg gggctcgtcc agccctcgca gagcctgagc | 60 |
| atcacctgca cggtgagcgg cttcagcctg accaactacg gggtgcactg ggtccggcag | 120 |
| tcgcccggca aggggctgga gtggctgggc gtgatctgga gcggcgggaa caccgactac | 180 |
| aacaccccct tcacgagccg cctgagcatc aacaaggaca cagcaagtc gcaggtgttc | 240 |
| ttcaagatga acagcctcca gagcaacgac accgccatct actactgcgc gcgggccctg | 300 |
| acctactacg actacgagtt cgcctactgg ggccagggga ccctggtcac ggtgagcgcc | 360 |
| gcgagcacca aggggcccag cgtgttcccc ctcgcccct ccagcaagag caccagcggc | 420 |
| gggaccgccg ccctggctg cctggtcaag gactacttcc ccgagccggt gacggtgagc | 480 |
| tggaactcgg ggccctcac cagcggcgtc cacaccttcc ccgcggtgct gcagagcagc | 540 |

| | |
|---|---|
| gggctgtaca gcctcagctc ggtggtcacc gtgcccagca gcagcctggg cacgcagacc | 600 |
| tacatctgca acgtgaacca caagcccagc aacaccaagg tcgacaagcg cgtggagccg | 660 |
| aagtcgccca agagctgcga caagaccac acgtgcccgc cctgccccgc ccccgagctg | 720 |
| ctcggcgggc ccagcgtgtt cctgttcccg cccaagccca aggacaccct gatgatcagc | 780 |
| cggacccccg aggtcacctg cgtggtggtc gacgtgagcc acgaggaccc ggaggtgaag | 840 |
| ttcaactggt acgtcgacgg cgtggaggtg cacaacgcca agacgaagcc ccgcgaggag | 900 |
| cagtacaaca gcacctaccg ggtcgtgtcg gtgctcaccg tcctgcacca ggactggctg | 960 |
| aacgggaagg agtacaagtg caaggtgagc aacaaggccc tccccgcgcc catcgagaag | 1020 |
| accatcagca aggccaaggg ccagccgcgc gagcccagg tgtacacgct gccccccagc | 1080 |
| cgggacgagc tgaccaagaa ccaggtcagc ctcacctgcc tggtgaaggg gttctacccg | 1140 |
| tcggacatcg ccgtggagtg ggagagcaac ggccagcccg agaacaacta caagaccacg | 1200 |
| cccccggtcc tggacagcga cggcagcttc ttcctctaca gcaagctgac cgtggacaag | 1260 |
| agccgctggc agcaggggaa cgtgttctcg tgcagcgtca tgcacgaggc cctgcacaac | 1320 |
| cactacaccc agaagagcct cagcctgagc cccggcaagt gaggaagcgg agagggcaga | 1380 |
| ggaagtctgc taacatgcgg tgacgtcgag gagaatcctg gacctggatc catggacatc | 1440 |
| ctgctcaccc agagcccggt gatcctgtcg gtcagcccg cgagcgggt gagcttcagc | 1500 |
| tgccgcgcca gccagtcgat cgggacgaac atccactggt accagcagcg gaccaacggc | 1560 |
| agcccccgcc tgctcatcaa gtacgcgagc gagagcatca gcgggattcc ctcgcggttc | 1620 |
| agcggcagcg ggagcggcac cgacttcacc ctgagcatca acagcgtgga gtcggaggac | 1680 |
| atcgccgact actactgcca gcagaacaac aactggccga cgaccttcgg cgccgggacc | 1740 |
| aagctggagc tcaagcgcga attcgtggct gcaccatctg tcttcatctt cccgccatct | 1800 |
| gatgagcagt tgaaatctgg aactgcctct gttgtgtgcc tgctgaataa cttctatccc | 1860 |
| agagaggcca agtacagtg gaaggtggat aacgccctcc aatcgggtaa ctcccaggag | 1920 |
| agtgtcacag agcaggacag caaggacagc acctacagcc tcagcagcac cctgacgctg | 1980 |
| agcaaagcag actacgagaa acacaaagtc tacgcctgcg aagtcaccca tcagggcctg | 2040 |
| agctcgcccg tcacaaagag cttcaacagg ggagagtgtt aggcg | 2085 |

<210> SEQ ID NO 15
<211> LENGTH: 18
<212> TYPE: DNA
<213> ORGANISM: Artificial Sequence
<220> FEATURE:
<223> OTHER INFORMATION: microRNA sequence against CCR5

<400> SEQUENCE: 15

| | |
|---|---|
| gagcaagctc agtttaca | 18 |

<210> SEQ ID NO 16
<211> LENGTH: 1687
<212> TYPE: DNA
<213> ORGANISM: Epstein-Barr Virus

<400> SEQUENCE: 16

| | |
|---|---|
| atgaggatag catatgctac ccggatacag attaggatag catatactac ccagatatag | 60 |
| attaggatag catatgctac ccagatatag attaggatag cctatgctac ccagatataa | 120 |
| attaggatag catatactac ccagatatag attaggatag catatgctac ccagatatag | 180 |

| | |
|---|---|
| attaggatag cctatgctac ccagatatag attaggatag catatgctac ccagatatag | 240 |
| attaggatag catatgctat ccagatattt gggtagtata tgctacccag atataaatta | 300 |
| ggatagcata tactacccta atctctatta ggatagcata tgctacccgg atacagatta | 360 |
| ggatagcata tactacccag atatagatta ggatagcata tgctacccag atatagatta | 420 |
| ggatagccta tgctacccag atataaatta ggatagcata tactacccag atatagatta | 480 |
| ggatagcata tgctacccag atatagatta ggatagccta tgctacccag atatagatta | 540 |
| ggatagcata tgctatccag atatttgggt agtatatgct acccatggca acattagccc | 600 |
| accgtgctct cagcgacctc gtgaatatga ggaccaacaa ccctgtgctt ggcgctcagg | 660 |
| cgcaagtgtg tgtaatttgt cctccagatc gcagcaatcg cgcccctatc ttggcccgcc | 720 |
| cacctactta tgcaggtatt ccccggggtg ccattagtgg ttttgtgggc aagtggtttg | 780 |
| accgcagtgg ttagcggggt tacaatcagc caagttatta caccctta tt ttacagtcca | 840 |
| aaaccgcagg gcggcgtgtg ggggctgacg cgtgccccca ctccacaatt tcaaaaaaaa | 900 |
| gagtggccac ttgtctttgt ttatgggccc cattggcgtg gagcccgtt taattttcgg | 960 |
| gggtgttaga gacaaccagt ggagtccgct gctgtcggcg tccactctct ttccccttgt | 1020 |
| tacaaataga gtgtaacaac atggttcacc tgtcttggtc cctgcctggg acacatctta | 1080 |
| ataaccccag tatcatattg cactaggatt atgtgttgcc catagccata aattcgtgtg | 1140 |
| agatggacat ccagtctttta cggcttgtcc ccaccccatg gatttctatt gttaaagata | 1200 |
| ttcagaatgt ttcattccta cactagtatt tattgcccaa ggggtttgtg agggttatat | 1260 |
| tggtgtcata gcacaatgcc accactgaac ccccgtcca aatttattc tgggggcgtc | 1320 |
| acctgaaacc ttgttttcga gcacctcaca tacaccttac tgttcacaac tcagcagtta | 1380 |
| ttctattagc taaacgaagg agaatgaaga agcaggcgaa gattcaggag agttcactgc | 1440 |
| ccgctccttg atcttcagcc actgcccttg tgactaaaat ggttcactac cctcgtggaa | 1500 |
| tcctgacccc atgtaaataa aaccgtgaca gctcatgggg tgggagatat cgctgttcct | 1560 |
| taggacccctt ttactaaccc taattcgata gcatatgctt cccgttgggt aacatatgct | 1620 |
| attgaattag ggttagtctg gatagtatat actactaccc gggaagcata tgctacccgt | 1680 |
| ttagggt | 1687 |

<210> SEQ ID NO 17
<211> LENGTH: 726
<212> TYPE: DNA
<213> ORGANISM: Homo sapiens

<400> SEQUENCE: 17

| | |
|---|---|
| atgaatcgct gctgggcgct cttcctgtct ctctgctgct acctgcgtct ggtcagcgcc | 60 |
| gaggggggacc ccattcccga ggagctttat gagatgctga gtgaccactc gatccgctcc | 120 |
| tttgatgatc tccaacgcct gctgcacgga gaccccggag aggaagatgg ggccgagttg | 180 |
| gacctgaaca tgacccgctc ccactctgga ggcgagctga gagcttggc tcgtggaaga | 240 |
| aggagcctgg gttccctgac cattgctgag ccggccatga tcgccgagtg caagacgcgc | 300 |
| accgaggtgt cgagatctc ccggcgcctc atagaccgca ccaacgccaa cttcctggtg | 360 |
| tggcccgccct gtgtggaggt gcagcgctgc tccggctgct gcaacaaccg caacgtgcag | 420 |
| tgccgccccca cccaggtgca gctgcgacct gtccaggtga aaagatcga gattgtgcgg | 480 |
| aagaagccaa tctttaagaa ggccacggtg acgctggaag accacctggc atgcaagtgt | 540 |
| gagacagtgg cagctgcacg gcctgtgacc cgaagcccgg ggggttccca ggagcagcga | 600 |

| | |
|---|---|
| gccaaaacgc cccaaactcg ggtgaccatt cggacggtgc gagtccgccg gccccccaag | 660 |
| ggcaagcacc ggaaattcaa gcacacgcat gacaagacgg cactgaagga gacccttgga | 720 |
| gcctag | 726 |

<210> SEQ ID NO 18
<211> LENGTH: 2193
<212> TYPE: DNA
<213> ORGANISM: Homo sapiens

<400> SEQUENCE: 18

| | |
|---|---|
| atgcccggcg tggcccgcct gccgctgctg ctcgggctgc tgctgctccc gcgtcccggc | 60 |
| cggccgctgg acttggccga ctacacctat gacctggcgg aggaggacga ctcggagccc | 120 |
| ctcaactaca agacccctg caaggcggct gccttttcttg gggacattgc cctgacgaa | 180 |
| gaggacctga gggccttcca ggtacagcag ctgtggatc tcagacggca cacagctcgt | 240 |
| aagtcctcca tcaaagctgc agttccagga aacacttcta cccccagctg ccagagcacc | 300 |
| aacgggcagc tcagagggg agcctgtggg agatggagag gtagatcccg tagccggcgg | 360 |
| gcggcgacgt cccgaccaga gcgtgtgtgg cccgatgggg tcatcccctt tgtcattggg | 420 |
| ggaaacttca ctggtagcca gagggcagtc ttccggcagg ccatgaggca ctgggagaag | 480 |
| cacacctgtg tcaccttcct ggagcgcact gacgaggaca gctatattgt gttcacctat | 540 |
| cgaccttgcg ggtgctgctc ctacgtgggt cgccgcggcg ggggccccca ggccatctcc | 600 |
| atcggcaaga actgtgacaa gttcggcatt gtggtccacg agctgggcca cgtcgtcggc | 660 |
| ttctggcacg aacacactcg gccagaccgg gaccgccacg tttccatcgt tcgtgagaac | 720 |
| atccagccag gcaggagta taacttcctg aagatggagc tcaggaggt ggagtccctg | 780 |
| ggggagacct atgacttcga cagcatcatg cattacgctc ggaacacatt ctccaggggc | 840 |
| atcttcctgg ataccattgt ccccaagtat gaggtgaacg gggtgaaacc tcccattggc | 900 |
| caaaggacac ggctcagcaa ggggacatt gcccaagccc gcaagcttta caagtgccca | 960 |
| gcctgtggag agaccctgca agacagcaca ggcaacttct cctcccctga atacccaat | 1020 |
| ggctactctg ctcacatgca ctgcgtgtgg cgcatctctg tcacacccgg ggagaagatc | 1080 |
| atcctgaact tcacgtccct ggacctgtac cgcagccgcc tgtgctggta cgactatgtg | 1140 |
| gaggtccgag atggcttctg gaggaaggcg ccctccgag gccgcttctg cgggtccaaa | 1200 |
| ctccctgagc ctatcgtctc cactgacagc cgcctctggg ttgaattccg cagcagcagc | 1260 |
| aattgggttg gaaagggctt ctttgcagtc tacgaagcca tctgcggggg tgatgtgaaa | 1320 |
| aaggactatg ccacattca atcgcccaac tacccagacg attaccggcc cagcaaagtc | 1380 |
| tgcatctggc ggatccaggt gtctgaggc ttccacgtgg gctcacatt ccagtccttt | 1440 |
| gagattgagc gccacgacag ctgtgcctac gactatctgg aggtgcgcga cgggcacagt | 1500 |
| gagagcagca ccctcatcgg gcgctactgt ggctatgaga agcctgatga catcaagagc | 1560 |
| acgtccagcc gcctctggct caagttcgtc tctgacgggt ccattaacaa agcgggcttt | 1620 |
| gccgtcaact ttttcaaaga ggtggacgag tgctctcggc ccaaccgcgg gggctgtgag | 1680 |
| cagcggtgcc tcaacaccct gggcagctac aagtgcagct gtgaccccgg gtacgagctg | 1740 |
| gccccagaca gcgccgctg tgaggctgct tgtggcggat tcctcaccaa gctcaacggc | 1800 |
| tccatcacca gccgggctg gcccaaggag tacccccca acaagaactg catctggcag | 1860 |
| ctggtggccc ccacccagta ccgcatctcc ctgcagtttg acttctttga gacagagggc | 1920 |

| | |
|---|---|
| aatgatgtgt gcaagtacga cttcgtggag gtgcgcagtg gactcacagc tgactccaag | 1980 |
| ctgcatggca agttctgtgg ttctgagaag cccgaggtca tcacctccca gtacaacaac | 2040 |
| atgcgcgtgg agttcaagtc cgacaacacc gtgtccaaaa agggcttcaa ggcccacttc | 2100 |
| ttctcagaaa agaggccagc tctgcagccc cctcggggac gcccccacca gctcaaattc | 2160 |
| cgagtgcaga aagaaaccg gaccccccag tga | 2193 |

<210> SEQ ID NO 19
<211> LENGTH: 7905
<212> TYPE: DNA
<213> ORGANISM: human papillomavirus type 16

<400> SEQUENCE: 19

| | |
|---|---|
| actacaataa tccatgtata aaactaaggg cgtaaccgaa atcggttgaa ccgaaaccgg | 60 |
| ttagtataaa agcagacatt ttatgcacca aaagagaact gcaatgtttc aggacccaca | 120 |
| ggagcgaccc ggaaagttac cacagttatg cacagagctg caaacaacta tacatgatat | 180 |
| aatattagaa tgtgtgtact gcaagcaaca gttactgcga cgtgaggtat atgactttgc | 240 |
| ttttcgggat ttatgcatag tatatagaga tgggaatcca tatgctgtat gtgataaatg | 300 |
| tttaaagttt tattctaaaa ttagtgagta tagacattat tgttatagtg tgtatggaac | 360 |
| aacattagaa cagcaataca acaaaccgtt gtgtgatttg ttaattaggt gtattaactg | 420 |
| tcaaaagcca ctgtgtcctg aagaaaagca agacatctg acaaaaagc aaagattcca | 480 |
| taatataagg ggtcggtgga ccggtcgatg tatgtcttgt tgcagatcat caagaacacg | 540 |
| tagagaaacc cagctgtaat catgcatgga gatacaccta cattgcatga atatatgtta | 600 |
| gatttgcaac cagagacaac tgatctctac tgttatgagc aattaaatga cagctcagag | 660 |
| gaggaggatg aaatagatgg tccagctgga caagcagaac cggacagagc ccattacaat | 720 |
| attgtaacct tttgttgcaa gtgtgactct acgcttcggt tgtgcgtaca aagcacacac | 780 |
| gtagacattc gtactttgga agacctgtta atgggcacac taggaattgt gtgccccatc | 840 |
| tgttctcaga accataatc taccatggct gatcctgcag gtaccaatgg ggaagagggt | 900 |
| acgggatgta atggatggtt ttatgtagag gctgtagtgg aaaaaaaaac agggatgct | 960 |
| atatcagatg acgagaacga aatgacagt gatacaggtg aagatttggt agatttttata | 1020 |
| gtaaatgata tgattatttt aacacaggca gaaacagaga cagcacatgc gttgtttact | 1080 |
| gcacaggaag caaacaaca tagagatgca gtacaggttc taaaacgaaa gtatttgggt | 1140 |
| agtccactta gtgatattag tggatgtgta gacaataata ttagtcctag attaaaagct | 1200 |
| atatgtatag aaaaacaaag tagagctgca aaaggagat tatttgaaag caaagacagc | 1260 |
| gggtatggca atactgaagt ggaaactcag cagatgttac aggtagaagg cgcccatgag | 1320 |
| actgaaacac catgtagtca gtatagtggt ggaagtgggg gtggttgcag tcagtacagt | 1380 |
| agtggaagtg ggggagaggg tgttagtgaa agacacaata tatgccaaac accacttaca | 1440 |
| aatattttaa atgtactaaa aactagtaat gcaaaggcag caatgttagc aaaatttaaa | 1500 |
| gagttatacg gggtgagttt tacagaatta gtaagaccat ttaaaagtaa taaatcaacg | 1560 |
| tgttgcgatt ggtgtattgc tgcatttgga cttacacccc gtagcgtga cagtataaaa | 1620 |
| acactattac aacaatattg tttatattta cacattcaaa gtttagcatg ttcatgggga | 1680 |
| atggttgtgt tactattagt aagatataaa tgtggaaaaa atagagaaac aattgaaaaa | 1740 |
| ttgctgtcta aactattatg tgtgtctcca atgtgtatga tgatagagcc tccaaaattg | 1800 |
| cgtagtacag cagcagcatt atattggtat aaaacaggta tatcaaatat tagtgaagtg | 1860 |

```
tatggagaca cgccagaatg gatacaaaga caaacagtat tacaacatag ttttaatgat    1920
tgtacatttg aattatcaca gatggtacaa tgggcctacg ataatgacat agtagacgat    1980
agtgaaattg catataaata tgcacaattg gcagacacta atagtaatgc aagtgccttt    2040
ctaaaaagta attcacaggc aaaaattgta aaggattgtg caacaatgtg tagacattat    2100
aaacgagcag aaaaaaaaca aatgagtatg agtcaatgga taaaatatag atgtgatagg    2160
gtagatgatg gaggtgattg gaagcaaatt gttatgtttt taaggtatca aggtgtagag    2220
tttatgtcat ttttaactgc attaaaaaga ttttttgcaag gcatacctaa aaaaaattgc    2280
atattactat atggtgcagc taacacaggt aaatcattat ttggtatgag tttaatgaaa    2340
tttctgcaag ggtctgtaat atgttttgta aattctaaaa gccattttgg ttacaaccaa    2400
ttagcagatg ccaaaatagg tatgttagat gatgctacag tgccctgttg gaactatata    2460
gatgacaatt taagaaatgc attggatgga aatttagttt ctatggatgt aaagcataga    2520
ccattggtac aactaaaatg ccctccatta ttaattacat ctaacattaa tgctggtaca    2580
gattctaggt ggccttattt acataataga ttggtggtgt ttacatttcc taatgagttt    2640
ccatttgacg aaaacggaaa tccagtgtat gagcttaatg ataagaactg gaaatccttt    2700
ttctcaagga cgtggtccag attaagtttg cacgaggacg aggacaagga aaacgatgga    2760
gactctttgc caacgtttaa atgtgtgtca ggacaaaata ctaacacatt atgaaaatga    2820
tagtacagac ctacgtgacc atatagacta ttggaaacac atgcgcctag aatgtgctat    2880
ttattacaag gccagagaaa tgggatttaa acatattaac caccaggtgg tgccaacgct    2940
ggctgtatca aagaataaag cattacaagc aattgaactg caactaacgt tagaaacaat    3000
atataactca caatatagta atgaaaagtg gacattacaa gacgttagcc ttgaagtgta    3060
tttaactgca ccaacaggat gtataaaaaa acatggatat acagtggaag tgcagtttga    3120
tggagacata tgcaatacaa tgcattatac aaactggaca catatatata tttgtgaaga    3180
agcatcagta actgtggtag agggtcaagt tgactattat ggtttatatt atgttcatga    3240
aggaatacga acatattttg tgcagtttaa agatgatgca gaaaaatata gtaaaaataa    3300
agtatgggaa gttcatgcgg gtggtcaggt aatattatgt cctacatctg tgtttagcag    3360
caacgaagta tcctctcctg aaactattag gcagcacttg gccaaccact ccgccgcgac    3420
ccataccaaa gccgtcgcct tgggcaccga agaaacacag acgactatcc agcgaccaag    3480
atcagagcca gacaccggaa acccctgcca caccactaag ttgttgcaca gagactcagt    3540
ggacagtgct ccaatcctca ctgcatttaa cagctcacac aaaggacgga ttaactgtaa    3600
tagtaacact acacccatag tacatttaaa aggtgatgct aatactttaa aatgtttaag    3660
atatagattt aaaaagcatt gtaaattgta tactgcagtg tcgtctacat ggcattggac    3720
aggacataat gtaaaacata aaagtgcaat tgttacactt acatatgata gtgaatggca    3780
acgtgaccaa ttttttgtctc aagttaaaat accaaaaact attacagtgt ctactggatt    3840
tatgtctata tgacaaatct tgatactgca tacacaacat tactggcgtg cttttttgctt    3900 tgcttttgtg tgcttttgtg tgtctgccta ttaatacgtc cgctgctttt gtctgtgtct    3960
acatacacat cattaatact attggtatta ctattgtgga taacagcagc ctctgcgttt    4020
aggtgtttta ttgtatatat tgtatttgtt tatataccat tatttttaat acatacacat    4080
gcacgctttt taattacata atgtatatgt acataatgta attgttacat ataattgttg    4140
tataccataa cttactattt tttctttttt attttatat ataattttt tttggtttgt    4200
```

```
ttgtttgttt tttaataaac tgttctcact taacaatgcg acacaaacgt tctgcaaaac    4260
gcacaaaacg tgcatcggct acccaacttt ataaaacatg caaacaggca ggtacatgtc    4320
cacctgacat tatacctaag gttgaaggca aaactattgc tgatcaaata ttacaatatg    4380
gaagtatggg tgtattttt ggtgggttag gaattggaac agggtcgggt acaggcggac    4440
gcactgggta tattccattg ggaacaaggc ctcccacagc tacagataca cttgctcctg    4500
taagaccccc tttaacagta gatcctgtgg gcccttctga tccttctata gtttctttag    4560
tggaagaaac tagttttatt gatgctggtg caccaacatc tgtaccttcc atcccccag    4620 atgtatcagg atttagtatt actacttcaa ctgataccac acctgctata ttagatatta    4680
ataatactgt tactactgtt actacacata ataatcccac tttcactgac ccatctgtat    4740
tgcagcctcc aacacctgca gaaactggag ggcattttac actttcatca tccactatta    4800
gtacacataa ttatgaagaa attcctatgg atacatttat tgttagcaca aaccctaaca    4860
cagtaactag tagcacaccc ataccagggt ctcgcccagt ggcacgccta ggattatata    4920
gtcgcacaac acaacaagtt aaagttgtag accctgcttt tgtaaccact cccactaaac    4980 ttattcacata tgataatcct gcatatgaag gtatagatgt ggataataca ttatatttc     5040 ctagtaatga taatagtatt aatatagctc cagatcctga cttttggat atagttgctt      5100 tacataggcc agcattaacc tctaggcgta ctggcattag gtacagtaga attggtaata    5160
aacaaacact acgtactcgt agtggaaaat ctataggtgc taaggtacat tattattatg    5220
atttgagtac tattgatcct gcagaagaaa tagaattaca aactataaca ccttctacat    5280
atactaccac ttcacatgca gcctcaccta cttctattaa taatggctta tatgatattt    5340
atgcagatga ctttattaca gatacttcta caaccccggt accatctgta ccctctacat    5400
ctttatcagg ttatattcct gcaaatacaa caattccttt tggtggtgca tacaatattc     5460
ctttagtatc aggtcctgat atacccatta atataactga ccaagctcct tcattaattc    5520
ctatagttcc agggtctcca caatatacaa ttattgctga tgcaggtgac ttttatttac    5580
atcctagtta ttacatgtta cgaaaacgac gtaaacgttt accatatttt ttttcagatg    5640 tctcttggc tgcctagtga ggccactgtc tacttgcctc ctgtcccagt atctaaggtt       5700
gtaagcacgg atgaatatgt tgcacgcaca acatatatt atcatgcagg aacatccaga    5760
ctacttgcag ttggacatcc ctattttcct attaaaaaac ctaacaataa caaaatatta    5820
gttcctaaag tatcaggatt acaatacagg gtatttagaa tacatttacc tgaccccaat    5880
aagtttggtt ttcctgacac ctcatttat aatccagata cacagcggct ggtttgggcc     5940
tgtgtaggtg ttgaggtagg tcgtggtcag ccattaggtg tgggcattag tggccatcct     6000
ttattaaata aattggatga cacagaaaat gctagtgctt atgcagcaaa tgcaggtgtg    6060
gataatagag aatgtatatc tatggattac aaacaaacac aattgtgttt aattggttgc    6120
aaaccaccta taggggaaca ctggggcaaa ggatccccat gtaccaatgt tgcagtaaat    6180
ccaggtgatt gtccaccatt agagttaata aacacagtta ttcaggatgg tgatatggtt    6240
gatactggct ttggtgctat ggactttact acattacagg ctaacaaaag tgaagttcca    6300
ctggatattt gtacatctat ttgcaaatat ccagattata ttaaaatggt gtcagaacca    6360
tatggcgaca gcttattttt ttatttacga agggaacaaa tgtttgttag acatttattt    6420
aatagggctg gtgctgttgg tgaaaatgta ccagacgatt tatacattaa aggctctggg    6480
tctactgcaa atttagccag ttcaaattat tttcctacac ctagtggttc tatggttacc    6540
tctgatgccc aaatattcaa taaaccttat tggttacaac gagcacaggg ccacaataat    6600
```

```
ggcatttgtt ggggtaacca actatttgtt actgttgttg atactacacg cagtacaaat    6660
atgtcattat gtgctgccat atctacttca gaaactacat ataaaaatac taactttaag    6720
gagtacctac gacatgggga ggaatatgat ttacagttta ttttttcaact gtgcaaaata   6780 accttaactg cagacgttat gacatacata cattctatga attccactat tttggaggac   6840
tggaattttg gtctacaacc cccccccagga ggcacactag aagatactta taggtttgta   6900
acatcccagg caattgcttg tcaaaaacat acacctccag cacctaaaga agatcccctt    6960
aaaaaataca cttttttggga agtaaattta aaggaaaagt tttctgcaga cctagatcag    7020
tttcctttag gacgcaaatt tttactacaa gcaggattga aggccaaacc aaaatttaca    7080
ttaggaaaac gaaaagctac acccaccacc tcatctacct ctacaactgc taaacgcaaa    7140
aaacgtaagc tgtaagtatt gtatgtatgt tgaattagtg ttgtttgttg tttatatgtt    7200
tgtatgtgct tgtatgtgct tgtaaatatt aagttgtatg tgtgtttgta tgtatggtat    7260
aataaacacg tgtgtatgtg ttttttaaatg cttgtgtaac tattgtgtga tgcaacataa    7320
ataaacttat tgtttcaaca cctactaatt gtgttgtggt tattcattgt atataaacta    7380
tatttgctac aatctgtttt tgttttatat atactatatt ttgtagcgcc agcggccatt    7440
ttgtagcttc aaccgaattc ggttgcatgc ttttttggcac aaaatgtgtt tttttaaata    7500
gttctatgtc agcaactata gtttaaactt gtacgtttcc tgcttgccat gcgtgccaaa    7560
tccctgtttt cctgacctgc actgcttgcc aaccattcca ttgttttttta cactgcacta    7620 tgtgcaacta ctgaatcact atgtacattg tgtcatataa aataaatcac tatgcgccaa    7680
cgccttacat accgctgtta ggcacatatt tttggcttgt tttaactaac ctaattgcat    7740
atttggcata aggtttaaac ttctaaggcc aactaaatgt caccctagtt catacatgaa    7800
ctgtgtaaag gttagtcata cattgttcat ttgtaaaact gcacatgggt gtgtgcaaac    7860
cgttttgggt tacacattta caagcaactt atataataat actaa                    7905
```

<210> SEQ ID NO 20
<211> LENGTH: 33
<212> TYPE: DNA
<213> ORGANISM: Artificial Sequence
<220> FEATURE:
<223> OTHER INFORMATION: Primer

<400> SEQUENCE: 20
ggatccgcca ccatggagag cgacgagagc ggc        33

<210> SEQ ID NO 21
<211> LENGTH: 27
<212> TYPE: DNA
<213> ORGANISM: Artificial Sequence
<220> FEATURE:
<223> OTHER INFORMATION: Primer

<400> SEQUENCE: 21
gaattcttag cgagatccgg tggagcc                27

<210> SEQ ID NO 22
<211> LENGTH: 41
<212> TYPE: DNA
<213> ORGANISM: human immunodeficiency virus

<400> SEQUENCE: 22
tacgccaaaa attttgacta gcggaggcta gaaggagaga g    41

```
<210> SEQ ID NO 23
<211> LENGTH: 233
<212> TYPE: DNA
<213> ORGANISM: human immunodeficiency virus

<400> SEQUENCE: 23
aggagctttg ttccttgggt tcttgggagc agcaggaagc actatgggcg cagcctcaat    60
gacgctgacg gtacaggcca gacaattatt gtctggtata gtgcagcagc agaacaattt   120
gctgagggct attgaggcgc aacagcatct gttgcaactc acagtctggg gcatcaagca   180
gctccaggca agaatcctgg ctgtggaaag atacctaaag gatcaacagc tcc          233

<210> SEQ ID NO 24
<211> LENGTH: 118
<212> TYPE: DNA
<213> ORGANISM: human immunodeficiency virus

<400> SEQUENCE: 24
ttttaaaaga aaagggggga ttgggggggta cagtgcaggg gaaagaatag tagacataat    60
agcaacagac atacaaacta agaattaca aaaacaaatt acaaaattca aaattta         118

<210> SEQ ID NO 25
<211> LENGTH: 590
<212> TYPE: DNA
<213> ORGANISM: woodchuck hepatitis virus

<400> SEQUENCE: 25
aatcaacctc tgattacaaa atttgtgaaa gattgactgg tattcttaac tatgttgctc    60
cttttacgct atgtggatac gctgctttaa tgcctttgta tcatgctatt gcttcccgta   120
tggctttcat tttctcctcc ttgtataaat cctggttgct gtctctttat gaggagttgt   180
ggcccgttgt caggcaacgt ggcgtggtgt gcactgtgtt tgctgacgca accccactg    240 gttgggcat tgccaccacc tgtcagctcc tttccgggac tttcgctttc ccctcccta     300 ttgccacggc ggaactcatc gccgcctgcc ttgcccgctg ctggacaggg gctcggctgt   360
tgggcactga caattccgtg tgttgtcgg ggaaatcatc gtcctttcct tggctgctcg    420
cctgtgttgc cacctggatt ctgcgcggga cgtccttctg ctacgtccct tcggccctca   480
atccagcgga ccttccttcc gcggcctgc tgccggctct gcggcctctt ccgcgtcttc    540
gccttcgccc tcagacgagt cggatctccc tttgggccgc ctccccgcct                590

<210> SEQ ID NO 26
<211> LENGTH: 1239
<212> TYPE: DNA
<213> ORGANISM: Homo sapiens

<400> SEQUENCE: 26
atgacggaca gacagacaga caccgccccc agcccagct accacctcct ccccggccgg    60
cggcggacag tggacgcggc ggcgagccgc ggcaggggc cggagcccgc gcccggaggc    120
ggggtggagg gggtcggggc tcgcggcgtc gcactgaaac ttttcgtcca acttctgggc   180
tgttctcgct tcggaggagc cgtggtccgc gcggggaag ccgagccgag cggagccgcg    240
agaagtgcta gctcgggccg ggaggagccg cagccggagg aggggaggga ggaagaagag   300
aaggaagagg agaggggccc gcagtggcga ctcggcgctc ggaagccggg ctcatggacg   360
ggtgaggcgc cggtgtgcgc agacagtgct ccagccgcgc gcgctcccca ggccctggcc   420
cgggcctcgg gccggggagg aagagtagct cgccgaggcg ccgaggagag cgggccgccc   480
```

```
cacagcccga gccggagagg gagcgcgagc cgcgccggcc ccggtcgggc ctccgaaacc      540
atgaactttc tgctgtcttg ggtgcattgg agccttgcct tgctgctcta cctccaccat      600
gccaagtggt cccaggctgc acccatggca gaaggaggag ggcagaatca tcacgaagtg      660
gtgaagttca tggatgtcta tcagcgcagc tactgccatc caatcgagac cctggtggac      720
atcttccagg agtaccctga tgagatcgag tacatcttca agccatcctg tgtgcccctg      780
atgcgatgcg ggggctgctg caatgacgag ggcctggagt gtgtgcccac tgaggagtcc      840
aacatcacca tgcagattat gcggatcaaa cctcaccaag ccagcacat aggagagatg       900 agcttcctac agcacaacaa atgtgaatgc agaccaaaga aagatagagc aagacaagaa      960
aaaaaatcag ttcgaggaaa gggaagggg caaaaacgaa agcgcaagaa atcccggtat      1020
aagtcctgga gcgtgtacgt tggtgcccgc tgctgtctaa tgccctggag cctccctggc     1080
ccccatccct gtgggccttg ctcagagcgg agaaagcatt tgtttgtaca agatccgcag     1140
acgtgtaaat gttcctgcaa aaacacagac tcgcgttgca aggcgaggca gcttgagtta     1200
aacgaacgta cttgcagatg tgacaagccg aggcggtga                            1239

<210> SEQ ID NO 27
<211> LENGTH: 180
<212> TYPE: DNA
<213> ORGANISM: human papillomavirus type 16

<400> SEQUENCE: 27
ggtctctctg gttagaccag atctgagcct gggagctctc tggctaacta gggaacccac       60
tgcttaagcc tcaataaagc ttgccttgag tgcttcaagt agtgtgtgcc cgtctgttgt      120
gtgactctgg taactagaga tccctcagac ccttttagtc agtgtggaaa atctctagca      180

<210> SEQ ID NO 28
<211> LENGTH: 250
<212> TYPE: DNA
<213> ORGANISM: human papillomavirus type 16

<400> SEQUENCE: 28
tggaagggct aattcactcc caacgaagat aagatctgct ttttgcttgt actgggtctc       60
tctggttaga ccagatctga gcctgggagc tctctggcta actagggaac ccactgctta      120
agcctcaata aagcttgcct tgagtgcttc aagtagtgtg tgcccgtctg ttgtgtgact      180
ctggtaacta gagatccctc agaccctttt agtcagtgtg gaaaatctct agcagtagta      240
gttcatgtca                                                            250

<210> SEQ ID NO 29
<211> LENGTH: 350
<212> TYPE: DNA
<213> ORGANISM: cytomegalovirus

<400> SEQUENCE: 29
actagtatta tgcccagtac atgaccttat gggactttcc tacttggcag tacatctacg       60
tattagtcat cgctattacc atggtgatgc ggttttggca gtacatcaat gggcgtggat      120
agcggtttga ctcacgggga tttccaagtc tccaccccat tgacgtcaat gggagtttgt      180
tttggcacca aaatcaacgg gactttccaa aatgtcgtaa caactccgcc ccattgacgc      240
aaatgggcgg taggcgtgta cggtgggagg tttatataag cagagctcgt ttagtgaacc      300
gtcagatcgc ctggagacgc catccacgct gttttgacct ccatagaaga               350
```

<210> SEQ ID NO 30
<211> LENGTH: 1162
<212> TYPE: DNA
<213> ORGANISM: human papillomavirus type 16

<400> SEQUENCE: 30

| | | | | | |
|---|---|---|---|---|---|
| gcgccgggtt | ttggcgcctc | ccgcgggcgc | cccctcctc | acggcgagcg | ctgccacgtc | 60 |
| agacgaaggg | cgcaggagcg | ttcctgatcc | ttccgcccgg | acgctcagga | cagcggcccg | 120 |
| ctgctcataa | gactcggcct | tagaaccca | gtatcagcag | aaggacattt | taggacggga | 180 |
| cttgggtgac | tctagggcac | tggttttctt | tccagagagc | ggaacaggcg | aggaaaagta | 240 |
| gtcccttctc | ggcgattctg | cggagggatc | tccgtgggc | ggtgaacgcc | gatgattata | 300 |
| taaggacgcg | ccgggtgtgg | cacagctagt | tccgtcgcag | ccgggatttg | gtcgcggtt | 360 |
| cttgttgtg | gatcgctgtg | atcgtcactt | ggtgagttgc | gggctgctgg | gctggccggg | 420 |
| gctttcgtgg | ccgccgggcc | gctcggtggg | acggaagcgt | gtggagagac | cgccaagggc | 480 |
| tgtagtctgg | gtccgcgagc | aaggttgccc | tgaactgggg | gttgggggga | gcgcacaaaa | 540 |
| tggcggctgt | tcccgagtct | tgaatggaag | acgcttgtaa | ggcgggctgt | gaggtcgttg | 600 |
| aaacaaggtg | gggggcatgg | tgggcggcaa | gaacccaagg | tcttgaggcc | ttcgctaatg | 660 |
| cgggaaagct | cttattcggg | tgagatgggc | tggggcacca | tctggggacc | ctgacgtgaa | 720 |
| gtttgtcact | gactggagaa | ctcgggtttg | tcgtctggtt | gcggggcgg | cagttatgcg | 780 |
| gtgccgttgg | gcagtgcacc | cgtacctttg | ggagcgcgcg | cctcgtcgtg | tcgtgacgtc | 840 |
| acccgttctg | ttggcttata | atgcaggtg | gggccacctg | ccggtaggtg | tgcggtaggc | 900 |
| ttttctccgt | cgcaggacgc | agggttcggg | cctagggtag | gctctcctga | atcgacaggc | 960 |
| gccggacctc | tggtgagggg | agggataagt | gaggcgtcag | tttctttggt | cggttttatg | 1020 |
| tacctatctt | cttaagtagc | tgaagctccg | gttttgaact | atgcgctcgg | ggttggcgag | 1080 |
| tgtgtttttgt | gaagtttttt | aggcaccttt | tgaaatgtaa | tcatttgggt | caatatgtaa | 1140 |
| ttttcagtgt | tagactagta | aa | | | | 1162 |

<210> SEQ ID NO 31
<211> LENGTH: 1687
<212> TYPE: DNA
<213> ORGANISM: Epstein-Barr Virus

<400> SEQUENCE: 31

| | | | | | |
|---|---|---|---|---|---|
| atgaggatag | catatgctac | ccggatacag | attaggatag | catatactac | ccagatatag | 60 |
| attaggatag | catatgctac | ccagatatag | attaggatag | cctatgctac | ccagatataa | 120 |
| attaggatag | catatactac | ccagatatag | attaggatag | catatgctac | ccagatatag | 180 |
| attaggatag | cctatgctac | ccagatatag | attaggatag | catatgctac | ccagatatag | 240 |
| attaggatag | catatgctat | ccagatattt | gggtagtata | tgctacccag | atataaatta | 300 |
| ggatagcata | tactacccta | atctctatta | ggatagcata | tgctacccgg | atacagatta | 360 |
| ggatagcata | tactacccag | atatagatta | ggatagcata | tgctacccag | atatagatta | 420 |
| ggatagccta | tgctacccag | atataaatta | ggatagcata | tactacccag | atatagatta | 480 |
| ggatagcata | tgctacccag | atatagatta | ggatagccta | tgctacccag | atatagatta | 540 |
| ggatagcata | tgctatccag | atatttgggt | agtatatgct | acccatggca | acattagccc | 600 |
| accgtgctct | cagcgacctc | gtgaatatga | ggaccaacaa | cctgtgctt | ggcgctcagg | 660 |
| cgcaagtgtg | tgtaatttgt | cctccagatc | gcagcaatcg | cgcccctatc | ttggcccgcc | 720 |

```
cacctactta tgcaggtatt ccccggggtg ccattagtgg ttttgtgggc aagtggtttg      780
accgcagtgg ttagcggggt tacaatcagc caagttatta cacccttatt ttacagtcca      840
aaaccgcagg gcggcgtgtg ggggctgacg cgtgccccca ctccacaatt tcaaaaaaaa      900
gagtggccac ttgtctttgt ttatgggccc cattggcgtg gagccccgtt taattttcgg      960
gggtgttaga gacaaccagt ggagtccgct gctgtcggcg tccactctct ttccccttgt     1020
tacaaataga gtgtaacaac atggttcacc tgtcttggtc cctgcctggg acacatctta     1080
ataaccccag tatcatattg cactaggatt atgtgttgcc catagccata aattcgtgtg     1140
agatggacat ccagtcttta cggcttgtcc ccacccatg gatttctatt gttaaagata      1200
ttcagaatgt ttcattccta cactagtatt tattgcccaa ggggtttgtg agggttatat     1260
tggtgtcata gcacaatgcc accactgaac ccccgtcca aatttattc tgggggcgtc       1320 acctgaaacc ttgttttcga gcacctcaca tacaccttac tgttcacaac tcagcagtta     1380
ttctattagc taaacgaagg agaatgaaga agcaggcgaa gattcaggag agttcactgc     1440
ccgctccttg atcttcagcc actgcccttg tgactaaaat ggttcactac cctcgtggaa     1500
tcctgacccc atgtaaataa aaccgtgaca gctcatgggg tgggagatat cgctgttcct     1560
taggaccctt ttactaaccc taattcgata gcatatgctt cccgttgggt aacatatgct     1620
attgaattag ggttagtctg gatagtatat actactaccc gggaagcata tgctacccgt     1680
ttagggt                                                               1687

<210> SEQ ID NO 32
<211> LENGTH: 1926
<212> TYPE: DNA
<213> ORGANISM: Epstein-Barr Virus

<400> SEQUENCE: 32
atgtctgacg aggggccagg tacaggacct ggaaatggcc taggagagaa gggagacaca       60
tctggaccag aaggctccgg cggcagtgga cctcaaagaa gaggggtga taaccatgga      120 cgaggacggg gaagaggacg aggacgagga ggcggaagac caggagcccc gggcggctca      180
ggatcagggc caagacatag agatggtgtc cggagacccc aaaaacgtcc aagttgcatt      240
ggctgcaaag ggaccacgg tggaacagga gcaggagcag gagcgggagg ggcaggagca      300
ggaggggcag gagcaggagg aggggcagga gcaggaggag gggcaggagg ggcaggaggg      360
gcaggagggg caggagcagg aggaggggca ggagcaggag gaggggcagg aggggcagga      420
ggggcaggag caggaggagg gcaggagca ggaggagggg caggagggg aggagcagga       480 ggaggggcag gaggggcagg aggggcagga gcaggaggag gggcaggagc aggaggaggg      540
gcaggagggg caggagcagg aggaggggca ggaggggcag gaggggcagg agcaggagga      600
ggggcaggag caggaggggc aggaggggca ggaggggcag gagcaggagg ggcaggagca      660
ggaggagggg caggaggggc aggaggggca ggagcaggag gggcaggagc aggaggggca      720
ggagcaggag gggcaggagc aggaggggca ggaggggcag gagcaggagg ggcaggaggg      780
gcaggagcag gaggggcagg agggggcagga gcaggaggag gggcaggagg ggcaggagca      840
ggaggagggg caggaggggc aggagcagga ggggcaggag gggcaggagc aggaggggca      900 ggagggggcag gagcaggagg ggcaggaggg gcaggagcag gaggagggggc aggagcagga      960 ggggcaggag caggaggtgg aggccggggt cgaggaggca gtggaggccg ggtcgagga     1020 ggtagtggag gccggggtcg aggaggtagt ggaggccgcc ggggtagagg acgtgaaaga     1080
```

-continued

```
gccaggggg   gaagtcgtga  aagagccagg  gggagaggtc  gtggacgtgg  agaaaagagg   1140
cccaggagtc  ccagtagtca  gtcatcatca  tccgggtctc  caccgcgcag  gccccctcca   1200
ggtagaaggc  cattttttcca ccctgtaggg  gaagccgatt  attttgaata  ccaccaagaa   1260
ggtggcccag  atggtgagcc  tgacgtgccc  ccgggagcga  tagagcaggg  ccccgcagat   1320
gacccaggag  aaggcccaag  cactggaccc  cggggtcagg  gtgatggagg  caggcgcaaa   1380
aaaggagggt  ggtttggaaa  gcatcgtggt  caaggaggtt  ccaacccgaa  atttgagaac   1440
attgcagaag  gtttaagagc  tctcctggct  aggagtcacg  tagaaaggac  taccgacgaa   1500
ggaacttggg  tcgccggtgt  gttcgtatat  ggaggtagta  agacctccct  ttacaaccta   1560
aggcgaggaa  ctgcccttgc  tattccacaa  tgtcgtctta  caccattgag  tcgtctcccc   1620
tttggaatgg  ccctggacc   cggcccacaa  cctggcccgc  taagggagtc  cattgtctgt   1680
tatttcatgg  tcttttttaca aactcatata  tttgctgagg  ttttgaagga  tgcgattaag   1740
gaccttgtta  tgacaaagcc  cgctcctacc  tgcaatatca  gggtgactgt  gtgcagcttt   1800
gacgatggag  tagatttgcc  tccctggttt  ccacctatgg  tggaaggggc  tgccgcggag   1860
ggtgatgacg  gagatgacgg  agatgaagga  ggtgatggag  atgagggtga  ggaagggcag   1920
gagtga                                                                  1926
```